(12) United States Patent
Blumberg et al.

(10) Patent No.: US 9,556,271 B2
(45) Date of Patent: Jan. 31, 2017

(54) ANTI-CEACAM1 RECOMBINANT ANTIBODIES FOR CANCER THERAPY

(71) Applicant: THE BRIGHAM AND WOMEN'S HOSPITAL, INC., Boston, MA (US)

(72) Inventors: Richard S. Blumberg, Waltham, MA (US); Yu-Hwa Huang, Boston, MA (US); Nalan Utku, Luxembourg (LU)

(73) Assignee: The Brigham and Women's Hospital, Inc., Boston, MA (US)

(*) Notice: Subject to any disclaimer, the term of this patent is extended or adjusted under 35 U.S.C. 154(b) by 0 days.

(21) Appl. No.: 14/362,022

(22) PCT Filed: Nov. 30, 2012

(86) PCT No.: PCT/US2012/067207
§ 371 (c)(1),
(2) Date: May 30, 2014

(87) PCT Pub. No.: WO2013/082366
PCT Pub. Date: Jun. 6, 2013

(65) Prior Publication Data
US 2014/0328841 A1  Nov. 6, 2014

Related U.S. Application Data

(60) Provisional application No. 61/565,640, filed on Dec. 1, 2011.

(51) Int. Cl.
| | | |
|---|---|---|
| A61K 39/395 | (2006.01) |
| C07K 16/28 | (2006.01) |
| C07K 16/30 | (2006.01) |
| A61K 47/48 | (2006.01) |
| A61K 39/00 | (2006.01) |

(52) U.S. Cl.
CPC ..... *C07K 16/2803* (2013.01); *A61K 47/48576* (2013.01); *C07K 16/3007* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 6,852,320 B2 | 2/2005 | Blumberg | |
| 7,132,255 B2 | 11/2006 | Blumberg | |
| 8,598,322 B2 * | 12/2013 | Markel | C07K 16/2803 424/130.1 |
| 2004/0047858 A1 * | 3/2004 | Blumberg | C07K 16/2803 424/131.1 |

FOREIGN PATENT DOCUMENTS

| | | | |
|---|---|---|---|
| WO | 99/52552 A1 | 4/1999 |
| WO | 2004/024746 A2 | 3/2004 |
| WO | WO2004024746 A2 | 3/2004 |
| WO | 2005/058358 A2 | 6/2005 |
| WO | 2009/092108 A2 | 7/2009 |
| WO | 2010/125571 A1 | 11/2010 |
| WO | WO2010125571 A1 | 11/2010 |

OTHER PUBLICATIONS

Simeone et al (Pancreas, 2007, 34:436-443, IDS).*
Beauchemin et al., "Redefined nomenclature for members of the carcinoembryonic antigen family", Exp. Cell Res. 252(2): 243-249 (1999).
Briese et al., "Expression pattern of osteopontin in endometrial carcinoma: correlation with expression of the adhesion molecule CEACAM1", Intl. J. Gynecol. Pathol., 25(2): 161-169 (2006).
Dango et al., "Elevated expression of carcinoembryonic antigen-related cell adhesion molecule 1 (CEACAM-1) is associated with increased angiogenic potential in non-small-cell lung cancer", Lung Cancer, 60(3): 426-433 (2008).
Gambichler et al., "Protein Expression of Carcinoembryonic Antigen Cell Adhesion Molecules in Benign and Malignant Melanocytic Skin Lesions", J. Clin. Pathol. 131: 782-787 (2009).
Gray-Owen et al, "CEACAM1: contact-dependent control of immunity", Natl Rev Immunol., 6(6):433-446 (2006).
Horst et al., "Carcinoembryonic antigen-related cell adhesion molecule 1 modulates vascular remodeling in vitro and in vivo", J. Clin. Invest., 116(6): 1596-1605 (2006).
Kang et al., "The expression of CD66a and possible roles in colorectal adenoma and adenocarcinoma", Intl. J. Colorectal Dis., 22: 869-874 (2007).
Lee et al., "CEACAM1 Dynamics during Neisseria gonorrhoeae Suppression of CD4 T Lymphocyte Activation", J. Immunol. 180: 6827-6835 (2008).
Liu et al., "CEACAM1 impedes thyroid cancer growth but promotes invasiveness: a putative mechanism for early metastases", Oncogene, 26: 2747-2758 (2007).
Markel et al., "Inhibition of Human Tumor-Infiltrating Lymphocyte Effector Functions by the Homophilic Carcinoembryonic Cell Adhesion Molecule 1 Interactions", J. Immunol., 177: 6062-6071 (2006).
Markel et al., "Systemic dysregulation of CEACAM1 in melanoma patients", Cancer Immunol. Immunother., 59: 215 (2010).
Morales et al., "Regulation of Human Intestinal Intraepithelial Lymphocyte Cytolytic Function by Biliary Glycoprotein", J Immunol, 163(3): 1363-1370 (1999).
Sienel et al., "Elevated Expression of Carcinoembryonic Antigen-related Cell Adhesion Molecule 1 Promotes Progression of Non-Small Cell Lung Cancer", Clin. Cancer Res., 9: 2260-2266 (2003).
Simeone et al., "CEACAM1, a Novel Serum Biomarker for Pancreatic Cancer", Pancreas, 34(4): 436-443 (2007).
Singer et al., "Carcinoembryonic Antigen-Related Cell Adhesion Molecule 1 Expression and Signaling in Human, Mouse, and Rat Leukocytes: Evidence for Replacement of the Short Cytoplasmic Domain Isoform by Glycosylphosphatidylinkositol-Linked Protein in Human Leukocytes", J Immunol, 168(10): 5139-5146 (2002).

(Continued)

*Primary Examiner* — Laura B Goddard
(74) *Attorney, Agent, or Firm* — Nixon Peabody LLP; Mark J. FitzGerald

(57) ABSTRACT

Provided herein are recombinant monoclonal antibodies and antigen-binding portions thereof useful in inhibiting CEACAM1 in tumor cells, and methods of their use in anti-tumor proliferation and invasiveness therapies, such as the treatment of cancer, particularly pancreatic cancer.

9 Claims, 24 Drawing Sheets

(56) References Cited

OTHER PUBLICATIONS

Slevogt et al., "CEACAM1 inhibits Toll-like receptor 2-triggered antibacterial responses of human pulmonary epithelial cells", Nat. Immunol., 9(11): 1270-1278 (2008).
Tilki et al., "CEACAM1: A Novel Urinary Marker for Bladder Cancer Detection", Eur. Assoc. Urol., 57: 648-654 (2010).
Wagener et al., "Angiogenic Properties of the Carcinoembryonic Antigen-Related Cell Adhesion Molecule 1", Exp. Cell Res., 261: 19-24 (2000).
Watt et al., "Homophilic adhesion of human CEACAM1 involves N-terminal domain interactions: structural analysis of the binding site", Blood, 98: 1469-1479 (2001).
Xi et al., "Whole genome exon arrays identify differential expression of alternatively spliced, cancer-related genes in lung cancer", Nucl. Acids Res. 36(20): 6535-6547 (2008).
Zhou et al., "The different expression of carcinoembryonic antigen-related cell adhesion molecule 1 (CEACAM1) and possible roles in gastric carcinomas", Pathol. Res. Pract., 205: 483-489 (2009).
Zhou et al., "CEACAM1 distribution and its effects on angiogenesis and lymphangiogenesis in oral carcinoma", Oral Oncology, 45: 883-886 (2009).

\* cited by examiner

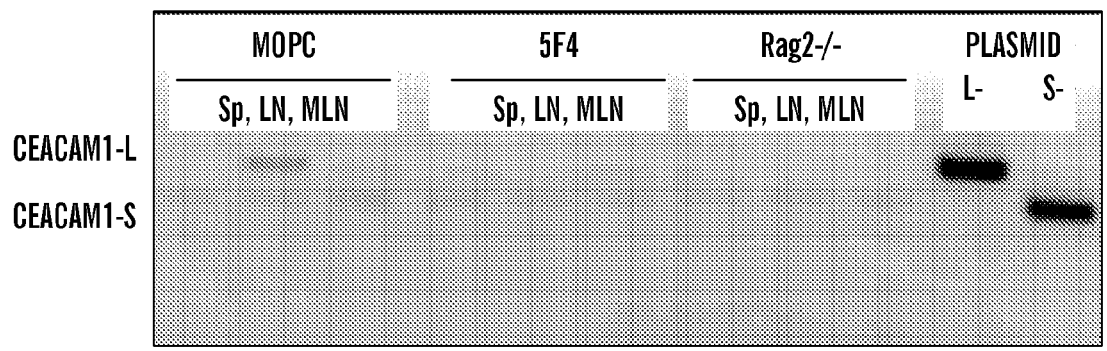
FIG. 4B
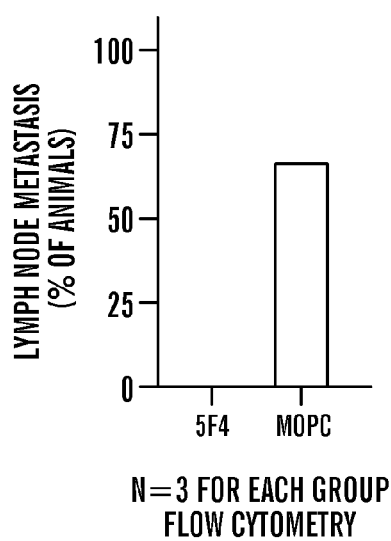 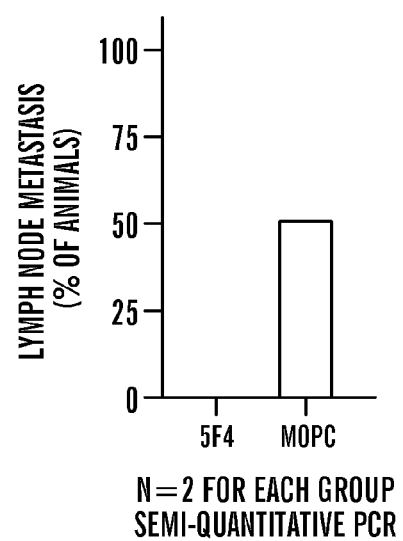
FIG. 4C  FIG. 4D

5F4 MOPC

Hybridoma 5F4/2C6/2H3 Heavy Chain Sequences

```
          10          20          30          40          50          60          70          80          90         100
GAGGTGCAGTTGGTGGAGTCTGGGGGAGACTTGGTGAAGCCTGGAGGGTCCCTGAAACTCGCCTGTGCAGCCTCTGGATTCATTTT|CAGTAGCCATGGCA
 E   V   Q   L   V   E   S   G   G   D   L   V   K   P   G   G   S   L   K   L   A   C   A   A   S   G   F   I   F  |S   S   H   G
                        10                          20                                                      30

110         120         130         140         150         160         170         180         190         200
TGTCT|TGGGTTCGCCAGACTCCAGAGACAAGAGGCTGGAGTGGGTCGCA|ACCATTAGCAGTGGTGGTACTTACACCTACTATCCAGACAGTGTGAAGGGCCG
 M   S|  W   V   R   Q   T   P   D   K   R   L   E   W   V   A|  T   I   S   S   G   G   T   Y   T   Y   Y   P   D   S   V   K   G   R
                 40                                             50  52 A                            60

210         220         230         240         250         260         270         280         290         300
ATTCACCATATCCAGAGACAATGACAAGAACACCCTGTACCTGCAAATGAACAGTCTGAAGTCTGAGGACACAGCCATGTATTACTGTGCAAGA|CACGAC
 F   T   I   S   R   D   N   D   K   N   T   L   Y   L   Q   M   N   S   L   K   S   E   D   T   A   M   Y   Y   C   A   R|  H   D
                 70                                 80  82 A B C                            90

310         320         330         340         350         360
TTTGATTACGACGCGGGCCTGGTTTGCTTAC|TGGGGCCAAGGGACTCTGGTCACTGTCTCTGCA
 F   D   Y   D   A   A   W   F   A   Y|  W   G   Q   G   T   L   V   T   V   S   A
         100 A B C D                            110
```

*FIG. 14*

Hybridoma 5F4/2C6/2H3 Light Chain Sequences

```
         10         20         30         40         50         60         70         80         90        100
CAAATTGTTCTCACCCAGTCTCCAGCACTCATGTCTGCATCTCCAGGGGTGAAAGTCACCATGACCTGCAGTGCCAACTCAAGTGTAAGTTACATGTATT
 Q  I  V  L  T  Q  S  P  A  L  M  S  A  S  P  G  V  K  V  T  M  T  C  S  A  N  S  S  V  S  Y  M  Y
                      10                      20                          26 28         30

110        120        130        140        150        160        170        180        190        200
GGTATCGGCAGAAGCCAAGATCCTCCCCCAAACCCTGGATTTATCTCACATCCAACCTGGCTTCTGGAGTCCCTGCTCGCTTCAGTGGCAGTGGGTCTGG
 W  Y  R  Q  K  P  R  S  S  P  K  P  W  I  Y  L  T  S  N  L  A  S  G  V  P  A  R  F  S  G  S  G  S  G
                      40                       50                                     60

210        220        230        240        250        260        270        280        290        300
GACCTCTTATTCTCTCACAATCAGCAGCATGGAGGCTGAAGATGCTGCCACTTATTACTGCCAGCAGTGGAGTAGTAACCCACCCACGTTCGGCTCGGGG
 T  S  Y  S  L  T  I  S  S  M  E  A  E  D  A  A  T  Y  Y  C  Q  Q  W  S  S  N  P  P  T  F  G  S  G
                      70                   80                                    90                       100

310
ACAAAGTTGGAAATAAAAA
 T  K  L  E  I  K
       106 A
```

*FIG. 15*

Hybridoma 34B1/2E8/2E6 Heavy Chain Sequences

```
         10         20         30         40         50         60         70         80         90        100
GAGGTGCAGCTGGTGGAGTCTGGGGGAGACTTAGTGAAGCCTGGAGGGTCCCTGAAACTCTCCTGTGCAGCCTCTGGATTCACTTTC AGTTTCTATGGCA
 E   V   Q   L   V   E   S   G   G   D   L   V   K   P   G   G   S   L   K   L   S   C   A   A   S   G   F   T   F   S   F   Y   G
                                 10                          20                                              30

110        120        130        140        150        160        170        180        190        200
TGTCTTTGGGTTCGCCAGACTCCAGAGACAAGAGAGGCTGGAGTGGGTCGCA ACCTTTAGTGGTGGTGGTAATTACACTTACTATCCAGACAGTGTGAAGGGGCG
 M   S   W   V   R   Q   T   P   D   K   R   L   E   W   V   A   T   F   S   G   G   G   N   Y   T   Y   Y   P   D   S   V   K   G   R
         40                                                  50   52 A                       60

210        220        230        240        250        260        270        280        290        300
ATTCACCATCTCCAGAGACAATGCCAAGAACACCCTTTACCTGCAAATGAGCAGTCTGAAGTCTGAGGACACAGCCAGGTATTACTGTGCAAGA CATGGG
 F   T   I   S   R   D   N   A   K   N   T   L   Y   L   Q   M   S   S   L   K   S   E   D   T   A   R   Y   Y   C   A   R   H   G
             70                           80   82 A B C                              90

310        320        330        340        350        360
GGGTTACCATTTTATGCTATGGACTAC TGGGGTCAAGGAACCTCAGTCACCGTCTCCTCA
 G   L   P   F   Y   A   M   D   Y   W   G   Q   G   T   S   V   T   V   S   S
         100 A B C                          110
```

FIG. 16

Hybridoma 34B1/2E8/2E6 Light Chain Sequences

```
        10         20         30         40         50         60         70         80         90        100
GAAATTGTGATCACCCAGTCTCCAGCACTCATGGCTGCAGCTCCTGCATCTCCAGGGGAGAAGGTCACCATCACCTGCAGTGTCTCCTCAAGTATAAGTTCCAGCAACT
 E  I  V  I  T  Q  S  P  A  L  M  A  A  S  P  A  S  P  G  E  K  V  T  I  T  C  S  V  S  S  S  I  S  S  N
                     10                      20                       27 A       30

110        120        130        140        150        160        170        180        190        200
TGCACTGGTACCAGCAGAAGTCAGAACCTCCCCCAAACCCTGGATTTATGCACATTTAACCTGGCTTCTGGAGTCCCTGTTCGCTTCAGTGGCAGTGG
 L  H  W  Y  Q  Q  K  S  E  T  S  P  K  P  W  I  Y  G  T  F  N  L  A  S  G  V  P  V  R  F  S  G  S  G
                     40                      50                      60

210        220        230        240        250        260        270        280        290        300
ATCTGGGACCTCTTATTCTCTCACAATCAGCAGCATGGAGGCTGAAGATGCTGCCACTTATTACTGTCAACAGTGGAGTAGTCACCCATTCACGTTCGGC
 S  G  T  S  Y  S  L  T  I  S  S  M  E  A  E  D  A  A  T  Y  Y  C  Q  Q  W  S  S  H  P  F  T  F  G
              70                     80                        90

310        320
TCGGGGACAAAGTTGGAAATAAAA
 S  G  T  K  L  E  I  K
       100        106 A
```

FIG. 17

Hybridoma 26H7/2H9/2E10 Heavy Chain Sequences

```
         10          20          30          40          50          60          70          80          90         100
GAAGTGCAGCTGGTGGAGTCTGGGGGAGGCTTGGTGAAGCCTGGGGGGTCCCTGAAACTCTCCTGTGCAGCCTCTGGATTCTCTTTCAGTGACTATTACT
 E  V  Q  L  V  E  S  G  G  G  L  V  K  P  G  G  S  L  K  L  S  C  A  A  S  G  F  S  F  S  D  Y  Y
                              10                          20                          30

110         120         130         140         150         160         170         180         190         200
TGTATTGGGTTCGCCAGACTCCGGAAAAAGGCTGGAGTGGGTCGCAACCATTAGTGGTGGTGGTAACACCTCCTATCCGGACAGTGTGAAGGGCG
 L  Y  W  V  R  Q  T  P  E  K  R  L  E  W  V  A  T  I  S  V  G  G  G  N  T  S  Y  P  D  S  V  K  G  R
                40                          50    52 A                           60

210         220         230         240         250         260         270         280         290         300
ATTCACCATCTCCAGAGACAATGCCAAGAACAACCTGTACCTGCAAATGAGCAGTCTGAAGTCTGAAGATACAGCCATGTATTACTGTACAAGGGGCCTT
 F  T  I  S  R  D  N  A  K  N  N  L  Y  L  Q  M  S  S  L  K  S  E  D  T  A  M  Y  Y  C  T  R  G  L
                70                          80    82 A  B  C              90

310         320         330         340         350         360
TACTACGGCCCCGGCCCCTGGTTTGCTTACTGGGGCCAAGGGACTCTGGTCACTGTCTCTGCA
 Y  Y  G  P  A  W  F  A  Y  W  G  Q  G  T  L  V  T  V  S  A
     100 A  B  C                           110
```

FIG. 18

Hybridoma 26H7/2H9/2E10 Light Chain Sequences (seq1)

```
         10         20         30         40         50         60         70         80         90        100
GACATTGTGATGACACAGTCTCCATCCTCCCTGGCTATGTCAGTAGGACAGAAGGTCACTATGAGCTGCAAGTCCAGTCAGAGCCTTTAAATATGTAGCA
 D  I  V  M  T  Q  S  P  S  S  L  A  M  S  V  G  Q  K  V  T  M  S  C  K  S  S  Q  S  L  N  S  S
                 10                  20                          27 A B C D E F 110        120        130        140        150        160        170        180        190        200
ATCAAAAGAACTATTTGGCCTGGTTCCAGCAGACACCAGGACAGTCTCCTAAACTTCTGGTATACTTTGCATCCACTAGGGAATCTGGGGTCCCTGATCG
 N  Q  K  N  Y  L  A  W  F  Q  Q  T  P  G  Q  S  P  K  L  L  V  Y  F  A  S  T  R  E  S  G  V  P  D  R
        30                         40                          50                          60

210        220        230        240        250        260        270        280        290        300
CTTCATAGGCAGTGGGTCTGGGACAGATTTCACTCTCTTACCATCAGCAGTGTGAAGGCTGAGGACCTGGCAGATTACTTCTGTCAGCAACATTATAGCACT
 F  I  G  S  G  S  G  T  D  F  T  L  T  I  S  S  V  K  A  E  D  L  A  D  Y  F  C  Q  Q  H  Y  S  T
                 70                          80                          90

310        320        330
CCGTGGACGTTCGGTGGAGGCACCAAGCTGGAAATCAGA
 P  W  T  F  G  G  G  T  K  L  E  I  R
        100              106 A
```

FIG. 19

Hybridoma 26H7/2H9/2E10 Light Chain Sequences (seq2)

```
         10         20         30         40         50         60         70         80         90        100
GACATCCAGATGACCCAGTCTCCATCCTCCTTATCTGCCTCTCTGGGAGAAAGAGTCAGTCTCACTTGTCGGGCAAGTCAGAAAATTAGTGGTTACTTAA
 D  I  Q  M  T  Q  S  P  S  S  L  S  A  S  L  G  E  R  V  S  L  T  C  R  A  S  Q  K  I  S  G  Y  L
                   10                  20                                   30

110        120        130        140        150        160        170        180        190        200
GCTGGCTTCAGCAGAAACCTGATGGAACTATTAAGCGCCTCATCTACGCCGCCATCCACTTTAGATTCTGGTGTCCCAAAAGGTTCAGTGGCAGTAGGTC
 S  W  L  Q  Q  K  P  D  G  T  I  K  R  L  I  Y  A  A  S  T  L  D  S  G  V  P  K  R  F  S  G  S  R  S
                   40                  50                                   60

210        220        230        240        250        260        270        280        290        300
TGGGTCAGATTATTCTCTCACCATCAGCAGCCTTGAGTCTGAAGATTTTGCAGACTATTACTGTCTACAATATGCTAGTTCTCTCATGTACACGTTCGGA
 G  S  D  Y  S  L  T  I  S  S  L  E  S  E  D  F  A  D  Y  Y  C  L  Q  Y  A  S  S  L  M  Y  T  F  G
                   70                  80                                   90                  95  A 310        320
GGGGGGACCAAACTGGAAATAAAAG
 G  G  T  K  L  E  I  K
100                106  A
```

*FIG. 19 (cont.)*

SEQUENCE LISTING

<160> NUMBER OF SEQ ID NOS: 42

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ser His Gly Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Ile Ser Ser Gly Gly Thr Tyr Thr Tyr Tyr Pro Asp Ser Val Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Asp Phe Asp Tyr Asp Ala Ala Trp Phe Ala Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Ala Asn Ser Ser Val Ser Tyr Met Tyr
1               5                   10

<210> SEQ ID NO 5
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 5

Leu Thr Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Trp Ser Ser Asn Pro Pro Thr
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Phe Tyr Gly Met Ser
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Phe Ser Gly Gly Gly Asn Tyr Thr Tyr Tyr Pro Asp Ser Val Lys
1               5                   10                  15

Gly

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

His Gly Gly Leu Pro Phe Tyr Ala Met Asp Tyr
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Val Ser Ser Ser Ile Ser Ser Ser Asn Leu His
1               5                   10
```

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Thr Phe Asn Leu Ala Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln Trp Ser Ser His Pro Phe Thr
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Asp Tyr Tyr Leu Tyr
1               5

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Ile Ser Val Gly Gly Gly Asn Thr Ser Tyr Pro Asp Ser Val Lys
1               5                   10                  15

Gly

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Leu Thr Thr Gly Pro Ala Trp Phe Ala Tyr
1               5                   10

<210> SEQ ID NO 16
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 16

Lys Ser Ser Gln Ser Leu Leu Asn Ser Ser Asn Gln Lys Asn Tyr Leu
1               5                   10                  15

Ala

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Phe Ala Ser Thr Arg Glu Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Gln His Tyr Ser Thr Pro Trp Thr
1               5

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ala Ser Gln Lys Ile Ser Gly Tyr Leu Ser
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ala Ser Thr Leu Asp Ser
1               5

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Gln Tyr Ala Ser Ser Leu Met Tyr Thr
1               5                   10
```

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Glu Val Gln Leu Val Glu Ser Gly Gly Asp Leu Val Lys Pro Gly Gly
1               5                   10                  15

Ser Leu Lys Leu Ala Cys Ala Ala Ser Gly Phe Ile Phe Ser Ser His
            20                  25                  30

Gly Met Ser Trp Val Arg Gln Thr Pro Asp Lys Arg Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Asp Lys Asn Thr Leu Tyr
65                  70                  75                  80

Leu Gln Met Asn Ser Leu Lys Ser Glu Asp Thr Ala Met Tyr Tyr Cys
                85                  90                  95

Ala Arg His Asp Phe Asp Tyr Asp Ala Ala Trp Phe Ala Tyr Trp Gly
            100                 105                 110

Gln Gly Thr Leu Val Thr Val Ser Ala
        115                 120
```

<210> SEQ ID NO 27
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Gln Ile Val Leu Thr Gln Ser Pro Ala Leu Met Ser Ala Ser Pro Gly
1               5                   10                  15

Val Lys Val Thr Met Thr Cys Ser Ala Asn Ser Ser Val Ser Tyr Met
```

```
                20                  25                  30
Tyr Trp Tyr Arg Gln Lys Pro Arg Ser Ser Pro Lys Pro Trp Ile Tyr
            35                  40                  45

Leu Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Ser Gly Thr Lys Leu Glu Ile Lys
            100                 105

<210> SEQ ID NO 28
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Phe Tyr
            20                  25                  30

Gly Met Ser Trp Val Arg Gln Thr Pro Asp Lys Arg Leu Glu Trp Val
        35                  40                  45

Ala Thr Phe Ser Gly Gly Asn Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Arg Tyr Tyr Cys
                85                  90                  95

Ala Arg His Gly Gly Leu Pro Phe Tyr Ala Met Asp Tyr Trp Gly Gln
            100                 105                 110

Gly Thr Ser Val Thr Val Ser Ser
        115                 120

<210> SEQ ID NO 29
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Ile Val Ile Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Asn Leu His Trp Tyr Gln Gln Lys Ser Glu Thr Ser Pro Lys Pro Trp
        35                  40                  45

Ile Tyr Gly Thr Phe Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser His Pro
```

```
                    85                  90                  95
Phe Thr Phe Gly Ser Gly Thr Lys Leu Glu Ile Lys
                100                 105

<210> SEQ ID NO 30
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Glu Ser Gly Gly Gly Phe Val Lys Pro Gly Gly
1               5                   10                  15

Ser Leu Lys Leu Ser Cys Ala Ala Ser Gly Phe Ser Phe Ser Asp Tyr
                20                  25                  30

Tyr Leu Tyr Trp Val Arg Gln Thr Pro Glu Lys Arg Leu Glu Trp Val
            35                  40                  45

Ala Thr Ile Ser Val Gly Gly Asn Thr Ser Tyr Pro Asp Ser Val
        50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Thr Arg Gly Leu Tyr Tyr Gly Pro Ala Trp Phe Ala Tyr Trp Gly Gln
                100                 105                 110

Gly Thr Leu Val Thr Val Ser Ala
            115                 120

<210> SEQ ID NO 31
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
                20                  25                  30

Ser Asn Gln Lys Asn Tyr Leu Ala Trp Phe Gln Thr Pro Gly Gln
            35                  40                  45

Ser Pro Lys Leu Leu Val Tyr Phe Ala Ser Thr Arg Glu Ser Gly Val
        50                  55                  60

Pro Asp Arg Phe Ile Gly Ser Gly Ser Gly Thr Asp Phe Thr Leu Thr
65                  70                  75                  80

Ile Ser Ser Val Lys Ala Glu Asp Leu Ala Asp Tyr Phe Cys Gln Gln
                85                  90                  95

His Tyr Ser Thr Pro Trp Thr Phe Gly Gly Gly Thr Lys Leu Glu Ile
                100                 105                 110

Arg

<210> SEQ ID NO 32
<211> LENGTH: 108
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Lys Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Ser Leu Met
                85                  90                  95

Tyr Thr Phe Gly Gly Gly Thr Lys Leu Glu Ile Lys
            100                 105

<210> SEQ ID NO 33
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 33 gag gtg cag ttg gtg gag tct ggg gga gac ttg gtg aag cct gga ggg     48
Glu Val Gln Leu Val Glu Ser Gly Gly Asp Leu Val Lys Pro Gly Gly
1               5                   10                  15 tcc ctg aaa ctc gcc tgt gca gcc tct gga ttc att ttc agt agc cat     96
Ser Leu Lys Leu Ala Cys Ala Ala Ser Gly Phe Ile Phe Ser Ser His
            20                  25                  30 ggc atg tct tgg gtt cgc cag act cca gac aag agg ctg gag tgg gtc    144
Gly Met Ser Trp Val Arg Gln Thr Pro Asp Lys Arg Leu Glu Trp Val
        35                  40                  45 gca acc att agc agt ggt ggt act tac acc tac tat cca gac agt gtg    192
Ala Thr Ile Ser Ser Gly Gly Thr Tyr Thr Tyr Tyr Pro Asp Ser Val
    50                  55                  60 aag ggg cga ttc acc ata tcc aga gac aat gac aaa aac acc ctg tac    240
Lys Gly Arg Phe Thr Ile Ser Arg Asp Asn Asp Lys Asn Thr Leu Tyr
65                  70                  75                  80 ctg caa atg aac agt ctg aag tct gag gac aca gcc atg tat tac tgt    288
Leu Gln Met Asn Ser Leu Lys Ser Glu Asp Thr Ala Met Tyr Tyr Cys
                85                  90                  95 gca aga cac gac ttt gat tac gac gcg gcc tgg ttt gct tac tgg ggc    336
Ala Arg His Asp Phe Asp Tyr Asp Ala Ala Trp Phe Ala Tyr Trp Gly
                100                 105                 110 caa ggg act ctg gtc act gtc tct gca                                363
Gln Gly Thr Leu Val Thr Val Ser Ala
            115                 120

<210> SEQ ID NO 34
<211> LENGTH: 318
<212> TYPE: DNA
<213> ORGANISM: Artificial Sequence
<220> FEATURE:
```

```
<223> OTHER INFORMATION: Description of Artificial Sequence: Synthetic
      polynucleotide
<220> FEATURE:
<221> NAME/KEY: CDS
<222> LOCATION: (1)..(318)

<400> SEQUENCE: 34 caa att gtt ctc acc cag tct cca gca ctc atg tct gca tct cca ggg        48
Gln Ile Val Leu Thr Gln Ser Pro Ala Leu Met Ser Ala Ser Pro Gly
1               5                   10                  15 gtg aaa gtc acc atg acc tgc agt gcc aac tca agt gta agt tac atg        96
Val Lys Val Thr Met Thr Cys Ser Ala Asn Ser Ser Val Ser Tyr Met
            20                  25                  30 tat tgg tat cgg cag aag cca aga tcc tcc ccc aaa ccc tgg att tat       144
Tyr Trp Tyr Arg Gln Lys Pro Arg Ser Ser Pro Lys Pro Trp Ile Tyr
        35                  40                  45 ctc aca tcc aac ctg gct tct gga gtc cct gct cgc ttc agt ggc agt       192
Leu Thr Ser Asn Leu Ala Ser Gly Val Pro Ala Arg Phe Ser Gly Ser
    50                  55                  60 ggg tct ggg acc tct tat tct ctc aca atc agc agc atg gag gct gaa       240
Gly Ser Gly Thr Ser Tyr Ser Leu Thr Ile Ser Ser Met Glu Ala Glu
65                  70                  75                  80 gat gct gcc act tat tac tgc cag cag tgg agt agt aac cca ccc acg       288
Asp Ala Ala Thr Tyr Tyr Cys Gln Gln Trp Ser Ser Asn Pro Pro Thr
                85                  90                  95 ttc ggc tcg ggg aca aag ttg gaa ata aaa                               318
Phe Gly Ser Gly Thr Lys Leu Glu Ile Lys
            100                 105

<210> SEQ ID NO 35
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(360)

<400> SEQUENCE: 35 gag gtg cag ctg gtg gag tct ggg gga gac tta gtg aag cct gga ggg        48
Glu Val Gln Leu Val Glu Ser Gly Gly Asp Leu Val Lys Pro Gly Gly
1               5                   10                  15 tcc ctg aaa ctc tcc tgt gca gcc tct gga ttc act ttc agt ttc tat        96
Ser Leu Lys Leu Ser Cys Ala Ala Ser Gly Phe Thr Phe Ser Phe Tyr
            20                  25                  30 ggc atg tct tgg gtt cgc cag act cca gac aag agg ctg gag tgg gtc       144
Gly Met Ser Trp Val Arg Gln Thr Pro Asp Lys Arg Leu Glu Trp Val
        35                  40                  45 gca acc ttt agt ggt ggt ggt aat tac acc tac tat cca gac agt gtg       192
Ala Thr Phe Ser Gly Gly Gly Asn Tyr Thr Tyr Tyr Pro Asp Ser Val
    50                  55                  60 aag ggg cga ttc acc atc tcc aga gac aat gcc aag aac acc ctt tac       240
Lys Gly Arg Phe Thr Ile Ser Arg Asp Asn Ala Lys Asn Thr Leu Tyr
65                  70                  75                  80 ctc caa atg agc agt ctg aag tct gag gac aca gcc agg tat tac tgt       288
Leu Gln Met Ser Ser Leu Lys Ser Glu Asp Thr Ala Arg Tyr Tyr Cys
                85                  90                  95 gca aga cat ggg ggg tta cca ttt tat gct atg gac tac tgg ggt caa       336
Ala Arg His Gly Gly Leu Pro Phe Tyr Ala Met Asp Tyr Trp Gly Gln
            100                 105                 110 gga acc tca gtc acc gtc tcc tca                                        360
```

```
Gly Thr Ser Val Thr Val Ser Ser
        115                 120
```

<210> SEQ ID NO 36
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(324)

<400> SEQUENCE: 36

```
gaa att gtg atc acc cag tct cca gca ctc atg gct gca tct cca ggg      48
Glu Ile Val Ile Thr Gln Ser Pro Ala Leu Met Ala Ala Ser Pro Gly
1               5                   10                  15 gag aag gtc acc atc acc tgc agt gtc tcc tca agt ata agt tcc agc      96
Glu Lys Val Thr Ile Thr Cys Ser Val Ser Ser Ser Ile Ser Ser Ser
            20                  25                  30 aac ttg cac tgg tac cag cag aag tca gaa acc tcc ccc aaa ccc tgg     144
Asn Leu His Trp Tyr Gln Gln Lys Ser Glu Thr Ser Pro Lys Pro Trp
        35                  40                  45 att tat ggc aca ttt aac ctg gct tct gga gtc cct gtt cgc ttc agt     192
Ile Tyr Gly Thr Phe Asn Leu Ala Ser Gly Val Pro Val Arg Phe Ser
    50                  55                  60 ggc agt gga tct ggg acc tct tat tct ctc aca atc agc agc atg gag     240
Gly Ser Gly Ser Gly Thr Ser Tyr Ser Leu Thr Ile Ser Ser Met Glu
65                  70                  75                  80 gct gaa gat gct gcc act tat tac tgt caa cag tgg agt agt cac cca     288
Ala Glu Asp Ala Ala Thr Tyr Tyr Cys Gln Gln Trp Ser Ser His Pro
                85                  90                  95 ttc acg ttc ggc tcg ggg aca aag ttg gaa ata aaa                     324
Phe Thr Phe Gly Ser Gly Thr Lys Leu Glu Ile Lys
            100                 105
```

<210> SEQ ID NO 37
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(360)

<400> SEQUENCE: 37

```
gaa gtg cag ctg gtg gag tct ggg ggg ggc ttt gtg aag cct gga ggg      48
Glu Val Gln Leu Val Glu Ser Gly Gly Gly Phe Val Lys Pro Gly Gly
1               5                   10                  15 tcc ctg aaa ctc tcc tgt gca gcc tct gga ttc tct ttc agt gac tat      96
Ser Leu Lys Leu Ser Cys Ala Ala Ser Gly Phe Ser Phe Ser Asp Tyr
            20                  25                  30 tac ttg tat tgg gtt cgc cag act ccg gaa aaa agg ctg gag tgg gtc     144
Tyr Leu Tyr Trp Val Arg Gln Thr Pro Glu Lys Arg Leu Glu Trp Val
        35                  40                  45 gca acc att agt gtt ggt ggt ggt aac acc tcc tat ccg gac agt gtg     192
Ala Thr Ile Ser Val Gly Gly Gly Asn Thr Ser Tyr Pro Asp Ser Val
    50                  55                  60 aag ggg cga ttc acc atc tcc aga gac aat gcc aag aac aac ctg tac     240
Lys Gly Arg Phe Thr Ile Ser Arg Asp Asn Ala Lys Asn Asn Leu Tyr
65                  70                  75                  80
```

```
ctg caa atg agc agt ctg aag tct gag gac aca gcc atg tat tac tgt      288
Leu Gln Met Ser Ser Leu Lys Ser Glu Asp Thr Ala Met Tyr Tyr Cys
            85                  90                  95 aca agg ggc ctt tac tac ggc ccg gcc tgg ttt gct tac tgg ggc caa      336
Thr Arg Gly Leu Tyr Tyr Gly Pro Ala Trp Phe Ala Tyr Trp Gly Gln
        100                 105                 110 ggg act ctg gtc act gtc tct gca                                      360
Gly Thr Leu Val Thr Val Ser Ala
        115                 120

<210> SEQ ID NO 38
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(339)

<400> SEQUENCE: 38 gac att gtg atg aca cag tct cca tcc tcc ctg gct atg tca gta gga       48
Asp Ile Val Met Thr Gln Ser Pro Ser Ser Leu Ala Met Ser Val Gly
1               5                   10                  15 cag aag gtc act atg agc tgc aag tcc agt cag agc ctt tta aat agt       96
Gln Lys Val Thr Met Ser Cys Lys Ser Ser Gln Ser Leu Leu Asn Ser
            20                  25                  30 agc aat caa aag aac tat ttg gcc tgg ttc cag cag aca cca gga cag      144
Ser Asn Gln Lys Asn Tyr Leu Ala Trp Phe Gln Gln Thr Pro Gly Gln
        35                  40                  45 tct cct aaa ctt ctg gta tac ttt gca tcc act agg gaa tct ggg gtc      192
Ser Pro Lys Leu Leu Val Tyr Phe Ala Ser Thr Arg Glu Ser Gly Val
    50                  55                  60 cct gat cgc ttc ata ggc agt ggt tct ggg aca gat ttc act ctt acc      240
Pro Asp Arg Phe Ile Gly Ser Gly Ser Gly Thr Asp Phe Thr Leu Thr
65                  70                  75                  80 atc agc agt gtg aag gct gag gac ctg gca gat tac ttc tgt cag caa      288
Ile Ser Ser Val Lys Ala Glu Asp Leu Ala Asp Tyr Phe Cys Gln Gln
                85                  90                  95 cat tat agc act ccg tgg acg ttc ggt gga ggc acc aag ctg gaa atc      336
His Tyr Ser Thr Pro Trp Thr Phe Gly Gly Gly Thr Lys Leu Glu Ile
            100                 105                 110 aga                                                                  339
Arg

<210> SEQ ID NO 39
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(324)

<400> SEQUENCE: 39 gac atc cag atg acc cag tct cca tcc tcc tta tct gcc tct ctg gga       48
Asp Ile Gln Met Thr Gln Ser Pro Ser Ser Leu Ser Ala Ser Leu Gly
1               5                   10                  15
```

| | | | | | | | | | | | | | | | | |
|---|---|---|---|---|---|---|---|---|---|---|---|---|---|---|---|---|
| gaa | aga | gtc | agt | ctc | act | tgt | cgg | gca | agt | cag | aaa | att | agt | ggt | tac | 96 |
| Glu | Arg | Val | Ser | Leu | Thr | Cys | Arg | Ala | Ser | Gln | Lys | Ile | Ser | Gly | Tyr | |
| | | | 20 | | | | | 25 | | | | | 30 | | | |
| tta | agc | tgg | ctt | cag | cag | aaa | cct | gat | gga | act | att | aag | cgc | ctc | atc | 144 |
| Leu | Ser | Trp | Leu | Gln | Gln | Lys | Pro | Asp | Gly | Thr | Ile | Lys | Arg | Leu | Ile | |
| | | 35 | | | | | 40 | | | | | 45 | | | | |
| tac | gcc | gca | tcc | act | tta | gat | tct | ggt | gtc | cca | aaa | agg | ttc | agt | ggc | 192 |
| Tyr | Ala | Ala | Ser | Thr | Leu | Asp | Ser | Gly | Val | Pro | Lys | Arg | Phe | Ser | Gly | |
| 50 | | | | | 55 | | | | | 60 | | | | | | |
| agt | agg | tct | ggg | tca | gat | tat | tct | ctc | acc | atc | agc | agc | ctt | gag | tct | 240 |
| Ser | Arg | Ser | Gly | Ser | Asp | Tyr | Ser | Leu | Thr | Ile | Ser | Ser | Leu | Glu | Ser | |
| 65 | | | | 70 | | | | | 75 | | | | | 80 | | |
| gaa | gat | ttt | gca | gac | tat | tac | tgt | cta | caa | tat | gct | agt | tct | ctc | atg | 288 |
| Glu | Asp | Phe | Ala | Asp | Tyr | Tyr | Cys | Leu | Gln | Tyr | Ala | Ser | Ser | Leu | Met | |
| | | | 85 | | | | | 90 | | | | | 95 | | | |
| tac | acg | ttc | gga | ggg | ggg | acc | aaa | ctg | gaa | ata | aag | | | | | 324 |
| Tyr | Thr | Phe | Gly | Gly | Gly | Thr | Lys | Leu | Glu | Ile | Lys | | | | | |
| | | 100 | | | | | 105 | | | | | | | | | |

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 40

Arg Arg Lys Arg Arg Arg
1               5

<210> SEQ ID NO 41
<211> LENGTH: 365
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 41
gaggtgcagt tggtggagtc tgggggagac ttggtgaagc ctggagggtc cctgaaactc      60
gcctgtgcag cctctggatt cattttcagt agccatggca tggcatgtct tgggttcgcc     120
agactccaga caagaggctg gagtgggtcg caaccattag cagtggtggt acttacacct     180
actatccaga cagtgtgaag gggcgattca ccatatccag agacaatgac aaaaacaccc     240
tgtacctgca aatgaacagt ctgaagtctg aggacacagc catgtattac tgtgcaagac     300
acgactttga ttacgacgcg gcctggtttg cttactgggg ccaagggact ctggtcactg     360
tctct                                                                 365

<210> SEQ ID NO 42
<211> LENGTH: 357
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 42
gaagtgcagc tggtggagtc tgggggggc tttgtgaagc ctggagggtc cctgaaactc       60
tcctgtgcag cctctggatt ctctttcagt gactattact gtattgggt tcgccagact     120 ccggaaaaaa ggctggagtg ggtcgcaacc attagtgttg gtggtggtaa cacctcctat     180

```
ccggacagtg tgaagggcg attcaccatc tccagagaca atgccaagaa caacctgtac    240
ctgcaaatga gcagtctgaa gtctgaggac acagccatgt attactgtac aagggcctt    300 tactacggcc cggcctggtt tgcttactgg ggccaaggga ctctggtcac tgtctct       357
```

ANTI-CEACAM1 RECOMBINANT ANTIBODIES FOR CANCER THERAPY

CROSS REFERENCE TO RELATED APPLICATIONS

This application is a 35 U.S.C. 371 National Stage Application of International Application No. PCT/US2012/067207 filed on Nov. 30, 3012, which designates the United States, and which claims the benefit under 35 U.S.C. §119(e) of U.S. Provisional Patent Application Ser. No. 61/565,640 filed on Dec. 1, 2011, the contents of each are incorporated herein in their entity by reference.

This invention was made with Government support under Grant Number DK051362 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Nov. 29, 2012, is named 43214714.txt and is 28,672 bytes in size.

FIELD OF THE INVENTION

This invention relates to recombinant monoclonal antibodies and antigen-binding portions thereof against CEACAM1, and their use as therapeutics in tumor cell cytolysis and rejection, as well as diagnostic agents and targeting agents for molecular imaging and targeted delivery of other therapeutic agents.

BACKGROUND

According to the most recent data from the World Health Organization, ten million people around the world were diagnosed with the cancer in 2000, and six million died from it. Moreover, statistics indicate that the cancer incidence rate is on the rise around the globe. In America, for example, projections suggest that forty percent of those alive today will be diagnosed with some form of cancer at some point in their lives. By 2010, that number will have climbed to fifty percent. Of all cancers, pancreatic cancer is the eleventh most common cancer and the fourth leading cause of cancer death in both men and women.

Modern technology, such as that involving the use of hybridomas, has made available to researchers and clinicians sources of highly specific and potent monoclonal antibodies useful in general diagnostic and clinical procedures. For example, there are now therapeutic antibodies for the treatment of cancer, such as HERCEPTIN® (trastuzumab, Genentech) for metastatic breast cancer and PANOREX® (endrecolomab, Centocor/GlaxoSmithKline) approved in Germany for the treatment of colorectal cancer.

SUMMARY OF THE INVENTION

Provided herein are recombinant monoclonal antibodies and antigen-binding portions thereof useful in inhibiting CEACAM1 in tumor cells. More specifically, provided herein are novel compositions, comprising recombinant anti-CEACAM1-binding antibodies and peptides, and methods of their use in anti-tumor proliferation and invasiveness therapies, such as the treatment of cancer, particularly pancreatic cancer. In addition, the compositions comprising the anti-CECAM-binding peptides described herein are useful in assessment and imaging methods, such as companion diagnostics for determining CEACAM1 expression in tumor biopsies to identify likely responders for personalized medicine approaches, CEACAM1-targeted molecular imaging, which can be used, for example, in serial monitoring of response(s) to therapy, and in vivo detection of tumors. Further, such diagnostics provide novel approaches for anti-cancer therapies for use in personalized medicine applications. Furthermore, the compositions comprising the anti-CEACAM1-binding peptides described herein are useful as targeting moieties for other diagnostic and therapeutic compositions, in combination with delivery agents such as nanoparticles, polyplexes, microparticles, etc. Such anti-CEACAM1-binding peptides can also be called CEACAM1 antagonists.

Accordingly, provided herein in some aspects are isolated CEACAM1-specific recombinant monoclonal antibodies or antigen-binding portions thereof that bind the antigen recognized by the monoclonal antibodies 5F4, 34B1, or 26H7 comprising: at least one light chain component and at least one heavy chain component. In some embodiments of these aspects, the at least one heavy chain component comprises the amino acids of SEQ ID NO:26, SEQ ID NO:28, or SEQ ID NO:30 and the at least one light chain component comprises the amino acids of SEQ ID NO:27, SEQ ID NO:29, SEQ ID NO:31 or SEQ ID NO:32.

In some embodiments of these aspects and all such aspects described herein, the anti-CEACAM1-specific recombinant monoclonal antibody is a humanized antibody or portion thereof.

In some embodiments of these aspects and all such aspects described herein, the anti-CEACAM1-specific recombinant monoclonal antibody is a chimeric antibody comprising the variable regions of the heavy and light chains of the isolated CEACAM1-specific recombinant antibody linked to the human immunoglobulin gamma-1 and kappa constant regions, respectively.

In some aspects, provided herein are isolated recombinant antibodies or antigen-binding portions thereof comprising: a heavy chain complementarity determining region (CDR) 1 consisting of the amino acid residues SSHGMS (SEQ ID NO:1), a heavy chain CDR2 consisting of the amino acid residues TISSGGTYTYYPDSVKG (SEQ ID NO:2), a heavy chain CDR3 consisting of the amino acid residues HDFDYDAAWFAY (SEQ ID NO:3), a light chain CDR1 consisting of the amino acid residues SANSSVSYMY (SEQ ID NO:4), a light chain CDR2 consisting of the amino acid residues LTSNLAS (SEQ ID NO:5), and a light chain CDR3 consisting of the amino acid residues QQWSSNPPT (SEQ ID NO:6), such that the isolated recombinant antibody or antigen-binding portion thereof binds the antigen recognized by 5F4.

In some aspects, provided herein are isolated recombinant antibodies or antigen-binding portions thereof comprising: a heavy chain complementarity determining region (CDR) 1 consisting of the amino acid residues SSHGMS (SEQ ID NO:1), SFYGMS (SEQ ID NO:7), or SDYYLY (SEQ ID NO:13); a heavy chain CDR2 consisting of the amino acid residues TISSGGTYTYYPDSVKG (SEQ ID NO:2), TFSGGGNYTYYPDSVKG (SEQ ID NO:8) or TISVGGGNTSYPDSVKG (SEQ ID NO:14); a heavy chain CDR3 consisting of the amino acid residues HDFDYDAAWFAY (SEQ ID NO:3), or HGGLPFYAMDY (SEQ ID NO:9), or GLTTGPAWFAY (SEQ ID NO:15); a light chain CDR1 consisting of the amino acid residues SANSSV- SYMY (SEQ ID NO:4), SVSSSISSSNLH (SEQ ID NO:10), KSSQSLLNSSNQKNYLA (SEQ ID NO:16), or RASQKISGYLS (SEQ ID NO:19); a light chain CDR2 consisting of the amino acid residues LTSNLAS (SEQ ID NO:5), SVSSSISSSNLH (SEQ ID NO:10), FASTRES (SEQ ID NO:17), or AASTLDS (SEQ ID NO:20); and a light chain CDR3 consisting of the amino acid residues QQWSSNPPT (SEQ ID NO:6), QQWSSHPFT (SEQ ID NO:12), QQHYSTPWT (SEQ ID NO:18) or LQYASSLMYT (SEQ ID NO:21); such that the isolated recombinant antibodies or antigen-binding portions thereof bind the antigen recognized by the antibodies termed herein as 5F4, 34B1, or 26H7.

In some embodiments of these aspects and all such aspects described herein, the antibody portion is a Fab fragment, a Fab' fragment, a Fd fragment, a Fd' fragment, a Fv fragment, a dAb fragment, a $F(ab')_2$ fragment, a single chain fragment, a diabody, or a linear antibody.

Provided herein, in some aspects, are diagnostic kits comprising any of the isolated CEACAM1-specific recombinant monoclonal antibodies or antigen-binding portions thereof, humanized antibodies, and/or chimeric antibodies described herein.

Provided herein, in some aspects, are compositions comprising any of the isolated CEACAM1-specific recombinant monoclonal antibodies or antigen-binding portions thereof, humanized antibodies, and/or chimeric antibodies described herein and a carrier.

In some embodiments of theses aspects and all such aspects described herein, the isolated CEACAM1-specific recombinant monoclonal antibodies or antigen-binding portions thereof, humanized antibodies, and/or chimeric antibodies are linked to a label.

In some embodiments of theses aspects and all such aspects described herein, the isolated CEACAM1-specific recombinant monoclonal antibodies or antigen-binding portions thereof, humanized antibodies, and/or chimeric antibodies further comprise an agent conjugated to the anti-CEACAM1 recombinant antibody or portion thereof, humanized antibody, and/or chimeric antibody to form an immunoconjugate specific for CEACAM1. In some such embodiments, the agent conjugated to the antibody or antibody fragment thereof is a chemotherapeutic agent, a toxin, a radioactive isotope, a small molecule, an siRNA, a nanoparticle, or a microbubble.

Provided herein, in some aspects, are pharmaceutical compositions comprising the recombinant anti-CEACAM1 antibody or portion thereof, humanized antibody, and/or chimeric antibody that specifically binds to CEACAM1, and a pharmaceutically acceptable carrier.

In some aspects, provided herein are methods of treating pancreatic cancer, the methods comprising administering to a subject in need thereof a therapeutically effective amount of a pharmaceutical composition comprising a recombinant anti-CEACAM1 antibody or portion thereof, humanized antibody, and/or chimeric antibody that specifically binds to CEACAM1, and a pharmaceutically acceptable carrier.

In some aspects, provided herein are methods of inhibiting tumor cell invasiveness in a subject having a cancer or a tumor, the methods comprising administering to a subject in need thereof a therapeutically effective amount of a pharmaceutical composition comprising a recombinant anti-CEACAM1 antibody or portion thereof, humanized antibody, and/or chimeric antibody that specifically binds to CEACAM1, and a pharmaceutically acceptable carrier.

In some embodiments of these methods and all such methods described herein, the methods further comprise administering one or more chemotherapeutic agents, angiogenesis inhibitors, cytotoxic agents, and/or anti-proliferative agents.

Provided herein, in some aspects, are methods of inhibiting tumor growth and reducing tumor size or tumor metastasis in a subject in need thereof by inhibiting CEACAM1 expression and/or function in a cell, the methods comprising administering to a subject in need thereof a therapeutically effective amount of a pharmaceutical composition comprising a recombinant anti-CEACAM1 antibody or portion thereof, humanized antibody, and/or chimeric antibody that specifically binds to CEACAM1, and a pharmaceutically acceptable carrier.

In some aspects, provided herein are method of inhibiting cancer progression by inhibiting CEACAM1 expression and/or function in a tumor cell, the method comprising administering to a subject in need thereof a therapeutically effective amount of a pharmaceutical composition comprising a recombinant anti-CEACAM1 antibody or portion thereof, humanized antibody, and/or chimeric antibody that specifically binds to CEACAM1, and a pharmaceutically acceptable carrier.

Also provided herein, in some aspects, are methods for combining CEACAM1-targeted molecular imaging and CEACAM1-targeted delivery of a therapeutic agent, the methods comprising administering to a subject an effective amount of a therapeutic agent and a pharmaceutical composition comprising a recombinant anti-CEACAM1 antibody or portion thereof, humanized antibody, and/or chimeric antibody that specifically binds to CEACAM1 conjugated to a targeting moiety, and a pharmaceutically acceptable carrier, and determining the presence or absence of the pharmaceutical composition conjugated to the targeting moiety using molecular imaging.

In some embodiments of these aspects and all such aspects described herein, the therapeutic agent is a chemotherapeutic agent, a small molecule, a peptide, or an aptamer.

In some aspects, provided herein are pharmaceutical compositions comprising a recombinant anti-CEACAM1 antibody or portion thereof, humanized antibody, and/or chimeric antibody that specifically binds to CEACAM1 for use in inhibiting tumor cell invasiveness in a subject having pancreatic cancer or a pancreatic tumor.

In some embodiments of these aspects and all such aspects described herein, the use further comprises one or more chemotherapeutic agents, angiogenesis inhibitors, cytotoxic agents, and/or anti-proliferative agents. In some such embodiments, the therapeutic agent is a chemotherapeutic agent, a small molecule, a peptide, and/or an aptamer.

In some aspects, provided herein are pharmaceutical composition comprising a recombinant anti-CEACAM1 antibody or portion thereof, humanized antibody, and/or chimeric antibody that specifically binds to CEACAM1 for use in inhibiting tumor growth and reducing tumor size or tumor metastasis by inhibiting CEACAM1 expression and/or function in a cell in a subject in need thereof.

In some aspects, provided herein are isolated oligonucleotides comprising nucleotides of the sequence of SEQ ID NO:33, wherein said oligonucleotide encodes the variable regions of the heavy chain of the 5F4 antibody.

In some aspects, provided herein are isolated oligonucleotides comprising nucleotides of the sequence of SEQ ID NO:34, wherein said oligonucleotide encodes the variable regions of the light chain of the 5F4 antibody.

In some embodiments of these aspects and all such aspects described herein, the isolated oligonucleotides comprise part of an isolated expression vector.

In some embodiments of these aspects and all such aspects described herein, the isolated expression vector comprises or is part of an isolated host cell or isolated host cell population.

DEFINITIONS

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The term "antibody" is used in the broadest sense and includes monoclonal antibodies (including full length or intact monoclonal antibodies), polyclonal antibodies, multivalent antibodies, multispecific antibodies (e.g., bispecific antibodies), antibody fragments, and antigen-binding portions thereof (e.g., paratopes, CDRs), so long as they exhibit the desired biological activity and specificity. In the context of binding specific CEACAM1 epitopes, the terms antibody and CEACAM1-binding peptides may be used interchangeably to refer to the portion of the specific anti-CEACAM1 antibodies described herein that bind selectively to the CEACAM1 epitope.

As used herein, the term "Complementarity Determining Regions" (CDRs, i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region can comprise amino acid residues from a "complementarity determining region" as defined by Kabat (i.e., about residues 24-34 (L1), 50-56 (L2) and 89-97 (L3) in the light chain variable domain and 31-35 (H1), 50-65 (H2) and 95-102 (H3) in the heavy chain variable domain (Kabat et al., Sequences of Proteins of Immunological Interest, 5th Ed. Public Health Service, National Institutes of Health, Bethesda, Md. (1987, 1991)), and/or those residues from a "hypervariable loop" (i.e., about residues 26-32 (L1), 50-52 (L2) and 91-96 (L3) in the light chain variable domain and 26-32 (H1), 53-55 (H2) and 96-101 (H3) in the heavy chain variable domain (Chothia & Lesk 196 J. Mol. Biol. 901 (1987)). In some instances, a complementarity determining region can include amino acids from both a CDR region defined according to Kabat and a hypervariable loop.

As used herein, "antibody variable domain" refers to the portions of the light and heavy chains of antibody molecules that include amino acid sequences of Complementarity Determining Regions (CDRs; i.e., CDR1, CDR2, and CDR3), and Framework Regions (FRs). VH refers to the variable domain of the heavy chain. VL refers to the variable domain of the light chain. According to the methods used in this invention, the amino acid positions assigned to CDRs and FRs can be defined according to Kabat. Amino acid numbering of antibodies or antigen binding fragments is also according to that of Kabat.

The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. For example, the monoclonal antibodies to be used in accordance with the invention can be made by the hybridoma method first described by Kohler et al., 256 Nature 495 (1975), or can be made by recombinant DNA methods (see, e.g., U.S. Pat. No. 7,829,678, U.S. Pat. No. 7,314,622). The "monoclonal antibodies" can also be isolated from phage antibody libraries using the techniques described in Clackson et al., 352 Nature 624 (1991) or Marks et al., 222 J. Mol. Biol. 581 (1991), for example. A monoclonal antibody can be of any species, including, but not limited to, mouse, rat, goat, sheep, rabbit, and human monoclonal antibodies.

The term "antibody fragment" as used herein, refers to a protein fragment that comprises only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., 341 Nature 3544 (1989)) which consists of a VH domain; (vii) isolated CDR regions; (viii) F(ab')$_2$ fragments, a bivalent fragment including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen binding sites, comprising a heavy chain variable domain (VH) connected to a light chain variable domain (VL) in the same polypeptide chain (see, e.g., EP 404,097; WO 93/11161; Hollinger et al., 90 PNAS 6444 (1993)); (xi) "linear antibodies" comprising a pair of tandem Fd segments (VH-CH1-VH-CH1) which, together with complementary light chain polypeptides, form a pair of antigen binding regions (Zapata et al., 8 Protein Engin. 1057 (1995); and U.S. Pat. No. 5,641,870).

"Framework regions" (FR) are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25

(LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

The term "specificity" refers to the number of different types of antigens or antigenic determinants to which an antibody or antibody fragment thereof as described herein can bind. The specificity of an antibody or antibody fragment thereof can be determined based on affinity and/or avidity. The affinity, represented by the equilibrium constant for the dissociation (KD) of an antigen with an antigen-binding protein, is a measure of the binding strength between an antigenic determinant and an antigen-binding site on the antigen-binding protein, such as an antibody or antibody fragment thereof: the lesser the value of the KD, the stronger the binding strength between an antigenic determinant and the antigen-binding molecule. Alternatively, the affinity can also be expressed as the affinity constant (KA), which is 1/KD. As will be clear to the skilled person, affinity can be determined in a manner known per se, depending on the specific antigen of interest. Accordingly, an antibody or antibody fragment thereof as defined herein is said to be "specific for" a first target or antigen compared to a second target or antigen when it binds to the first antigen with an affinity (as described above, and suitably expressed, for example as a KD value) that is at least 10 times, such as at least 100 times, and preferably at least 1000 times, and up to 10000 times or more better than the affinity with which said amino acid sequence or polypeptide binds to another target or polypeptide.

Antibody affinities can be determined, for example, by a surface plasmon resonance based assay (such as the BIA-CORE assay described in PCT Application Publication No. WO2005/012359); enzyme-linked immunoabsorbent assay (ELISA); and competition assays (e.g., RIA's), for example. In certain aspects described herein, an anti-CEACAM1 antibody can be used as a therapeutic agent in targeting and interfering with diseases or conditions where CEACAM1 activity is involved. Also, the anti-CEACAM1 antibody can be subjected to other biological activity assays, e.g., in order to evaluate its effectiveness as a therapeutic, or its effectiveness as a diagnostic aid, etc. Such assays are known in the art and depend on the target antigen and intended use for the antibody. Examples include the HUVEC inhibition assay; tumor cell growth inhibition assays (see e.g., WO 89/06692); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). Other biological activity assays that can be used to assess an anti-CEACAM1 antibody are described herein.

"Avidity" is the measure of the strength of binding between an antigen-binding molecule (such as an antibody or antibody fragment thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody or portion of an antibody as described herein) will bind to their cognate or specific antigen with a dissociation constant (KD of $10^{-5}$ to $10^{-12}$ moles/liter or less, such as $10^{-7}$ to $10^{-12}$ moles/liter or less, or $10^{-8}$ to $10^{-12}$ moles/liter (i.e., with an association constant (KA) of $10^5$ to $10^{12}$ liter/moles or more, such as $10^7$ to $10^{12}$ liter/moles or $10^8$ to $10^{12}$ liter/moles). Any KD value greater than $10^{-4}$ mol/liter (or any KA value lower than $10^4$ $M^{-1}$) is generally considered to indicate non-specific binding. The KD for biological interactions which are considered meaningful (e.g., specific) are typically in the range of $10^{-10}$ M (0.1 nM) to $10^{-5}$ M (10000 nM). The stronger an interaction, the lower is its KD. For example, a binding site on an antibody or portion thereof described herein will bind to the desired antigen with an affinity less than 500 nM, such as less than 200 nM, or less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of an anti-CEACM1-binding peptide (e.g., a recombinant antibody or portion thereof) described herein to bind to a target, such as a molecule present on the cell-surface, with a KD $10^{-5}$ M (10000 nM) or less, e.g., $10^{-6}$ M, $10^{-7}$ M, $10^{-8}$ M, $10^{-9}$ M, $10^{40}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay.

As used herein, the term "target" refers to a biological molecule (e.g., peptide, polypeptide, protein, lipid, carbohydrate) to which a polypeptide domain which has a binding site can selectively bind. The target can be, for example, an intracellular target (e.g., an intracellular protein target) a cell surface target (e.g., a membrane protein, a receptor protein), such as a cell surface protein.

As described herein, an "antigen" is a molecule that is bound by a binding site on a polypeptide agent, such as an antibody or antibody fragment thereof. Typically, antigens are bound by antibody ligands and are capable of raising an antibody response in vivo. An antigen can be a polypeptide, protein, nucleic acid or other molecule. In the case of conventional antibodies and fragments thereof, the antibody binding site as defined by the variable loops (L1, L2, L3 and H1, H2, H3) is capable of binding to the antigen. The term "antigenic determinant" refers to an epitope on the antigen recognized by an antigen-binding molecule, and more particularly, by the antigen-binding site of said molecule.

As used herein, an "epitope" can be formed both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein.

"Humanized" forms of non-human (e.g., murine) antibodies are chimeric antibodies that are engineered or designed to comprise minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. See Jones et al., 321 Nature 522 (1986); Riechmann et al., 332 Nature 323 (1988); Presta, 2 Curr. Op. Struct. Biol. 593 (1992). As used herein, a "composite human antibody" is a specific type of engineered or humanized antibody.

A "human antibody," "non-engineered human antibody," or "fully human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies. Vaughan et al., 14 Nature Biotechnol. 309 (1996); Sheets et al., 95 PNAS 6157 (1998); Hoogenboom & Winter, 227 J. Mol. Biol. 381 (1991); Marks et al., 222 J. Mol. Biol., 581 (1991).

Human antibodies can also be made by introducing human immunoglobulin loci into transgenic animals, e.g., mice in which the endogenous mouse immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. No. 5,545,807; U.S. Pat. No. 5,545,806; U.S. Pat. No. 5,569,825; U.S. Pat. No. 5,625,126; U.S. Pat. No. 5,633,425; U.S. Pat. No. 5,661,016; Marks et al., 10 Bio/Technology 779 (1992); Lonberg et al., 368 Nature 856 (1994); Morrison, 368 Nature 812 (1994); Fishwild et al., 14 Nat. Biotechnol. 845 (1996); Neuberger, 14 Nat. Biotechnol. 826 (1996); Lonberg & Huszar, 13 Intl. Rev. Immunol. 65 (1995). Alternatively, the human antibody can be prepared via immortalization of human B lymphocytes producing an antibody directed against a target antigen (such B lymphocytes can be recovered from an individual or can have been immunized in vitro). See, e.g., Cole et al., Monoclonal Antibodies & Cancer Therapy 77 (Alan R. Liss, 1985); Boerner et al., 147 J. Immunol., 86 (1991); U.S. Pat. No. 5,750,373.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al., 1992, describes affinity maturation by VH and VL domain shuffling. Random mutagenesis of CDR and/or framework residues is described by: Barbas et al., 91 PNAS 3809 (1994); Schier et al., 169 Gene 147 (1995); Yelton et al., 155 J. Immunol. 1994 (1995); Jackson et al., 154 J. Immunol. 3310 (1995); Hawkins et al., 226 J. Mol. Biol. 889 (1992).

A "functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. In order to screen for antibodies which bind to an epitope on an antigen bound by an antibody of interest, a routine cross-blocking assay such as that described in Antibodies, A Laboratory Manual, (Harlow & Lane, Cold Spring Harbor Lab., 1988), can be performed. Moreover, the antigen binding affinity of each of the antigen binding sites of a multivalent antibody herein need not be quantitatively the same. For multimeric antibodies, the number of functional antigen binding sites can be evaluated using ultracentrifugation analysis as described in Example 2 of U.S. Patent Appl. Pub. No. 2005/0186208. According to this method of analysis, different ratios of target antigen to multimeric antibody are combined and the average molecular weight of the complexes is calculated assuming differing numbers of functional binding sites. These theoretical values are compared to the actual experimental values obtained in order to evaluate the number of functional binding sites.

As used herein, a "blocking" antibody or an antibody "antagonist" is one that inhibits or reduces biological activity of the antigen to which it binds. For example, in some embodiments, a CEACAM1-specific antagonist antibody binds CEACAM1 and inhibits tumor cell-associated activity of CEACAM1.

Unless indicated otherwise, the expression "multivalent antibody"" is used throughout this specification to denote an antibody comprising three or more antigen binding sites. For example, the multivalent antibody is engineered to have the three or more antigen binding sites and is generally not a native sequence IgM or IgA antibody.

An antibody having a "biological characteristic" of a designated antibody is one which possesses one or more of the biological characteristics of that antibody which distinguish it from other antibodies that bind to the same antigen.

As used herein, "antibody mutant" or "antibody variant" refers to an amino acid sequence variant of the species-dependent antibody wherein one or more of the amino acid residues of the species-dependent antibody have been modified. Such mutants necessarily have less than 100% sequence identity or similarity with the species-dependent antibody. In one embodiment, the antibody mutant will have an amino acid sequence having at least 75% amino acid sequence identity or similarity with the amino acid sequence of either the heavy or light chain variable domain of the species-dependent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e., same residue) or similar (i.e., amino acid residue from the same group based on common side-chain properties, see below) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

To increase the half-life of the antibodies or polypeptide containing the amino acid sequences described herein, one can attach a salvage receptor binding epitope to the antibody (especially an antibody fragment), as described, e.g., in U.S. Pat. No. 5,739,277. For example, a nucleic acid molecule encoding the salvage receptor binding epitope can be linked in frame to a nucleic acid encoding a polypeptide sequence described herein so that the fusion protein expressed by the engineered nucleic acid molecule comprises the salvage receptor binding epitope and a polypeptide sequence described herein. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule (e.g., Ghetie et al., 18 Ann. Rev. Immunol. 739 (2000). Antibodies with substitutions in an Fc region thereof and increased serum half-lives are also described in WO 00/42072, WO 02/060919; Shields et al., 276 J. Biol. Chem. 6591 (2001); Hinton, 279 J. Biol. Chem. 6213-6216 (2004). In another embodiment, the serum half-life can also be increased, for example, by attaching other polypeptide sequences. For example, antibodies or other polypeptides useful in the methods of the invention can be attached to serum albumin or a portion of serum albumin that binds to the FcRn receptor or a serum albumin binding peptide so that serum albumin binds to the antibody or polypeptide, e.g., such polypeptide sequences are disclosed in WO 01/45746. In one embodiment, the half-life of a Fab is increased by these methods. See also, Dennis et al., 277 J. Biol. Chem. 35035 (2002), for additional serum albumin binding peptide sequences.

An "isolated" antibody is one that has been identified and separated and/or recovered from a component of its natural environment. Contaminant components of its natural environment are materials that would interfere with diagnostic or therapeutic uses for the antibody, and can include enzymes, hormones, and other proteinaceous or nonproteinaceous solutes. In certain embodiments, the antibody will be purified (1) to greater than 95% by weight of antibody as determined by, for example, the Lowry method, or more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, silver stain. Isolated antibody includes the antibody in situ within recombinant cells since at least one component of the antibody's natural environment will not be present. Ordinarily, however, isolated antibody will be prepared by at least one purification step.

By "portion" of a polypeptide, such as an antibody, antibody fragment thereof or antigen-binding peptide, or nucleic acid molecule that contains at least 10%, 20%, 30%, 40%, 50%, 60%, 70%, 80%, 90%, 95%, or more of the entire length of the reference nucleic acid molecule or polypeptide. A portion can contain 9, 10, 20, 30, 40, 50, 60, 70, 80, 90, or 100, 200, 300, 400, 500, 600, or more nucleotides, inclusive; or 3, 4, 5, 6, 7, 8, 9, 10, 20, 30, 40, 50, 60, 70, 80, 90, 100, 120, 140, 160, 180, 190, 200 amino acids or more, inclusive.

The term "anti-cancer therapy" refers to a therapy useful in treating cancer. Examples of anti-cancer therapeutic agents include, but are not limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaII (see, e.g., Agnew, 33 Chem. Intl. Ed. Engl. 183 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK☐ polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE☐ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB®); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3 dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

A "growth inhibitory agent" as used herein refers to a compound or composition which inhibits growth of a cell in vitro and/or in vivo. Thus, the growth inhibitory agent can be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Murakami et al., *Cell cycle regulation, oncogenes, & antineoplastic drugs*, in MOLECULAR BASIS OF CANCER (Mendelsohn & Israel, eds., WB Saunders, Philadelphia, 1995).

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, 14 Biochem. Socy. Transactions 375, 615th Meeting Belfast (1986); Stella et al., *Prodrugs: Chem. Approach to Targeted Drug Deliv.*, in DIRECTED DRUG DELIVERY, (Borchardt et al., (ed.), Humana Press, 1985). The prodrugs described herein include, but are not limited to, phosphate-containing prodrugs, thiophosphate-containing prodrugs, sulfate-containing prodrugs, peptide-containing prodrugs, D-amino acid-modified prodrugs, glycosylated prodrugs, .beta.-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

By "reduce or inhibit" is meant the ability to cause an overall decrease of about 20% or greater, 30% or greater, 40% or greater, 45% or greater, 50% or greater, of 55% or greater, of 60% or greater, of 65% or greater, of 70% or greater, or 75%, 80%, 85%, 90%, 95%, or greater. Reduce or inhibit can refer to, for example, the symptoms of the disorder being treated, the presence or size of metastases or micrometastases, the size of the primary tumor, the presence or the size of the dormant tumor.

The term "intravenous infusion" refers to introduction of a drug into the vein of an animal or human subject over a period of time greater than approximately 5 minutes, such as between approximately 30 to 90 minutes, although, according to the invention, intravenous infusion is alternatively administered for 10 hours or less. The term "intravenous bolus" or "intravenous push" refers to drug administration into a vein of an animal or human such that the body receives the drug in approximately 15 minutes or less, such as 5 minutes or less.

The term "subcutaneous administration" refers to introduction of a drug under the skin of an animal or human subject, preferable within a pocket between the skin and underlying tissue, by relatively slow, sustained delivery from a drug receptacle. The pocket can be created by pinching or drawing the skin up and away from underlying tissue.

The term "subcutaneous infusion" refers to introduction of a drug under the skin of an animal or human subject, preferably within a pocket between the skin and underlying tissue, by relatively slow, sustained delivery from a drug receptacle for a period of time including, but not limited to, 30 minutes or less, or 90 minutes or less. Optionally, the infusion can be made by subcutaneous implantation of a drug delivery pump implanted under the skin of the animal or human subject, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human subject, where bolus drug delivery is less than approximately 15 minutes, such as less than 5 minutes, or even less than 60 seconds. Administration is preferably within a pocket between the skin and underlying tissue, where the pocket is created, for example, by pinching or drawing the skin up and away from underlying tissue.

A "disorder" is any condition that would benefit from treatment with, for example, an antibody described herein. This includes chronic and acute disorders or diseases including those pathological conditions which predispose the mammal to the disorder in question. Non-limiting examples of disorders to be treated herein include cancer, particularly pancreatic cancer.

The word "label" when used herein refers to a detectable compound or composition which is conjugated directly or indirectly to the polypeptide. The label can be itself be detectable (e.g., radioisotope labels or fluorescent labels) or, in the case of an enzymatic label, can catalyze chemical alteration of a substrate compound or composition which is detectable.

By "subject" is meant a mammal, including, but not limited to, a human or non-human mammal, such as a bovine, equine, canine, ovine, or feline, etc. Individuals and patients are also subjects herein.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A demonstrates water retention capability. Lungs are spongy lobes inside the chest. Water retention is one of the routine methods for demonstrating lung damage (e.g., inflammation, edema, congestion). To measure water retention, one of the five lobes from MOPC- and 5F4-treated animals were excised, weighed and maintained in a glass desiccation cabinet for 14-18 days. After desiccation the lungs were weighed again and the difference is shown as percent water loss. There is barely any water loss of the lungs in the 5F4 treated mice but considerable water loss in the MOPC-1 treated mice. FIG. 2B shows collapsed lung in MOPC treated animals (15 ml conical, right). Lungs posess air pockets. Damaged lungs often have loss of air and elasticity. Air within a normal lung results in increased buoyancy. To measure lung damage by buoyancy, four of the five lobes from the mouse anti-human CEACAM1 monoclonal antibody 5F4-(in this case, Nr. 216, left), and MOPC treated animals (in this case, Nr. 208, right) treated animals were excised, rinsed with distilled water and floated in PBS buffer for no less than 2 hours. Healthy lungs float (5F4 mouse anti-human CEACAM1 monoclonal treated) and the collapsed lungs (MOPC antibody treatment) sink.

FIGS. 4A-4D demonstrate that the 5F4 antibody described herein prevents AsPc-1 metastasis to the axillary lymph nodes after subcutaneous inoculation as described in FIG. 3. The data here show an analysis two weeks after subcutaneous inoculation. FACS analysis revealed the presence of human CEACAM1$^+$ cells in the axillary LNs of MOPC-treated mice but not in 5F4-treated mice as the 5F4 monoclonal antibody is specific for human CEACAM1 but does not recognize mouse CEACAM1 (n=3 per group) (FIGS. 4A and 4C). PCR analysis revealed detectable levels of human CEACAM1-L in the axillary LNs of MOPC-treated mice but not in 5F4-treated mice (n=2 per group) (FIGS. 4B and 4D). Sp, spleen. LN, axillary lymph node. MLN, mesenteric lymph nodes.

FIG. 5B) but not in those treated with 5F4 (0/7 mice; FIG. 5A). Hematoxylin and eosin staining of the nodules revealed the presence of AsPc-1 cells in mice treated with MOPC (25×, FIG. 5C and 100×, FIG. 5D). The quantification of these results is shown in FIG. 5E.

FIG. 12A shows specific staining for lymphatic vessels (Lymphatic vessel endothelial maker, Lyve-1) and invasive tumor cells (cytokeratin) identified after MOPC but not 5F4 treatment. Tumor cells were surrounded by newly generated lymphatic vessels (staining consistent with overlap between these two markers). FIG. 12B demonstrates that no specific staining for lymphatic vessels (Lymphatic vessel endothelial maker, Lyve-1) nor tumor cells (cytokeratin) was identified after 5F4 treatment.

FIG. 13A shows the pancreas of 5F4-treated animals. No specific staining for lymphatic vessels (Lymphatic vessel endothelial maker, Lyve-1) nor tumor cells (cytokeratin) was identifiable. FIG. 13B-13E show pancreas of MOPC-treated animals. Specific staining for lymphatic vessels (Lymphatic vessel endothelial maker, Lyve-1) and invasive tumor cells (cytokeratin) was identified. In FIGS. 13D and 13E, tumor cells were surrounded by newly generated lymphatic vessels.

FIG. 14 provides DNA (SEQ ID NO: 33) and amino acid (SEQ ID NO: 26) sequences of hybridoma 5F4/2C6/2H3 heavy chain.

FIG. 15 provides DNA (SEQ ID NO: 34) and amino acid (SEQ ID NO: 27) sequences of hybridoma 5F4/2C6/2H3 light chain.

FIG. 16 provides DNA (SEQ ID NO: 35) and amino acid (SEQ ID NO: 28) sequences of thybridoma 34B1/2E8/2E6 heavy chain.

FIG. 17 provides DNA (SEQ ID NO: 36) and amino acid (SEQ ID NO: 29) sequences of hybridoma 34B1/2E8/2E6 light chain.

FIG. 18 provides DNA (SEQ ID NO: 37) and amino acid (SEQ ID NO: 30) sequences of hybridoma 26H7/2H9/2E10 heavy chain.

FIG. 19 provides two sets of DNA (SEQ ID NOS 38 and 39, respectively, in order of appearance) and amino acid (SEQ ID NOS 31 and 32, respectively, in order of appearance) sequences of hybridoma 26H7/2H9/2E10 light chain.

DETAILED DESCRIPTION

Figure 1:
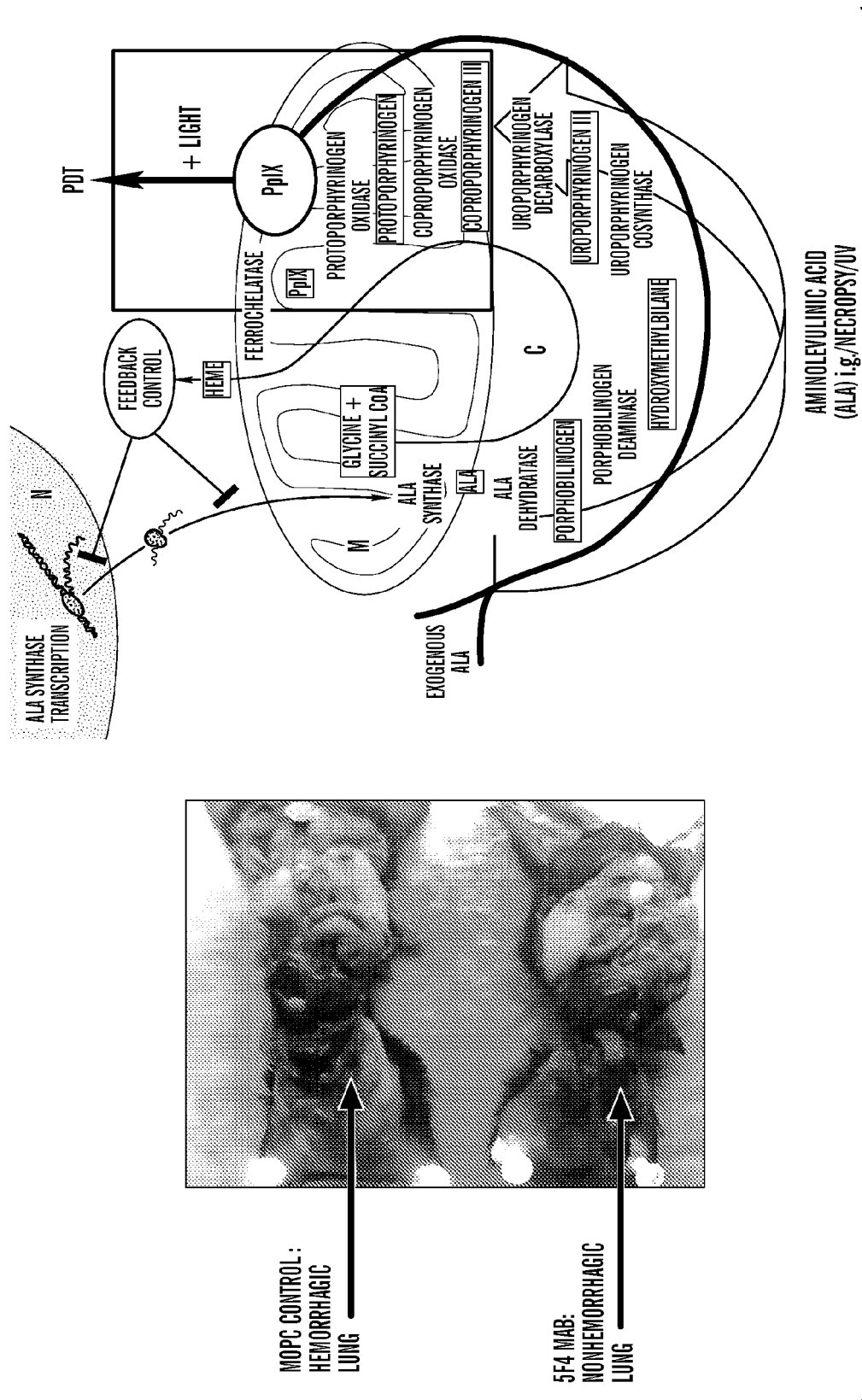
FIG. 1 demonstrates that 5F4 mouse anti-human CEACAM1 monoclonal antibody protects Rag2-deficient mice from human pancreatic cell line (AsPc-1) micrometastasis. Early detection of AsPc1 tumor cells with a noninvasive photosensitizaion method after intravenous injection is shown. The human pancreatic cancer cell line, AsPc-1 ($0.5 \times 10^6$ cells), was administered by tail-vein injection. After 14 days, animals received an oral dose of delta-aminolevulinic acid (ALA; 100 mg/kg) 4-6 hours prior to sacrifice by euthanasia and analysis of tissue fluorescence. Animals were then maintained under subdued light conditions to avoid photobleaching and phototoxic reactions. The abdominal and thoracic cavities of the animals were examined immediately under white light and then illuminated by UV light (405 nm) to evaluate the presence of tumors in the parenchyma of the lungs and the lymph nodes as evidence of metastasis. Note the hemorrhagic lung in the MOPC treated control (top) but normal, nonhemorrhagic appearing lung in the 5F4 treated animal (bottom), indicative of parenchymal injury due to the presence of tumor cells. Schematic diagram of ALA metabolism is shown on the right.

Provided herein are novel recombinant anti-CECAM1 antibodies and anti-CEACAM1-binding peptides, and methods of their use in anti-tumor cell-proliferation and anti-tumor-invasiveness therapies, such as the treatment of cancer, particularly pancreatic cancer. In addition, the compositions comprising the anti-CECAM-binding peptides and recombinant antibodies described herein are useful in "theranostic applications," e.g., assessment and imaging methods, such as companion diagnostics for determining CEACAM1 expression in tumor biopsies to identify likely responders for personalized medicine approaches, CEACAM1-targeted molecular imaging of tumorigenisis which can be used, for example, in serial monitoring of response(s) to therapy, and in vivo detection of tumors. Further, such diagnostics provide novel approaches for anti-cancer therapies for use in personalized medicine applications. Furthermore, the compositions comprising the anti-CEACAM1-binding peptides and anti-CEACAM1 antibodies described herein are useful as targeting moieties for other diagnostic and therapeutic compositions, in combination with delivery agents such as nanoparticles, polyplexes, microparticles, etc. In particular, the present embodiments provide the complementarity determining region (CDR) sequences of specific anti-CEACAM1 antibodies, which can be used in a variety of anti-CEACAM1-binding peptides.

As demonstrated herein, administration of the anti-CEACAM-1 antibody, 5F4, prevents pancreatic cancer growth and metastasis to other organs, as well as regional lymph nodes, in a murine model of pancreatic cancer. Accordingly, the compositions and methods described herein are particularly suited for and useful in the treatment, inhibition, and/or prevention of pancreatic cancer, and the treatment, inhibition, and/or prevention of metastases.

CEACAM1

Increasing clinical evidence shows that high level CEACAM1 expression on tumors and tumor-infiltrating lymphocytes correlates with poor prognosis and high risk of metastasis, although, paradoxically, carcinoembryonic antigen related cell adhesion molecule 1 (CEACAM1) has long been believed to act as a tumor suppressor.

Carcinoembryonic antigen (CEA)-related cell adhesion molecule 1 (CEACAM1) is a member of the CEA-family of immunoglobulin (Ig)-like transmembrane proteins. Beauchemin et al., 252 Exp. Cell Res. 243 (1999); Gray-Owen & Blumberg, 6 Nat. Rev. Immunol. 433 (2006). CEACAM1 is constitutively expressed in a wide range of tissues and cell types. Its expression on Natural Killer (NK) cells and T cells is, however, mainly induced by cytokines and membrane-activating receptor activation. Azuz-Lieberman et al., 17 Int. Immunol. 837 (2005); Gray-Owen & Blumberg, 2006; Moller et al., 65 Int. J. Cancer 740 (1996); Nakajima et al., 168 J. Immunol. 1028 (2002); Singer et al., 168 J. Immunol. 5139 (2002). When expressed, CEACAM1 is characterized by significant alternate RNA splicing leading to 11 isoforms in humans and at least 4 isoforms in mice. These isoforms differ in the length of the cytoplasmic tail (CT) and the number of extracellular Ig-like domains and are named accordingly. The majority of CEACAM1 isoforms possess either a long (CEACAM1-L) CT or a short (CEACAM1-S) CT.

CEACAM1-L isoforms predominate in NK cells and T cells, and contain two immunoreceptor tyrosine-based inhibitory motifs (ITIM). Beauchemin et al., 14 Oncogene 783 (1997); Chen et al., 180 J. Immunol. 6085 (2008); Singer et al., 168 J. immunol. 5139 (2002). Previous studies have shown that CEACAM1-L isoforms inhibit T cell receptor (TCR)/CD3 complex, B cell receptor (BCR), and Toll-like receptor 2 (TLR-2)-mediated immune responses. Boulton & Gray-Owen, 3 Nat. Immunol. 229 (2002); Chen et al., 86 J. Leukoc. Biol. 195 (2009); Chen et al., 2008; Lobo et al., 86 J. Leukoc. Biol. 205 (2009); Slevogt et al., 9 Nat. Immunol. 1270 (2008). In each of these cases, this inhibition is mechanistically related to growth factor receptor tyrosine kinase- or Src kinase-mediated phosphorylation of the CEACAM1-L CT-associated ITIMs, recruitment of Src homology phosphatase 1 (SHP-1) and/or SHP-2, and consequently inhibition of downstream signaling elements. Abou-Rjaily et al., 114 J. Clin. Invest. 944 (2004); Beauchemin et al., 1997; Chen et al., 2008; Huber et al., 274 J. Biol. Chem. 335 (1999); Izzi et al., 18 Oncogene 5563 (1999); Klaile et al., 187 J. Cell Biol. 553 (2009); Muller et al., 187 J. Cell Biol 569 (2009); Najjar, 13 Metab. 240 (2002); Nouvion et al. 123 J. Cell Sci. 4421 (2010).

CEACAM1 expression, or lack thereof, has been associated with a variety of tumors, especially those of epithelial cell origin (Obrink, 60 Lung Cancer 309 (2008)). Early studies recognized that sporadic colorectal cancers that derive from the transformation of intestinal epithelial cells (IEC) and prostate cancers commonly do not express CEACAM1, indicating that CEACAM1-L isoforms in epithelia serve a tumor suppressor function given that the CEACAM1-L CT isoforms are commonly expressed in epithelia cells and are typically inhibitory. Hsieh et al., 41 Prostate 31 (1999); Izzi et al., 1999; Obrink, 2008; Rosenberg et al., 53 Cancer Res. 4938 (1993). Consistent with this, tumor size and number are increased in Ceacam 1−/− mice exposed to azoxymethane administration (Leung et al., 25 Oncogene 5527 (2006).

In contrast to such initial studies, however, numerous recent clinical studies in a wide variety of human tumors including melanoma (Gambichler et al., 131 Am. J. Pathol. 782 (2009); Markel et al., 59 Cancer Immunol. Immunother. 215 (2010)); and cancers of the lung (Dango et al., 60 Lung Cancer 426 (2008); Sienel et al., 9 Clin. Cancer Res. 2260 (2003); Xi et al., 36 Nucl. Acids Res. 6535 (2008)); pancreas (Simeone et al., 34 Pancreas 436 (2007)); bladder (Tilki et al., 57 Eur. Urol. 648(2010)); colon (Kang et al., 22 Intl. J. Colorectal Dis. 869 (2007)); thyroid (Liu et al., 26 Oncogene 2747 (2007)); and prostate (Briese et al., 25 Intl. J. Gynecol. Pathol. 161 (2006)), have observed that high levels of CEACAM1 expression on tumor cells or tumor-infiltrating lymphocytes (TIL) (Markel et al., 177 J. Immunol. 6062 (2006)), correlates directly with poor prognosis.

It is important to note that CEACAM1 can also contribute to other effects on tumor microenvironments. For example, expression of CEACAM1 by the neovasculature can promote angiogenesis and facilitate the migration of CEACAM1-bearing tumors into blood and/or lymphatic vessels possibly via homophilic or other interactions, indicating that blockade of these would inhibit tumor progression. Horst et al., 116 J. Clin. Invest. 1596 (2006); Wagener & Ergun, 261 Exp. Cell Res. 19 (2000); Zhou et al., 205 Pathol. Res. Pract. 483 (2009a); Zhou et al., 4 Nat. Immunol. 565 (2009b). Moreover, CEACAM1 can negatively regulate a variety of activating immune receptors on T cells (e.g., IL-2 receptor and TCR) (Chen et al., 2008; Lee et al., 180 J. Immunol. 6827 (2008)), B cells (BCR) (Lobo et al., 2009), and epithelial cells (EGFR and TLR2) (Slevogt et al., 9 Nat. Immunol. 1270 (2008)), which can further impact anti-tumor immunity in the relevant tumor context.

A common feature of all of the aforementioned mechanisms by which CEACAM1 can regulate anti-tumor immunity at the level of either the tumor itself or the relevant immune effector cell is through expression of an ITIM-containing CEACAM1 isoform, able to associate with SHP-1. Due to the ability of SHP-1 to inactivate a wide variety of enzymatically active molecules by dephosphorylation of tyrosine residues (Lorenz, 228 Immunol. Rev. 342 (2009)), the association with and regulation of SHP-1 by CEACAM1-L isoforms can have broad implications for anti-tumor immunity. For example, in T and NK cells, in which SHP-1 is typically excluded from lipid raft structures (Fawcett & Lorenz, 174 J. Immunol. 2849 (2005)), where receptors such as TCR/CD3 complex and NKG2D typically reside during cellular activation, CEACAM1 can, without wishing to be bound or limited by theory, function as a shuttle to transport SHP-1 into this locale to inactivate ZAP-70 (Chen et al., 2008), in the case of the TCR/CD3 complex, by dephosphorylation of the corresponding tyrosine residues. In this case, expression of CEACAM1 on T and NK cells favors tumor cell escape from innate and adaptive immune mechanisms. In comparison, recruitment of SHP-1 into the proximity of a cell membrane-associated growth factor receptor, such as EGFR, on a tumor cell might result in inactivation of its growth promoting properties. Abou-Rjaily et al., 2004. As such, it is conceivable that CEACAM1-L isoforms display an inhibitory effect on tumor cell growth. Thus, the ability of CEACAM1-L isoforms to associate with SHP-1 and direct this to a variety of different cell surface receptors can have broad effects on primary tumor development and anti-tumor immunity.

CEACAM1 Antagonists and Anti-CEACAM1 Antibodies

Provided herein are compositions comprising CEACAM1 antagonists that are capable of neutralizing, blocking, inhibiting, abrogating, reducing, or interfering with CEACAM1 biological activity, such as an anti-CEACAM1 antibody or portion thereof that is specific for a CEACAM1 target, where the anti-CEACAM1 antibody or portion thereof specifically binds to the CEACAM1 target. In some embodiments, the CEACAM1 is human CEACAM1. Thus, anti-CEACAM1 antibodies or portions thereof that are useful in the compositions and methods described herein include any antibodies or antibody fragments thereof that bind with sufficient affinity and specificity to CEACAM1, i.e., are specific for CEACAM1, and can reduce or inhibit the biological activity of CEACAM1. In some aspects, provided herein is an anti-CEACAM1 antibody or portion thereof that binds to CEACAM1 and inhibits CEACAM1 biological activity or blocks interaction of CEACAM1 with cells, such as immune cells. Further description and examples of anti-CEACAM1 antibodies and portions thereof useful with the compositions and methods described herein, as well as methods of making and characterizing the same, are known in the art or explained herein.

Anti-CEACAM1 Antibodies and Antibody Production

Provided herein, in some aspects, are humanized or composite human anti-CEACAM1 antibodies or portions thereof for use in the compositions and methods described herein. Humanized forms of non-human (e.g., murine) antibodies, as used herein, refer to chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, a humanized antibody can comprise substantially all of, at least one, and typically two, variable domains, in which all or substantially all of the hypervariable loops correspond to those of a non-human immunoglobulin, and all or substantially all of the FR regions are those of a human immunoglobulin sequence. The humanized antibody optionally also can comprise at least a portion of an immunoglobulin constant region (Fc), typically that of a human immunoglobulin. Jones et al., 1986); Riechmann et al., 332 Nature 323 (1988); Presta, 2 Curr. Op. Struct. Biol. 593 (1992).

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., 1986); Riechmann et al., 1988); Verhoeyen et al., 239 Science 1534 (1988)), by substituting rodent CDRs or CDR sequences for the corresponding sequences of a human antibody. Accordingly, such humanized antibodies are chimeric antibodies (U.S. Pat. No. 4,816, 567) where substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. In some embodiments, humanized antibodies comprising one or more variable domains comprising the amino acid sequence of the variable heavy (SEQ ID NO:26, SEQ ID NO:28, or SEQ ID NO:30) and/or variable light (SEQ ID NO:27, SEQ ID NO:29, SEQ ID NO:31, or SEQ ID NO:32) chain domains of the anti-CEACAM1 antibody 5F4 are provided.

Throughout the instant specification and claims, the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991), which is also available on the world wide web, and is expressly incorporated herein in its entirety by reference. The "EU index as in Kabat" refers to the residue numbering of the human IgG1 EU antibody.

As used herein, "antibody variable domain" refers to the portions of the light and heavy chains of antibody molecules that include amino acid sequences of Complementarity Determining Regions (CDRs; i.e., CDR1, CDR2, and CDR3), and Framework Regions (FRs). $V_H$ refers to the variable domain of the heavy chain. $V_L$ refers to the variable domain of the light chain. According to the methods used herein, the amino acid positions assigned to CDRs and FRs can be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

As used herein, the term "Complementarity Determining Regions" (CDRs), i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region can comprise amino acid residues from a "complementarity determining region" as defined by Kabat (i.e., about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e., about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some embodiments, a complementarity determining region can include amino acids from both a CDR region defined according to Kabat and a hypervariable loop.

In addition to generation and production via hybridomas, antibodies or antibody portions that specifically bind CEACAM1 can be isolated from antibody phage libraries generated using the techniques described in McCafferty et al., 348 Nature 552 (1990); Clackson et al., 352 Nature, 624 (1991). Marks et al., 222 J. Mol. Biol. 581 (1991) describe the isolation of murine and human antibodies, respectively, using phage libraries. Subsequent publications describe the production of high affinity (nM range) human antibodies by chain shuffling (Marks et al., 10 Bio/Technol. 779 (1992)), as well as combinatorial infection and in vivo recombination as a strategy for constructing very large phage libraries. Waterhouse et al., 21 Nuc. Acids. Res. 2265 (1993). Thus, these techniques are viable alternatives to traditional monoclonal antibody hybridoma techniques for isolation of monoclonal antibodies.

The DNA sequences encoding the antibodies or antibody fragment that specifically bind CEACAM1 also can be modified, for example, by substituting the coding sequence for human heavy- and light-chain constant domains in place of the homologous murine sequences (U.S. Pat. No. 4,816, 567; Morrison et al., 81 PNAS 6851 (1984)), or by covalently joining to the immunoglobulin coding sequence all or part of the coding sequence for a non-immunoglobulin polypeptide, as also described elsewhere herein.

A suitable oligonucleotide, or set of oligonucleotides, which is capable of encoding a peptide of the CEACAM1-specific recombinant antibodies or portions thereof (or which is complementary to such an oligonucleotide, or set of oligonucleotides) is identified (using the above-described procedure), synthesized, and hybridized by means well known in the art, against a DNA or a cDNA preparation derived from cells which are capable of expressing anti-CEACAM1 antibodies or variable or constant regions thereof. Single stranded oligonucleotide molecules complementary to the "most probable" anti-CEACAM1 region peptide coding sequences can be synthesized using procedures which are well known to those of ordinary skill in the art. See Belagaje et al., 254 J. Biol. Chem. 5765-80 (1979); Maniatis et al., in MOLEC. MECH. CONTROL GENE EXPRESSION (Nierlich et al., eds., Acad. Press, NY, 1976); Wu et al., 1978; Khorana, 203 Science 614-25 (1979).

Additionally, DNA synthesis can be achieved through the use of automated synthesizers.

It is also intended that the antibody coding regions for use in the present invention can also be provided by altering existing antibody genes using standard molecular biological techniques that result in variants (agonists) of the antibodies and peptides described herein. Such variants include, but are not limited to deletions, additions and substitutions in the amino acid sequence of the recombinant anti-CEACAM1 antibodies or peptides.

Additionally, non-immunoglobulin polypeptides can be substituted for the constant domains of an antibody, or they can be substituted for the variable domains of one antigen-combining site of an antibody to create a chimeric bivalent antibody comprising one antigen-combining site having specificity for an antigen and another antigen-combining site having specificity for a different antigen.

Accordingly, provided herein, in some aspects, are humanized anti-CEACAM1 antibodies or portions thereof that comprise or consist of a sequence of the antibodies described herein. In some embodiments of these aspects, one or more heavy and/or one or more light chain CDR regions of a humanized anti-CEACAM1 antibody or antigen-binding portion thereof comprises or consists of a sequence of the antibodies described herein.

The amino acids of CDR1 of the heavy chain of the monoclonal antibody produced by hybridoma 5F4/2C6/2H3 are SSHGMS (SEQ ID NO:1). The amino acids of CDR2 of the heavy chain of the monoclonal antibody produced by hybridoma 5F4/2C6/2H3 are TISSGGTYTYYPDSVKG (SEQ ID NO:2). The amino acids of CDR3 of the heavy chain of the monoclonal antibody produced by hybridoma 5F4/2C6/2H3 are HDFDYDAAWFAY (SEQ ID NO:3).

The amino acids of CDR1 of the light chain of the monoclonal antibody produced by hybridoma 5F4/2C6/2H3 are SANSSVSYMY (SEQ ID NO:4). The amino acids of CDR2 of the light chain of the monoclonal antibody produced by hybridoma 5F4/2C6/2H3 are LTSNLAS (SEQ ID NO:5). The amino acids of CDR3 of the light chain of the monoclonal antibody produced by hybridoma 5F4/2C6/2H3 are QQWSSNPPT (SEQ ID NO:6).

The amino acids of CDR1 of the heavy chain of the monoclonal antibody produced by hybridoma 34B1/2E8/2E6 are SFYGMS (SEQ ID NO:7). The amino acids of CDR2 of the heavy chain of the monoclonal antibody produced by hybridoma 34B1/2E8/2E6 are TFSGGGNY-TYYPDSVKG (SEQ ID NO:8). The amino acids of CDR3 of the heavy chain of the monoclonal antibody produced by hybridoma 34B1/2E8/2E6 are HGGLPFYAMDY (SEQ ID NO:9).

The amino acids of CDR1 of the light chain of the monoclonal antibody produced by hybridoma 34B1/2E8/2E6 are SVSSSISSSNLH (SEQ ID NO:10). The amino acids of CDR2 of the light chain of the monoclonal antibody produced by hybridoma 34B1/2E8/2E6 are GTFNLAS (SEQ ID NO:11). The amino acids of CDR3 of the light chain of the monoclonal antibody produced by hybridoma 34B1/2E8/2E6 are QQWSSHPFT (SEQ ID NO:12).

The amino acids of CDR1 of the heavy chain of the monoclonal antibody produced by hybridoma 26H7/2H9/2E10 are SDYYLY (SEQ ID NO:13). The amino acids of CDR2 of the heavy chain of the monoclonal antibody produced by hybridoma 26H7/2H9/2E10 are TISVGGGNT-SYPDSVKG (SEQ ID NO:14). The amino acids of CDR3 of the heavy chain of the monoclonal antibody produced by hybridoma 26H7/2H9/2E10 are GLTTGPAWFAY (SEQ ID NO:15).

The amino acids of CDR1 of the light chain of the monoclonal antibody produced by hybridoma 26H7/2H9/2E10(seq1) are KSSQSLLNSSNQKNYLA (SEQ ID NO:16). The amino acids of CDR2 of the light chain of the monoclonal antibody produced by hybridoma 26H7/2H9/2E10(seq1) are FASTRES (SEQ ID NO:17). The amino acids of CDR3 of the light chain of the monoclonal antibody produced by hybridoma 26H7/2H9/2E10(seq1) are QQHYSTPWT (SEQ ID NO:18).

The amino acids of CDR1 of the light chain of the monoclonal antibody produced by hybridoma 26H7/2H9/2E10(seq2) are RASQKISGYLS (SEQ ID NO:19). The amino acids of CDR2 of the light chain of the monoclonal antibody produced by hybridoma 26H7/2H9/2E10(seq2) are AASTLDS (SEQ ID NO:20). The amino acids of CDR3 of the light chain of the monoclonal antibody produced by hybridoma 26H7/2H9/2E10(seq2) are LQYASSLMYT (SEQ ID NO:21).

Accordingly, in some aspects described herein, one or more variable heavy and/or one or more variable light chain CDR regions of a humanized anti-CEACAM1 antibody or portion thereof comprises or consists of a sequence of the monoclonal antibodies described herein.

In some such embodiments, the one or more variable heavy chain CDR1 regions comprises a peptide with an amino acid sequence selected from the group consisting of SEQ ID NO:1, SEQ ID NO:7, and SEQ ID NO:13.

In some such embodiments, the one or more variable heavy chain CDR2 regions comprises a peptide with an amino acid sequence selected from the group consisting of SEQ ID NO:2
SEQ ID NO:8, and SEQ ID NO:14.

In some such embodiments, the one or more variable heavy chain CDR3 regions comprises a peptide with an amino acid sequence selected from the group consisting of SEQ ID NO:3, SEQ ID NO:9, and SEQ ID NO:15.

In some such embodiments, the one or more variable light chain CDR1 regions comprises a peptide with the amino acid sequence selected from the group consisting of SEQ ID NO:4, SEQ. ID NO:10, SEQ ID NO:16, and SEQ ID NO:19.

In some such embodiments, the one or more variable light chain CDR2 regions comprises a peptide sequence selected from the group consisting of SEQ ID NO:5, SEQ ID NO:11, SEQ ID NO:17, and SEQ ID NO:20.

In some such embodiments, the one or more variable light chain CDR3 regions comprises a peptide with the amino acid sequence selected from the group consisting of SEQ ID NO:6, SEQ ID NO:12, SEQ ID NO:18, and SEQ ID NO:21.

In some embodiments of the aspects described herein, a humanized anti-CEACAM1 monoclonal antibody comprises mutated human IgG1 framework regions and one or more heavy and/or one or more light chain CDR regions from the anti-human CEACAM1 monoclonal antibody 5F4, described herein, that blocks binding of human CEACAM1 to its ligands. In some embodiments, a humanized anti-CEACAM1 monoclonal antibody comprises mutated human IgG4 framework regions and one or more heavy and/or one or more light chain CDR regions from the murine anti-human CEACAM1 monoclonal antibody 5F4, described herein, that blocks binding of human CEACAM1 to its ligands.

The choice of human variable domains, both light and heavy, to be used in making the humanized antibodies is important to reduce antigenicity. According to the so-called "best-fit" method, the amino acid sequences of the variable heavy and light chain domains of an antibody, such as that of the 5F4 antibody (SEQ ID NO:26 and SEQ ID NO:27, receptively), are screened against the entire library of known human variable-domain sequences. The human sequence which is closest to that of the rodent is then accepted as the human framework (FR) for the humanized antibody. Sims et al., 151 J. Immunol. 2296 (1993); Chothia et al., 196 J. Mol. Biol. 901 (1987). Another method uses a particular framework derived from the consensus sequence of all human antibodies of a particular subgroup of light or heavy chains. The same framework can be used for several different humanized antibodies (Carter et al., 89 PNAS 4285 (1992); Presta et al., 1993).

It is further important that antibodies be humanized with retention of high affinity for the antigen and other favorable biological properties, for example, the anti-tumor or anti-metastatic properties of the anti-CEACAM1 antibody 5F4 described herein. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., 90 PNAS 2551 (1993); Jakobovits et al., 362 Nature 255 (1993); Bruggermann et al., 7 Yr. Immunol. 33 (1993); Duchosal et al., 355 Nature 258 (1992).

Alternatively, phage display technology (McCafferty et al., 348 Nature 552 (1990)) can be used to produce human antibodies and antibody fragments in vitro, from immunoglobulin variable domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson et al., 3 Curr. Op. Str. Biol. 564 (1993). Several sources of V-gene segments can be used for phage display. Clackson et al., 1991, isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., 1991, or Griffith et al., 12 EMBO J. 725 (1993). See, also, U.S. Pat. No. 5,565,332 and U.S. Pat. No. 5,573,905.

Human antibodies can also be generated by in vitro activated B cells (see U.S. Pat. No. 5,567,610 and U.S. Pat. No. 5,229,275).

Composite Human Antibodies

In some embodiments of the aspects described herein, composite human antibody technology that generates de-immunized 100% engineered human antibodies can be used to prepare "composite human" or "composite humanized" anti-CEACAM1 antibodies for use in the compositions and methods described herein, using, for example, a technology as described by Antitope.

Briefly, as used herein, "composite human antibodies" or "composite humanized antibodies" comprise multiple sequence segments ("composites") derived from V-regions of unrelated human antibodies that are selected to maintain monoclonal antibody sequences critical for antigen binding of the starting precursor anti-human CEACAM1 monoclonal antibody, such as 5F4 antibody, and which have all been filtered for the presence of potential T-cell epitopes using "in silico tools" (Holgate & Baker, 2009). The close fit of human sequence segments with all sections of the starting antibody V regions and the elimination of CD4+ T cell epitopes prior to synthesis of the antibody allow this technology to circumvent immunogenicity in the development of '100% engineered composite human' therapeutic antibodies while maintaining optimal affinity and specificity through the prior analysis of sequences necessary for antigen-specificity (Holgate & Baker, 2009).

Accordingly, in some embodiments, an anti-CEACAM1 composite human antibody comprises a variable heavy ($V_H$) chain amino acid sequence selected from the peptides with an amino acid sequence of SEQ ID NO:26, SEQ ID NO:28, or SEQ ID NO:30.

In some embodiments, an anti-CEACAM1 composite human antibody comprises a variable light ($V_L$) chain amino acid sequence selected from the group consisting of SED ID NO:27, SEQ ID NO:29, SEQ ID NO:31, and SEQ ID NO:32.

In some embodiments, an anti-CEACAM1 composite human antibody can include a heavy chain CDR1 region comprising an amino acid sequence of SEQ ID NO:1. In some embodiments, an anti-CEACAM1 composite human antibody can include a heavy chain CDR2 region comprising an amino acid sequence of SEQ ID NO:2. In some embodiments, an anti-CEACAM1 composite human antibody comprises a heavy chain CDR3 region comprising an amino acid sequence of SEQ ID NO:3.

In some embodiments, an anti-CEACAM1 composite human antibody comprises a light chain CDR1 region comprising a sequence of SEQ ID NO:4. In some embodiments, an anti-CEACAM1 composite human antibody comprises a light chain CDR2 region comprising an amino acid sequence of SEQ ID NO:5. In some embodiments, an anti-CEACAM1 composite human antibody comprises a light chain CDR3 region comprising an amino acid sequence of SEQ ID NO:6.

Anti-CEACAM1 Antibody Fragments

In some embodiments of the aspects described herein, a recombinant antibody specific for CEACAM1, such as, for example: the anti-CEACAM1 5F4 antibody; an anti-CEACAM1 antibody comprising one or more heavy chain CDR regions comprising a sequence selected from the group consisting of SEQ ID NO:1, SEQ ID NO:2, and SEQ ID NO:3; an anti-CEACAM1 antibody comprising one or more light chain CDR regions comprising a sequence selected from the group consisting of SEQ ID NO:4, SEQ ID NO:5, and SEQ ID NO:6; an anti-CEACAM1 composite human or composite humanized antibody comprising a variable heavy ($V_H$) chain amino acid sequence selected from the group consisting of SEQ ID NO:26, SEQ ID NO:28, and SEQ ID NO:30; and/or an anti-CEACAM1 composite human antibody comprising a variable light ($V_L$) chain amino acid sequence selected from the group consisting of SEQ ID NO:27, SEQ ID NO:29, SEQ ID NO:31, and SEQ ID NO:32, can be treated or processed into an antibody fragment thereof.

Various techniques have been developed and are available for the production of antibody fragments. Traditionally, these fragments were derived via proteolytic digestion of intact antibodies. See, e.g., Morimoto et al., 24 J. Biochem. Biophys. Meths. 107 (1992); Brennan et al., 229 Science 81 (1985). However, these fragments can now be produced directly by recombinant host cells. For example, antibody fragments can be isolated from the antibody phage libraries discussed herein. Alternatively, Fab'-SH fragments can be directly recovered from E. coli and chemically coupled to form F(ab')$_2$ fragments (Carter et al., 1992). According to another approach, F(ab')$_2$ fragments can be isolated directly from recombinant host cell culture. Other techniques for the production of antibody fragments will be apparent to the skilled practitioner. In other embodiments, the antibody fragment of choice is a single chain Fv fragment (scFv). See, for example, WO 93/16185.

In some embodiments of the aspects described herein, a human CEACAM1-specific antibody fragment is a Fab fragment comprising $V_L$, $C_L$, $V_H$ and $C_H1$ domains. Fab fragments comprise or consist essentially of a variable and constant domain of the light chain and a variable domain and the first constant domain ($C_H1$) of the heavy chain. In some such embodiments, the $V_H$ domain is selected from the peptides with an amino acid sequence of SEQ ID NO:26, SEQ ID NO:28, or SEQ ID NO:30. In some such embodiments, the $V_H$ domain comprises one or more heavy chain CDR regions comprising a sequence selected from the group consisting of SEQ ID NO:1, SEQ ID NO:2, SEQ ID NO:3, SEQ ID NO:7, SEQ ID NO:8, SEQ ID NO:9, SEQ ID NO:13, SEQ ID NO:14, and SEQ ID NO:15. In some such embodiments, the $V_L$ domain is selected from the group consisting of SEQ ID NO:27, SEQ ID NO:29, SEQ ID NO:31, and SEQ ID NO:32. In some such embodiments, the $V_L$ domain comprises one or more light chain CDR regions comprising a sequence selected from the group consisting of SEQ ID NO:4, SEQ ID NO:5, SEQ ID NO:6, SEQ ID NO:10, SEQ ID NO:11, SEQ ID NO:12, SEQ ID NO:16, SEQ ID NO:17, SEQ ID NO:18, SEQ ID NO:19, SEQ ID NO:20, and SEQ ID NO:21.

In some embodiments of the aspects described herein, a human CEACAM1-specific antibody fragment is a Fab' fragment, which refers to a Fab fragment having one or more cysteine residues at the C-terminus of the $C_H1$ domain.

In some embodiments of the aspects described herein, a human CEACAM1-specific antibody fragment is a Fd fragment comprising or consisting essentially of $V_H$ and $C_H1$ domains. In some such embodiments, the $V_H$ domain is selected from the peptides with an amino acid sequence of SEQ ID NO:26, SEQ ID NO:28, or SEQ ID NO:30. In some such embodiments, the $V_H$ domain comprises one or more heavy chain CDR regions comprising a sequence selected from the group consisting of SEQ ID NO:1, SEQ ID NO:2, SEQ ID NO:3, SEQ ID NO:7, SEQ ID NO:8, SEQ ID NO:9, SEQ ID NO:13, SEQ ID NO:14, and SEQ ID NO:15.

In some embodiments of the aspects described herein, a human CEACAM1-specific antibody portion is a Fd' fragment comprising VH and CH1 domains and one or more cysteine residues at the C-terminus of the CH1 domain. In some such embodiments, the $V_H$ domain is selected from the peptides with an amino acid sequence of SEQ ID NO:26, SEQ ID NO:28, or SEQ ID NO:30. In some such embodiments, the $V_H$ domain comprises one or more heavy chain CDR regions comprising a sequence selected from the group consisting of SEQ ID NO:1, SEQ ID NO:2, SEQ ID NO:3, SEQ ID NO:7, SEQ ID NO:8, SEQ ID NO:9, SEQ ID NO:13, SEQ ID NO:14, and SEQ ID NO:15. In some such embodiments, the $V_L$ domain is selected from the group consisting of SEQ ID NO:27, SEQ ID NO:29, SEQ ID NO:31, and SEQ ID NO:32. In some such embodiments, the $V_L$ domain comprises one or more light chain CDR regions comprising a sequence selected from the group consisting of SEQ ID NO:4, SEQ ID NO:5, SEQ ID NO:6, SEQ ID NO:10, SEQ ID NO:11, SEQ ID NO:12, SEQ ID NO:16, SEQ ID NO:17, SEQ ID NO:18, SEQ ID NO:19, SEQ ID NO:20, and SEQ ID NO:21.

Single-chain Fv or scFv antibody fragments comprise or consist essentially of the $V_H$ and $V_L$ domains of antibody, such that these domains are present in a single polypeptide chain. Generally, a Fv polypeptide further comprises a polypeptide linker between the VH and VL domains, which allows the scFv to form the desired structure for antigen binding. See, for example, Pluckthun, 113 Pharmacology Monoclonal Antibodies 269 (Rosenburg & Moore, eds., Springer-Verlag, New York, 1994). Accordingly, in some embodiments of the aspects described herein, a human CEACAM1-specific antibody fragment is a Fv fragment comprising or consisting essentially of the VL and VH domains of a single arm of an antibody. In some such embodiments, the VH domain is selected from the group consisting of SEQ ID NO:26, SEQ ID NO:28, and SEQ ID NO:30. In some such embodiments, the $V_H$ domain comprises one or more heavy chain CDR regions comprising a sequence selected from the group consisting of SEQ ID NO:1, SEQ ID NO:2, SEQ ID NO:3, SEQ ID NO:7, SEQ ID NO:8, SEQ ID NO:9, SEQ ID NO:13, SEQ ID NO:14, and SEQ ID NO:15. In some such embodiments, the $V_L$ domain is selected from the group consisting of SEQ ID NO:27, SEQ ID NO:29, SEQ ID NO:31, and SEQ ID NO:32. In some such embodiments, the $V_L$ domain comprises one or more light chain CDR regions comprising a sequence selected from the group consisting of SEQ ID NO:4, SEQ ID NO:5, SEQ ID NO:6, SEQ ID NO:10, SEQ ID NO:11, SEQ ID NO:12, SEQ ID NO:16, SEQ ID NO:17, SEQ ID NO:18, SEQ ID NO:19, SEQ ID NO:20, and SEQ ID NO:21.

The term diabodies refers to small antibody portions with two antigen-binding sites, which portions comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. See, e.g., EP 404,097; WO 93/11161; Hollinger et al., 90 PNAS 6444 (1993).

Accordingly, in some embodiments of the aspects described herein, a human CEACAM1-specific antibody portion is a diabody comprising two antigen binding sites, comprising a heavy chain variable domain ($V_H$) connected to a light chain variable domain ($V_L$) in the same polypeptide chain. In some such embodiments, the $V_H$ domain is selected from the peptides with an amino acid sequence of SEQ ID NO:26, SEQ ID NO:28, or SEQ ID NO:30. In some such embodiments, the $V_H$ domain comprises one or more heavy chain CDR regions comprising a sequence selected from the group consisting of SEQ ID NO:1, SEQ ID NO:2, SEQ ID NO:3, SEQ ID NO:7, SEQ ID NO:8, SEQ ID NO:9, SEQ ID NO:13, SEQ ID NO:14, and SEQ ID NO:15. In some such embodiments, the $V_L$ domain is selected from the group consisting of SEQ ID NO:27, SEQ ID NO:29, SEQ ID NO:31, and SEQ ID NO:32. In some such embodiments, the $V_L$ domain comprises one or more light chain CDR regions comprising a sequence selected from the group consisting of SEQ ID NO:4, SEQ ID NO:5, SEQ ID NO:6, SEQ ID NO:10, SEQ ID NO:11, SEQ ID NO:12, SEQ ID NO:16, SEQ ID NO:17, SEQ ID NO:18, SEQ ID NO:19, SEQ ID NO:20, and SEQ ID NO:21.

In some embodiments of the aspects described herein, a human CEACAM1-specific antibody portion is a dAb fragment comprising or consisting essentially of a $V_H$ domain. In some such embodiments, the $V_H$ domain is selected from the peptides with an amino acid sequence of SEQ ID NO:26, SEQ ID NO:28, or SEQ ID NO:30. In some such embodiments, the $V_H$ domain comprises one or more heavy chain CDR regions comprising a sequence selected from the group consisting of SEQ ID NO:1, SEQ ID NO:2, SEQ ID NO:3, SEQ ID NO:7, SEQ ID NO:8, SEQ ID NO:9, SEQ ID NO:13, SEQ ID NO:14, and SEQ ID NO:15.

In some embodiments of the aspects described herein, a human CEACAM1-specific antibody portion comprises or consists essentially of one or more isolated CDR regions. In some such embodiments, the isolated CDR region comprises one or more heavy chain CDR regions comprising a sequence selected from the group consisting of SEQ ID NO:1, SEQ ID NO:2, SEQ ID NO:3, SEQ ID NO:7, SEQ ID NO:8, SEQ ID NO:9, SEQ ID NO:13, SEQ ID NO:14, and SEQ ID NO:15. In some such embodiments, the isolated CDR region comprises one or more light chain CDR regions comprising a sequence selected from the group consisting of SEQ ID NO:4, SEQ ID NO:5, SEQ ID NO:6, SEQ ID NO:10, SEQ ID NO:11, SEQ ID NO:12, SEQ ID NO:16, SEQ ID NO:17, SEQ ID NO:18, SEQ ID NO:19, SEQ ID NO:20, and SEQ ID NO:21.

In some embodiments of the aspects described herein, the human CEACAM1-specific antibody portion is a F(ab')$_2$ fragment, which comprises a bivalent fragment comprising two Fab' fragments linked by a disulphide bridge at the hinge region.

Linear antibodies refers to the antibodies as described in Zapata et al., Protein Engin., 8(10):1057-1062 (1995). Briefly, these antibodies comprise a pair of tandem Fd segments ($V_H$-$C_H$1-$V_H$-$C_H$1) which, together with complementary light chain polypeptides, form a pair of antigen binding regions. Linear antibodies can be bispecific or monospecific.

In some embodiments of the aspects described herein, a human CEACAM1-specific antibody fragment is a linear antibody comprising a pair of tandem Fd segments ($V_H$—$C_H$1-$V_H$-$C_H$1) which, together with complementary light chain polypeptides, form a pair of antigen binding regions. In some such embodiments, the $V_H$ domain is selected from the peptides with an amino acid sequence of SEQ ID NO:26, SEQ ID NO:28, or SEQ ID NO:30. In some such embodiments, the $V_H$ domain comprises one or more heavy chain CDR regions comprising a sequence selected from the group consisting of SEQ ID NO:1, SEQ ID NO:2, SEQ ID NO:3, SEQ ID NO:7, SEQ ID NO:8, SEQ ID NO:9, SEQ ID NO:13, SEQ ID NO:14, and SEQ ID NO:15. In some such embodiments, the $V_L$ domain is selected from the group consisting of SEQ ID NO:27, SEQ ID NO:29, SEQ ID NO:31, and SEQ ID NO:32. In some such embodiments, the $V_L$ domain comprises one or more light chain CDR regions comprising a sequence selected from the group consisting of SEQ ID NO:4, SEQ ID NO:5, SEQ ID NO:6, SEQ ID NO:10, SEQ ID NO:11, SEQ ID NO:12, SEQ ID NO:16, SEQ ID NO:17, SEQ ID NO:18, SEQ ID NO:19, SEQ ID NO:20, and SEQ ID NO:21.

In other embodiments of these aspects, a recombinant human CEACAM1-specific antibody portion has specificity for the same epitope as the monoclonal anti-CEACMAM1 antibody 5F4, described herein, and produced by hybridoma 5F4. In other embodiments of these aspects, a recombinant human CEACAM1-specific antibody portion has specificity for the same epitope as the monoclonal anti-CEACMAM1 antibody 26H7, described herein, and produced by hybridoma 26H7. In other embodiments of these aspects, a recombinant human CEACAM1-specific antibody portion has specificity for the same epitope as the monoclonal anti-CEACMAM1 antibody 34B1, described herein, and produced by hybridoma 34B1.

Other Amino Acid Sequence Modifications

In some embodiments of the aspects described herein, amino acid sequence modification(s) of the antibodies or antibody fragments thereof specific for CEACAM1 described herein are contemplated. For example, it can be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics, e.g., binding specificity, inhibition of biological activity. The amino acid changes also can alter post-translational processes of the antibody, such as changing the number or position of glycosylation sites.

Variant anti-CEACAM1 antibodies or peptides can be fully functional or can lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions can positively or negatively affect function to some degree. Non-functional variants typically contain one or more non-conservative amino acid substitutions, deletions, insertions, inversions, or truncation or a substitution, insertion, inversion, or deletion in a critical residue or critical region A useful method for identification of certain residues or regions of the antibody that are preferred locations for mutagenesis is called "alanine scanning mutagenesis" as described by Cunningham & Wells, Science 244: 1081 (1989). Here, a residue or group of target residues are identified (e.g., charged residues such as arg, asp, his, lys, and glu) and replaced by a neutral or negatively charged amino acid (typically alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody, such as, for example, biotin.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated for use in the antibodies or antibody fragments thereof specific for CEACAM1 described herein.

Substantial modifications in the biological properties of the antibodies or antibody fragments thereof specific for CEACAM1 are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids can be grouped according to similarities in the properties of their side chains (see Lehninger, BIOCHEMISTRY (2nd ed., Worth Publishers, New York, 1975): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Thus, for example, the CDR1 of the 5F4 heavy chain can be represented as $X^2X^2X^4X^2X^1X^2$, wherein $X^2$ is Gly (G), Ser (S), Thr (T), Cys (C), Tyr (Y), Asn (N), or Gln (Q); $X^4$ is Lys (K), Arg (R), or His (H); and $X^1$ is Ala (A), Val (V), Leu (L), Ile (I), Pro (P), Phe (F), Trp (W), or Met (M).

Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

Any cysteine residue not involved in maintaining the proper conformation of the antibodies or antibody fragments thereof specific for CEACAM1 also can be substituted, generally with serine, to improve the oxidative stability of the molecule and prevent aberrant crosslinking Conversely, cysteine bond(s) can be added to the antibody to improve its stability (particularly where the antibody is an antibody fragment such as an Fv fragment).

A particularly preferred type of substitutional variant involves substituting one or more hypervariable region residues of a parent antibody (e.g., the monoclonal anti-CEACAM1 antibody 5F4, or a humanized or composite human antibody or antibody fragment thereof specific for CEACAM1, as provided herein). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding.

Alternatively, or additionally, it can be beneficial to analyze a crystal structure of the antigen-antibody complex to identify contact points between the antibody or antibody fragments thereof specific for CEACAM1 and human CEACAM1. Such contact residues and neighboring residues are candidates for substitution according to the techniques elaborated herein. Once such variants are generated, the panel of variants is subjected to screening as described herein and antibodies or antibody fragments thereof with superior properties in one or more relevant assays can be selected for further development.

Another type of amino acid variant of the antibody alters the original glycosylation pattern of the antibody. By "altering the original glycosylation pattern" is meant deleting one or more carbohydrate moieties found in the antibody, and/or adding one or more glycosylation sites that are not present in the antibody. Glycosylation of antibodies is typically either N-linked or O-linked N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine can also be used. Addition of glycosylation sites to the antibodies or antibody fragments thereof specific for CEACAM1 is accomplished by altering the amino acid sequence such that it contains one or more of the above-described tripeptide sequences (for N-linked glycosylation sites). The alteration can also be made by the addition of, or substitution by, one or more serine or threonine residues to the sequence of the original antibody (for O-linked glycosylation sites).

Where the antibody comprises an Fc region, the carbohydrate attached thereto can be altered. For example, antibodies with a mature carbohydrate structure that lacks fucose attached to an Fc region of the antibody are described. See, e.g., U.S. Patent Pubs. No. 2003/0157108; No. 2004/0093621. Antibodies with a bisecting N-acetylglucosamine (GlcNAc) in the carbohydrate attached to an Fc region of the antibody are referenced in WO 03/011878; U.S. Pat. No. 6,602,684. Antibodies with at least one galactose residue in the oligosaccharide attached to an Fc region of the antibody are reported in WO 97/30087. See also WO 98/58964; WO 99/22764 concerning antibodies with altered carbohydrate attached to the Fc region thereof.

In some embodiments, it can be desirable to modify the antibodies or antibody fragments thereof specific for CEACAM1 described herein with respect to effector function, e.g., so as to enhance antigen-dependent cell-mediated cyotoxicity (ADCC) and/or complement dependent cytotoxicity (CDC) of the antibody. This can be achieved by introducing one or more amino acid substitutions in an Fc region of the antibody or antibody fragment thereof. Alternatively or additionally, cysteine residue(s) can be introduced in the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., 176 J. Exp. Med. 1191 (1992); Shopes, 148 J. Immunol. 2918 (1992). Homodimeric antibodies with enhanced antitumor activity can also be prepared using heterobifunctional cross-linkers as described in Wolff et al., 53 Cancer Res. 2560 (1993). Alternatively, an antibody can be engineered which has dual Fc regions and can thereby have enhanced complement lysis and ADCC capabilities. See Stevenson et al., 3 Anti-Cancer Drug Design 219 (1989).

For example, WO 00/42072 describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region (Eu numbering of residues). Typically, the altered Fc region is a human IgG1 Fc region comprising or consisting of substitutions at one, two or three of these positions. Such substitutions are optionally combined with substitution(s) which increase C1q binding and/or CDC.

Antibodies with altered C1q binding and/or complement dependent cytotoxicity (CDC) are described in WO 99/51642, U.S. Pat. No. 6,194,551, U.S. Pat. No. 6,242,195, U.S. Pat. No. 6,528,624, and U.S. Pat. No. 6,538,124. The antibodies comprise an amino acid substitution at one or more of amino acid positions 270, 322, 326, 327, 329, 313, 333 and/or 334 of the Fc region thereof (Eu numbering of residues).

To increase the serum half life of the antibody specific for CEACAM1 described herein, one can incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Antibodies with improved binding to the neonatal Fc receptor (FcRn), and increased half-lives, are described in WO 00/42072 and U.S. Patent Pub. No. 2005/0014934. These antibodies comprise an Fc region with one or more substitutions therein which improve binding of the Fc region to FcRn. For example, the Fc region can have substitutions at one or more of positions 238, 250, 256, 265, 272, 286, 303, 305, 307, 311, 312, 314, 317, 340, 356, 360, 362, 376, 378, 380, 382, 413, 424, 428 or 434 (Eu numbering of residues). The preferred Fc region-comprising antibody variant with improved FcRn binding comprises amino acid substitutions at one, two or three of positions 307, 380 and 434 of the Fc region thereof (Eu numbering of residues). In one embodiment, the antibody has 307/434 mutations. Engineered antibodies specific for CEACAM1 with three or more (e.g., four) functional antigen binding sites are also contemplated. See, e.g., U.S. Patent Pub. No. US2002/0004587.

Antibody and Antibody Fragment Thereof Production

Nucleic acid molecules encoding amino acid sequence variants of antibodies are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

Traditionally, monoclonal antibodies have been produced as native molecules in murine hybridoma lines. In addition to that technology, the methods and compositions described herein provide for recombinant DNA expression of monoclonal antibodies. This allows the production of humanized antibodies as well as spectrum of antibody derivatives and fusion proteins in a host species of choice. The production of antibodies in bacteria, yeast, transgenic animals and chicken eggs are also alternatives for hybridoma-based production systems. The main advantages of transgenic animals are potential high yields from renewable sources.

A nucleic acid sequence encoding at least one anti-CEACAM1 antibody, portion or polypeptide of the present invention can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, Lab. Manual (Cold Spring Harbor Lab. Press, NY, 1982 and 1989), and Ausubel, 1987, 1993, and can be used to construct nucleic acid sequences which encode a monoclonal antibody molecule or antigen binding region thereof.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as anti-CPAA peptides or antibody portions in recoverable amounts. The precise nature of the regulatory regions needed for gene expression may vary from organism to organism, as is well known in the analogous art. See, e.g., Sambrook et al., 1989; Ausubel et al., 1987-1993.

Accordingly, the expression of an anti-CEACAM1 antibody or peptide can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used.

Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an anti-CEACAM1 antibody or portion thereof of the present invention with a specified amino terminus sequence. Moreover, problems associated with retention of initiation codon-derived methionine residues in direct yeast (or bacterial) expression maybe avoided. Sabin et al., 7 Bio/Technol. 705 (1989); Miller et al., 7 Bio/Technol. 698 (1989).

Any of a series of yeast gene expression systems incorporating promoter and termination elements from the actively expressed genes coding for glycolytic enzymes produced in large quantities when yeast are grown in mediums rich in glucose can be utilized to obtain recombinant anti-CEACAM1 antibodies or peptides of the present invention. Known glycolytic genes can also provide very efficient transcriptional control signals. For example, the promoter and terminator signals of the phosphoglycerate kinase gene can be utilized.

Production of anti-CEACAM1 antibodies or peptides or functional derivatives thereof in insects can be achieved. For example, by infecting the insect host with a baculovirus engineered to express a transmembrane polypeptide by methods known to those of skill. See Ausubel et al., 1987, 1993.

In some embodiments, the introduced nucleotide sequence is incorporated into a plasmid or viral vector capable of autonomous replication in the recipient host. Any of a wide variety of vectors can be employed for this purpose and are known and available to those or ordinary skill in the art. See, e.g., Ausubel et al., 1987, 1993. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in *E. coli.*, for example. Other gene expression elements useful for the expression of cDNA encoding anti-CEACAM1 antibodies or peptides include, but are not limited to (a) viral transcription promoters and their enhancer elements, such as the SV40 early promoter (Okayama et al., 3 Mol. Cell. Biol. 280 (1983)), Rous sarcoma virus LTR (Gorman et al., 79 PNAS 6777 (1982)), and Moloney murine leukemia virus LTR (Grosschedl et al., 41 Cell 885 (1985)); (b) splice regions and polyadenylation sites such as those derived from the SV40 late region (Okayarea et al., 1983), and (c) polyadenylation sites such as in SV40 (Okayama et al., 1983).

Immunoglobulin cDNA genes can be expressed as described by Liu et al., infra, and Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., 1 Protein Engin. 499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In some embodiments, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene is assembled in, or inserted into, an expression vector. Recipient cells capable of expressing the chimeric immunoglobulin chain gene product are then transfected singly with an anti-CPAA peptide or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In some embodiments, the fused genes encoding the anti-CEACAM1 peptide or chimeric H and L chains, or portions thereof are assembled in separate expression vectors that are then used to co-transfect a recipient cell. Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. The genes so produced and amplified in a bacterial host are subsequently used to co-transfect a eukaryotic cell, and allow selection of a co-transfected cell carrying the desired transfected genes. Non-limiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively the fused genes encoding chimeric H and L chains can be assembled on the same expression vector.

For transfection of the expression vectors and production of the chimeric, humanized, or composite human antibodies described herein, the recipient cell line can be a myeloma cell. Myeloma cells can synthesize, assemble and secrete immunoglobulins encoded by transfected immunoglobulin genes and possess the mechanism for glycosylation of the immunoglobulin. For example, in some embodiments, the recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

An expression vector carrying a chimeric, humanized, or composite human antibody construct or anti-CEACAM1 polypeptide described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 Science 1538 (1988), as known to one of ordinary skill in the art.

Yeast provides certain advantages over bacteria for the production of immunoglobulin H and L chains. Yeasts carry out post-translational peptide modifications including glycosylation. A number of recombinant DNA strategies exist that utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Intl. Conf. Yeast, Genetics & Molec. Biol. (Montpelier, France, 1982).

Yeast gene expression systems can be routinely evaluated for the levels of production, secretion and the stability of anti-CEACAM1 peptides, antibodies, and assembled chimeric, humanized, or composite human antibodies, fragments and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast. See II DNA Cloning 45, (Glover, ed., IRL Press, 1985) and e.g., U.S. Publication No. US 2006/0270045 A1.

Bacterial strains can also be utilized as hosts for the production of the antibody molecules or peptides described herein, E. coli K12 strains such as E. coli W3110 (ATCC 27325), Bacillus species, enterobacteria such as Salmonella typhimurium or Serratia marcescens, and various Pseudomonas species can be used. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of chimeric, humanized, or composite humanized antibodies and fragments thereof encoded by the cloned immunoglobulin cDNAs or CDRs in bacteria (see Glover, 1985; Ausubel, 1987, 1993; Sambrook, 1989; Colligan, 1992-1996).

Host mammalian cells can be grown in vitro or in vivo. Mammalian cells provide post-translational modifications to immunoglobulin protein molecules including leader peptide removal, folding and assembly of H and L chains, glycosylation of the antibody molecules, and secretion of functional antibody protein.

Mammalian cells which can be useful as hosts for the production of antibody proteins, in addition to the cells of lymphoid origin described above, include cells of fibroblast origin, such as Vero (ATCC CRL 81) or CHO-K1 (ATCC CRL 61) cells. Exemplary eukaryotic cells that can be used to express polypeptides include, but are not limited to, COS cells, including COS 7 cells; 293 cells, including 293-6E cells; CHO cells, including CHO—S and DG44 cells; PER.C6® cells (Crucell); and NSO cells. In some embodiments, a particular eukaryotic host cell is selected based on its ability to make desired post-translational modifications to the anti-CEACAM1 heavy chains and/or anti-CEACAM1 light chains. For example, in some embodiments, CHO cells produce polypeptides that have a higher level of sialylation than the same polypeptide produced in 293 cells.

In some embodiments, one or more anti-CEACAM1 polypeptides can be produced in vivo in an animal that has been engineered or transfected with one or more nucleic acid molecules encoding the polypeptides, according to any suitable method.

In some embodiments, an anti-CEACAM1 antibody is produced in a cell-free system. Nonlimiting exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

Many vector systems are available for the expression of cloned anti-CEACAM1 peptides H and L chain genes in mammalian cells (see Glover, 1985). Different approaches can be followed to obtain complete $H_2L_2$ antibodies. As discussed above, it is possible to co-express H and L chains in the same cells to achieve intracellular association and linkage of H and L chains into complete tetrameric $H_2L_2$ antibodies and/or anti-CEACAM1-specific peptides. The co-expression can occur by using either the same or different plasmids in the same host. Genes for both H and L chains and/or anti-CEACAM peptides can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing anti-CEAMCAM1 peptides and/or $H_2L_2$ molecules via either route could be transfected with plasmids encoding additional copies of peptides, H, L, or H plus L chains in conjunction with additional selectable markers to generate cell lines with enhanced properties, such as higher production of assembled $H_2L_2$ antibody molecules or enhanced stability of the transfected cell lines.

Additionally, plants have emerged as a convenient, safe and economical alternative main-stream expression systems for recombinant antibody production, which are based on large scale culture of microbes or animal cells. Antibodies can be expressed in plant cell culture, or plants grown conventionally. The expression in plants may be systemic, limited to susb-cellular plastids, or limited to seeds (endosperms). See, e.g., U.S. Patent Pub. No. 2003/0167531; U.S. Pat. No. 6,080,560; U.S. Pat. No. 6,512,162; WO 0129242. Several plant-derived antibodies have reached advanced stages of development, including clinical trials (see, e.g., Biolex, N.C.).

In some aspects, provided herein are methods and systems for the production of a humanized antibody, which is prepared by a process which comprises maintaining a host transformed with a first expression vector which encodes the light chain of the humanized antibody and with a second expression vector which encodes the heavy chain of the humanized antibody under such conditions that each chain is expressed and isolating the humanized antibody formed by assembly of the thus-expressed chains. The first and second expression vectors can be the same vector. Also provided herein are DNA sequences encoding the light chain or the heavy chain of the humanized antibody; an expression vector which incorporates a said DNA sequence; and a host transformed with a said expression vector.

Generating a humanized antibody from the sequences and information provided herein can be practiced by those of ordinary skill in the art without undue experimentation. In one approach, there are four general steps employed to humanize a monoclonal antibody, see, e.g., U.S. Pat. No. 5,585,089; U.S. Pat. No. 6,835,823; U.S. Pat. No. 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Once expressed, the whole antibodies, their dimers, individual light and heavy chains, or other immunoglobulin forms of the present invention can be recovered and purified by known techniques, e.g., immunoabsorption or immunoaffinity chromatography, chromatographic methods such as HPLC (high performance liquid chromatography), ammonium sulfate precipitation, gel electrophoresis, or any combination of these. See generally, Scopes, PROTEIN PURIF. (Springer-Verlag, NY, 1982). Substantially pure immunoglobulins of at least about 90% to 95% homogeneity are advantageous, as are those with 98% to 99% or more homogeneity, particularly for pharmaceutical uses. Once purified, partially or to homogeneity as desired, a humanized or composite human antibody can then be used therapeutically or in developing and performing assay procedures, immunofluorescent stainings, and the like. See generally, Vols. I & II Immunol. Meth. (Lefkovits & Pernis, eds., Acad. Press, NY, 1979 and 1981).

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant CEACAM1 antibody of the invention. Such functional activities include biological activity and ability to bind to a ligand for an anti-CEACAM1 antibody. Additionally, a polypeptide having functional activity means the polypeptide exhibits activity similar, but not necessarily identical to, an activity of an anti-CEACAM1 antibody described herein, including mature forms, as measured in a particular assay, such as, for example, a biological assay, with or without dose dependency. In the case where dose dependency does exist, it need not be identical to that of the anti-CEACAM1 antibody, but rather substantially similar to the dose-dependence in a given activity as compared to the anti-CEACAM1 antibodies of the present invention (i.e., the candidate polypeptide will exhibit greater activity, or not more than about 25-fold less, about 10-fold less, or about 3-fold less activity relative to the anti-CEACAM1 antibodies described herein, such as 5F4).

Anti-CEACAM1 Immunoconjugates

In some embodiments of the aspects described herein, the antibody and antibody fragments specific for CEACAM1 are conjugated to an agent such as a chemotherapeutic agent, toxin (e.g., an enzymatically active toxin of bacterial, fungal, plant or animal origin, or fragments thereof), a small molecule, an siRNA, a nanoparticle, a targeting agent (e.g., a microbubble), or a radioactive isotope (i.e., a radioconjugate). Such conjugates are referred to herein as "immunoconjugates". Such immunoconjugates can be used, for example, in diagnostic, theranostic, or targeting methods.

Immunoconjugates which include one or more cytotoxins are referred to as "immunotoxins". A cytotoxin or cytotoxic agent includes any agent that is detrimental to and, in particular, kills cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Suitable therapeutic agents for forming immunoconjugates of the invention include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine). In some embodiments, the therapeutic agent is a cytotoxic agent or a radiotoxic agent.

Chemotherapeutic agents useful in the generation of such immunoconjugates are described herein. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, Phytolaca *americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. A variety of radioisotopes are available for the production of radioconjugate antibodies. Examples include, but are not limited to, $^{212}$Bi, $^{131}$I, $^{131}$In, $^{90}$Y and $^{186}$Re.

Conjugates of the antibodies specific for CEACAM1 described herein and a cytotoxic agent can be made using any of a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., 238 Science 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026.

In other embodiments, the CEACAM1-specific antibody or portion thereof can be conjugated to a "receptor" (e.g., streptavidin) for utilization in tumor pretargeting wherein the antibody-receptor conjugate is administered to the subject, followed by removal of unbound conjugate from the circulation using a clearing agent and then administration of a "ligand" (e.g., avidin) which is conjugated to a cytotoxic agent (e.g. a radionucleotide). In some embodiments, the CEACAM1-specific antibody or antibody fragment thereof can be conjugated to biotin, and the biotin conjugated antibody or antibody fragment thereof can be further conjugated or linked to a streptavidin-bound or -coated agent, such as a streptavidin-coated microbubble, for use in, for example, molecular imaging of angiogenesis.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

Immunoliposomes

The antibodies and antibody fragments thereof specific for CEACAM1 described herein can also be formulated as immunoliposomes. Liposomes containing the antibody are prepared by methods known in the art, such as described in Epstein et al., 82 PNAS 3688 (1985); Hwang et al., 77 PNAS 4030 (1980); and U.S. Pat. No. 4,485,045 and U.S. Pat. No. 4,544,545. Liposomes with enhanced circulation time are disclosed in U.S. Pat. No. 5,013,556.

Particularly useful liposomes can be generated, for example, by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the invention can be conjugated to the liposomes as described in Martin et al., 257 J. Biol. Chem. 286 (1982) via a disulfide interchange reaction. A chemotherapeutic agent is optionally contained within the liposome. See Gabizon et al., 81 J. Natl. Cancer Inst. 1484 (1989).

The host cell lines producing the recombinant 5F4, 34B1 and 26H7 antibodies are being maintained and stored.

Therapeutic & Diagnostics Uses of Anti-CEACAM1 Antibodies and Antigen-Binding Portions Thereof As demonstrated herein, the anti-CEACAM1 antibodies described herein are surprisingly effective at inhibiting and preventing cancer spreading and metastases. Accordingly, provided herein are novel pharmaceutical compositions and methods of inhibiting and/or preventing cancer, such as pancreatic cancer, using the anti-CEACAM1 recombinant, chimeric, humanized, and/or composite human antibodies described herein.

Antibody-based cancer therapies for other targets have been successfully introduced into the clinic and provide the benefits of higher specificity and lower side effect profile acompared to conventional drugs, in part because their mode of action relies on less toxic immunological anti-tumor mechanisms, such as complement activation and recruitment of cytotoxic immune cells. Other targets for antibodies which are either already approved or in clinical development for tumor therapy have distinct qualities. In the case of antibodies to the proteoglycan MUC-1, a peptide repeat epitope in the backbone of the target is underglycosylated in tumor cells and thus altered to its normal counterpart. In the case of antibodies to CD20 (rituximab), CD52 (Campath-1H) and CD22 (epratuzumab), antibody targets have comparable expression levels on tumor cells and normal lymphocytes. Another example of differential accessibility of antibody targets is carboanhydrase IX (CA9).

Eight antibodies have been approved for treatment of neoplastic diseases, most of them, however in lymphoma and leukemia (Adams, G. P. & Weiner, L. M. (2005) Nat. Biotechnol. 23, 1147-1157). Only three mAbs, namely Herceptin, Avastin and Erbitux, address solid cancer types, which account for more than 90% of cancer-evoked mortality. The substantial remaining medical need, the significant clinical benefit approved monoclonal antibodies have already provided, and their considerable commercial success together demonstrate the importance of identifying and characterizing new antibody-based therepaies for the treatment and inhibition of cancer (Brekke, O. H. & Sandlie, I. (2003) Nat. Rev. Drug Discov. 2, 52-62; Carter, P. (2001) Nat. Rev. Cancer 1, 118-129).

Accordingly, in some aspects, provided herein are methods to treat a subject having or at risk for a cancer or tumor comprising administering an effective amount of an anti-CEACAM1 antibody or antibody portion thereof. In some such embodiments of these methods for treating cancer, the anti-CEACAM1 antibody or antibody portion thereof is a recombinant anti-CEACAM1 antibody or portion thereof. In some such embodiments, the anti-CEACAM1 antibody or antibody-portion thereof comprises one or more heavy chain CDR regions comprising a sequence selected from the group consisting of SEQ ID NO:1, SEQ ID NO:2, and SEQ ID NO:3. In some such embodiments, the anti-CEACAM1 antibody or antibody-portion thereof comprises one or more light chain CDR regions comprising a sequence selected from the group consisting of SEQ ID NO:4, SEQ ID NO:5, and SEQ ID NO:6.

In some embodiments of these aspects and all such aspects described herein, the disease or disorder is cancer, particularly pancreatic cancer. Inhibition of tumor cell growth using the compositions and therapeutic methods described herein at the primary tumor site and secondary tumor site serve to prevent and limit metastasis and progression of disease.

In some embodiments of these aspects, the recombinant anti-CEACAM1 antibody is an antibody portion having specificity for the same epitope as the monoclonal anti-CEACAM1 antibody 5F4, and produced by hybridoma 5F4. In some such embodiments, the recombinant anti-CEACAM1 antibody is an antibody portion comprising one or more variable heavy chain CDR sequences selected from the group consisting of SEQ ID NO:1-SEQ ID NO:3 and/or one or more variable light chain CDR sequences selected from the the group consisting of SEQ ID NO:4-SEQ ID NO:6 of the recombinant monoclonal antibody. In some embodiments, the antibody portion is a Fab fragment. In some embodiments, the anti-CEACAM1 antibody portion is a Fab' fragment. In some embodiments, the anti-CEACAM1 antibody portion is a Fd fragment. In some embodiments, the anti-CEACAM1 antibody portion is a Fd' fragment. In some embodiments, the antibody portion is a Fv fragment. In some embodiments, the anti-CEACAM1 antibody fragment is a dAb fragment. In some embodiments, the anti-CEACAM1 antibody portion comprises isolated CDR regions. In some embodiments, the anti-CEACAM1 antibody portion is a F(ab')$_2$ fragment. In some embodiments, the anti-CEACAM1 antibody portion is a single chain antibody molecule. In some embodiments, the anti-CEACAM1 antibody portion is a diabody comprising two antigen binding sites. In some embodiments, the anti-CEACAM1 antibody portion is a linear antibody comprising a pair of tandem Fd segments ($V_H$—$C_H$1-$V_H$-$C_H$1).

The terms "cancer" and "cancerous" refer to or describe the physiological condition in mammals that is typically characterized by unregulated cell growth. Included in this definition are benign and malignant cancers, as well as dormant tumors or micrometastases. Accordingly, the terms "cancer" or "tumor" as used herein refers to an uncontrolled growth of cells which interferes with the normal functioning of the bodily organs and systems, including cancer stem cells and tumor vascular niches. A subject that has a cancer or a tumor is a subject having objectively measurable cancer cells present in the subject's body. Included in this definition are benign and malignant cancers, as well as dormant tumors or micrometastases. Cancers which migrate from their original location and seed vital organs can eventually lead to the death of the subject through the functional deterioration of the affected organs. Hematopoietic cancers, such as leukemia, are able to out-compete the normal hematopoietic compartments in a subject, thereby leading to hematopoietic failure (in the form of anemia, thrombocytopenia and neutropenia) ultimately causing death.

As demonstrated herein, the recombinant anti-CEACMA1 antibodies or antibody portions thereof, described herein, are surprisingly effective at inhibiting and preventing metastasis of pancreatic cancer. By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

In some embodiments of the methods described herein, a subject having a cancer or a tumor being administered the anti-CEACAM1 antibody or antibody portion thereof has or is at increased risk for pancreatic cancer. Pancreatic cancer is the fourth leading cause of cancer death in the USA and leads to an estimated 227000 deaths per year worldwide. Pancreatic ductal adenocarcinomas evolve through non-invasive precursor lesions, most typically pancreatic intraepithelial neoplasias, acquiring clonally selected genetic and epigenetic alterations along the way. Pancreatic cancers can also evolve from intraductal papillary mucinous neoplasms or mucinous cystic neoplasms. Risk factors for this malignant disease include smoking, family historyof chronic pancreatitis, advancing age, male sex, diabetes mellitus, obesity, non-O blood group, and occupational exposures (eg, to chlorinated hydrocarbon solvents and nickel), African-American ethnic origin, a high-fat diet, diets high in meat and low in vegetables and folate, and possibly *Helicobacter pylori* infection and periodontal disease (Vincent A, et al., Lancet. 2011 Aug. 13; 378(9791):607-20. Pancreatic cancer).

In some such embodiments, the subject having or at risk for pancreatic cancer has early stage pancreatic cancer. Early-stage pancreatic cancer is usually clinically silent, and disease typically only becomes apparent after the tumour invades surrounding tissues or metastasises to distant organs.

In some such embodiments, the subject having or at risk for pancreatic cancer has a pancreatic intraepithelial neoplasia (PanIN). As used herein, a pancreatic intraepithelial neoplasia (PanIN) is a neoplastic precursor to invasive adenocarcinoma of the pancreas and are microscopic tumors (<5 mm diameter) and are not directly visible by pancreatic imaging. PanINs can harbour the somatic genetic alterations seen in invasive pancreatic cancers, and prevalence of these genetic alterations rises as the amount of cytological and architectural atypia in PanINs increases. Low-grade PanINs (PanIN 1) are very common with increasing age and high-grade PanINs (PanIN 3) are usually present in pancreata with invasive cancer. Pancreata resected from individuals with a strong family history of pancreatic cancer usually have multifocal PanINs associated with lobulocentric atrophy.

In some such embodiments, the subject having or at risk for pancreatic cancer has an intraductal papillary mucinous neoplasm. Intraductal papillary mucinous neoplasm are a less frequent precursor to invasive pancreatic cancer, and they are large cystic neoplasms (≥5 mm) diagnosed increasingly because of improvements in pancreatic imaging. Non-invasive intraductal papillary mucinous neoplasms are classified on the basis of the amount of cytological and architectural dysplasia, as either low-grade, intermediate-grade, or high-grade dysplasia (carcinoma in situ). Cure rates are very high after resection of intraductal papillary mucinous neoplasms that do not have an associated invasive pancreatic cancer but, if left alone, these lesions can progress to incurable invasive cancers. Intraductal papillary mucinous neoplasms can affect pancreatic branch ducts, main ducts, or both. Most small asymptomatic intraductal papillary mucinous neoplasms in branch ducts have low malignant potential, so international guidelines have been developed for their management, and are known to those of skill in the art.

In some such embodiments, the subject having or at risk for pancreatic cancer has a mucinous cystic neoplasm, which is composed of mucin-producing epithelial cells and an associated ovarian-type stroma Unlike intraductal papillary mucinous neoplasms, mucinous cystic neoplasms do not communicate with pancreatic ducts. Mucinous cystic neoplasms arise predominantly in women; about a third of these neoplastic precursors have an associated invasive carcinoma In some such embodiments, the subject at increased risk for pancreatic cancer has a family history of pancreatic cancer. A family history of pancreatic cancer is an important risk factor for disease; about 7-10% of affected individuals have a family history. Familial pancreatic cancer in most studies refer to families in which a pair of first-degree relatives have been diagnosed with pancreatic tumours. Prospective analysis of families with this malignant disease shows that first-degree relatives of individuals with familial pancreatic cancer have a ninefold increased risk of this neoplasm over the general population. This risk rises to 32-fold greater in kindreds with three or more first-degree relatives with pancreatic cancer. Furthermore, evidence indicates that the risk of pancreatic cancer is modestly increased in first-degree relatives of patients with sporadic pancreatic cancer compared with the general population. Of kindreds with familial pancreatic cancer, risk is highest in those with a case of young-onset pancreatic cancer (age <50 years) in the family compared with those without a young-onset case. Patients with familial pancreatic cancer also have more precancerous lesions than those with sporadic pancreatic tumours and have an augmented risk of developing extra-pancreatic cancers (Vincent A, et al., Lancet. 2011 Aug. 13; 378(9791):607-20. Pancreatic cancer).

In some embodiments, the methods can further comprise first selecting, screening, or diagnosing the subject having or at increased risk for pancreatic cancer. In some such embodiments, the diagnosis of the subject can comprise administering to the subject an anti-CEACAM1 antibody or antibody portion thereof coupled to a label, for example, a radioactive label, or a label used for molecular imaging, as described elsewhere herein. In such embodiments, detection of the labeled anti-CEACAM1 antibody or antibody portion is indicative of the subject having a cancer or tumor.

In some such embodiments, the diagnosis of increased risk for pancreatic cancer can be determined by looking at one or more genetic mutations and/or disease conditions associated with increased risk for pancreatic cancer. Non-limiting examples of genetic mutations and/or disease conditions associated with increased risk for pancreatic cancer include: germline mutations in BRCA2, PALB2, CDKN2A, STK11, and PRSS1 genes, and Lynch syndrome, which are associated with a substantially increased risk of pancreatic cancer; germline BRCA2 gene mutations which account for the highest proportion of known causes of inherited pancreatic cancer and have been identified in 5-17% of families with familial pancreatic cancer, and are associated with 10% of unselected, apparently sporadic, pancreatic cancers in the Ashkenazi Jewish population; germline mutations in PALB2 (partner and localiser of BRCA2), which has been identified as a pancreatic cancer susceptibility gene and recorded in up to 3% of patients with familial pancreatic cancer; germline CDKN2A gene mutations, which are noted generally in families with familial atypical multiple-mole melanoma; germline STK11 mutations, which are found in patients with Peutz-Jeghers syndrome; germline PRSS1 mutations, which are found in people with hereditary pancreatitis; hereditary non-polyposis colon cancer patients, who have a modest increased risk of developing pancreatic cancer; and/or subjects with non-0 blood group.

In some such embodiments, the diagnosis of having pancreatic cancer or being at increased risk for pancreatic cancer can be determined by a blood marker associated with pancreatic cancer that can be measured non-invasively.

In some such embodiments, the diagnosis of having pancreatic cancer or being at increased risk for pancreatic cancer can be determined by endoscopic ultrasound, which has the ability to detect small preinvasive lesions, of about 1 cm. Focal preinvasive lesions evident by endoscopic ultrasound, such as intraductal papillary mucinous neoplasms, can be sampled, for example, by fine-needle aspiration.

In some such embodiments, the diagnosis of having pancreatic cancer or being at increased risk for pancreatic cancer can be determined by tri-phasic pancreatic-protocol CT.

In some embodiments of these methods, a subject having been diagnosed with pancreatic cancer or at increased risk for pancreatic cancer can further undergo one or more additional steps or procedures to detect metastases. In some such embodiments, the one or more additional steps to detect metastases comprises chest imaging, for example, chest radiography or CT, to detect pulmonary metastases. In some embodiments, the one or more additional steps to detect metastases comprises PET CT. In some embodiments, the one or more additional steps to detect metastases comprises laparoscopy to detect, for example, peritoneal metastases.

In some embodiments of these methods, a subject having been diagnosed with pancreatic cancer or at increased risk for pancreatic cancer can further undergo one or more additional steps or procedures to further confirm the presence of a malignant tumor. For example, cytological confirmation can be made with endoscopic ultrasound or CT-guided fine-needle aspiration. Sensitivity of endoscopic ultrasound-guided fine-needle aspiration of pancreatic masses is reported to be about 80%. Identification of the cause of biliary or pancreatic-duct strictures can require, in some embodiments, endoscopic retrograde cholangiopancreatography and brushings for cytological diagnosis.

A subject having or at increased risk for a pancreatic cancer to be treated using the compositions and methods described herein can further be staged according to guidelines known to those of ordinary skill in the art. For example, clinical staging guidelines are as follows: Local or resectable pancreatic cancer (about 10%, median survival 17-23 months), which can be further sub-divided into: Stage 0 (Tis, N0, M0); Stage IA (T1, N0, M0); Stage IB (T2, N0, M0); Stage IIA (T3, N0, M0); and Stage IIB (T1, N1, M0; T2, N1, M0; T3, N1, M0); Borderline resectable pancreatic cancer (10%, median survival up to 20 months), which refers to stage 3 disease with tumour abutment or <180° circumference of the superior mesenteric artery or coeliac arteries, or a short segment of hepatic artery or the superior mesenteric vein, pulmonary vein, or confluence of these veins; Locally advanced or unresectable pancreatic cancer (about 30%, median survival 8-14 months); Stage III pancreatic cancer (T4, any N, M0, where tumour encasement >180° circumference of the superior mesenteric artery or coeliac arteries, any unreconstructable venous involvement; and metastatic (about 60%, median survival 4-6 months); and Stage IV pancreatic cancer (any T, any N, M1), where T=primary tumour and TX indicates that the primary tumour cannot be assessed; T0 indicates no evidence of primary tumour; Tis indicates carcinoma in situ (includes the PanIN 3 classification); T1 indicates tumour restricted to the pancreas, ≤2 cm greatest dimension; T2 indicates tumour restricted to the pancreas, >2 cm greatest dimension; T3 indicates tumour extends beyond the pancreas, no involvement of coeliac axis or superior mesenteric artery (or extension to the portal vein or superior mesenteric artery, but still resectable); and T4 indicates tumour affects the coeliac axis or superior mesenteric artery (unresectable primary tumour); where N=regional lymph node and NX indicates regional lymph nodes cannot be assessed; N0 indicates no regional lymph-node metastasis; and N1 indicates regional lymph-node metastasis; and where M=distant metastasis and M0 indicates no distant metastasis and M1 indicates distant metastasis.

Efficacy of the Treatment

The efficacy of the treatment methods for cancer, such as pancreatic cancer, comprising therapeutic formulations of the compositions comprising the CEACAM1-specific antagonists described herein can be measured by various endpoints commonly used in evaluating cancer treatments, including but not limited to, tumor regression, tumor weight or size shrinkage, time to progression, duration of survival, progression free survival, overall response rate, duration of response, and quality of life. Because the CEACAM1-specific antagonists, e.g., recombinant anti-CEACAM1 antibodies and portions thereof, described herein, represent a unique class of anticancer drugs, they therefore can require unique measures and definitions of clinical responses to drugs. In the case of cancers, the therapeutically effective amount of the recombinant CEACAM1-antibody or portion thereof can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the recombinant CEACAM1-antibody or portion thereof act to prevent growth and/or kill existing cancer cells, it can be cytostatic and/or cytotoxic. For cancer therapy, efficacy in vivo can, for example, be measured by assessing the duration of survival, duration of progression free survival (PFS), the response rates (RR), duration of response, and/or quality of life.

In those embodiments related to the treatment or prevention of pancreatic cancer, symptoms associated with pancreatic cancer include, but are not limited to, abdominal or mid-back pain, obstructive jaundice, and weight loss. Weight loss can arise from anorexia, maldigestion from pancreatic ductal obstruction, and cachexia. Occasionally, pancreatic-duct obstruction can result in attacks of pancreatitis. Deep and superficial venous thrombosis is, in some embodiments, also a symptom of pancreatic cancer, and can be a sign of malignant disease. Gastric-outlet obstruction with nausea and vomiting sometimes happens with more advanced disease. In some embodiments, symptoms of pancreatic cancer to be inhibited or treated using the compositions and methods described herein include, but are not limited to, panniculitis and depression. In some embodiments, symptoms of pancreatic cancer to be inhibited or treated using the compositions and methods described herein include, but are not limited to, diabetes mellitus and/or impaired glucose tolerance.

In other embodiments, described herein are methods for increasing progression free survival of a human subject susceptible to or diagnosed with a cancer, such as pancreatic cancer. Time to disease progression is defined as the time from administration of the drug until disease progression or death. In a preferred embodiment, the combination treatment of the invention using a CEACAM1-specific antagonist, such as a recombinant anti-CEACAM1 antibody or portion thereof, and one or more chemotherapeutic agents may significantly increase progression free survival by at least about 1 month, 1.2 months, 2 months, 2.4 months, 2.9 months, 3.5 months, such as by about 1 to about 5 months, when compared to a treatment with chemotherapy alone. In another embodiment, the methods described herein may significantly increase response rates in a group of human subjects susceptible to or diagnosed with a cancer who are treated with various therapeutics. Response rate is defined as the percentage of treated subjects who responded to the treatment. In one embodiment, the combination treatment described herein using a CEACAM1-specific antagonist, such as a recombinant anti-CEACAM1 antibody or portion thereof, and one or more chemotherapeutic agents significantly increases response rate in the treated subject group compared to the group treated with chemotherapy alone.

For pancreatic cancer therapies, CT is the standard method for measurement of tumour burden, and clinical trials usually use RECIST (response evaluation criteria in solid tumours) criteria to gauge tumour response. In some embodiments related to treatment of pancreatic cancer, serial CA19-9 concentrations can be used to predict treatment response or disease relapse. In some embodiments, measurements of amounts of mutant DNA in plasma can be used to represent tumour burden and response to treatment.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a chronic immune condition, such as, but not limited to, a chronic infection or a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

For example, in some embodiments, the methods described herein comprise administering an effective amount of the recombinant anti-CEACAM1 antibodies or portions thereof, described herein, to a subject in order to alleviate a symptom of a cancer, such as pancreatic cancer. As used herein, "alleviating a symptom of a cancer" is ameliorating or reducing any condition or symptom associated with the cancer. As compared with an equivalent untreated control, such reduction or degree of prevention is at least 5%, 10%, 20%, 40%, 50%, 60%, 80%, 90%, 95%, or 100% as measured by any standard technique. Ideally, the cancer is completely cleared as detected by any standard method known in the art, in which case the cancer is considered to have been treated. A patient who is being treated for a cancer is one who a medical practitioner has diagnosed as having such a condition. Diagnosis can be by any suitable means. Diagnosis and monitoring can involve, for example, detecting the level of cancer cells in a biological sample (for example, a tissue or lymph node biopsy, blood test, or urine test), detecting the level of a surrogate marker of the cancer in a biological sample, detecting symptoms associated with the specific cancer, or detecting immune cells involved in the immune response typical of such a cancer.

The term "effective amount" as used herein refers to the amount of a recombinant anti-CEACAM1 antibody or portion thereof needed to alleviate at least one or more symptom of the disease or disorder, and relates to a sufficient amount of pharmacological composition to provide the desired effect, i.e., inhibit the formation of new blood vessels. The term "therapeutically effective amount" therefore refers to an amount of a recombinant anti-CEACAM1 antibody or portion thereof using the methods as disclosed herein, that is sufficient to effect a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". For any given case, however, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$. Compositions and methods that exhibit large therapeutic indices are preferred. A therapeutically effective dose can be estimated initially from cell culture assays. Also, a dose can be formulated in animal models to achieve a circulating plasma concentration range that includes the $IC_{50}$ (i.e., the concentration of the recombinant anti-CEACAM1 antibody or portion thereof), which achieves a half-maximal inhibition of symptoms as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

Modes of Administration

The CEACAM1-specific antagonist agents, such as recombinant anti-CEACMA1 antibodies or antibody portions thereof, described herein, can be administered to a subject in need thereof by any appropriate route which results in an effective treatment in the subject. As used herein, the terms "administering," and "introducing" are used interchangeably and refer to the placement of an anti-CEACAM1 antibody or antibody portion thereof into a subject by a method or route which results in at least partial localization of such agents at a desired site, such as a site of inflammation or cancer, such that a desired effect(s) is produced.

In some embodiments, the recombinant anti-CEACAM1 antibody or portion thereof is administered to a subject having a cancer, such as pancreatic cancer, to be inhibited by any mode of administration that delivers the agent systemically or to a desired surface or target, and can include, but is not limited to, injection, infusion, instillation, and inhalation administration. To the extent that anti-CEACAM1 antibodies or antibody fragments thereof can be protected from inactivation in the gut, oral administration forms are also contemplated. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the anti-CEACAM1 antibodies or antibody fragments thereof for use in the methods described herein are administered by intravenous infusion or injection.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of the bispecific or multispecific polypeptide agent other than directly into a target site, tissue, or organ, such as a tumor site, such that it enters the subject's circulatory system and, thus, is subject to metabolism and other like processes.

The CEACAM1-specific antagonists described herein are administered to a subject, e.g., a human subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration, for example, to a tumor or cancer site where angiogenesis is occurring, is particularly desired if extensive side effects or toxicity is associated with the use of the CEACAM1 antagonist. An ex vivo strategy can also be used for therapeutic applications in some embodiments. Ex vivo strategies involve transfecting or transducing cells obtained from a subject with a polynucleotide encoding a CEACAM1 antagonist. The transfected or transduced cells are then returned to the subject. The cells can be any of a wide range of types including, without limitation, hematopoietic cells (e.g., bone marrow cells, macrophages, monocytes, dendritic cells, T cells, or B cells), fibroblasts, epithelial cells, endothelial cells, keratinocytes, or muscle cells.

In some embodiments, when the CEACAM1-specific antagonist is an anti-CEACAM1 recombinant antibody or portion thereof, the antibody or portion thereof is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In some embodiments, the antibody or antibody fragment thereof is suitably administered by pulse infusion, particularly with declining doses of the antibody. Preferably the dosing is given by injections, most preferably intravenous or subcutaneous injections, depending in part on whether the administration is brief or chronic.

In some embodiments, the CEACAM1-specific antagonist compound is administered locally, e.g., by direct injections, when the disorder or location of the tumor permits, and the injections can be repeated periodically. The CEACAM1-specific antagonist can also be delivered systemically to the subject or directly to the tumor cells, e.g., to a tumor or a tumor bed following surgical excision of the tumor, in order to prevent or reduce local recurrence or metastasis, for example of a dormant tumor or micrometastases.

Antibody-targeted sonoporation methods are contemplated for use in some embodiments of the methods for inhibiting tumors described herein, in order to enhance the efficacy and potency of the therapeutic compositions comprising anti-CEACAM1 recombinant antibodies and portions thereof provided herein. As used herein, "sonoporation" refers to the use of sound, preferably at ultrasonic frequencies, or the interaction of ultrasound with contrast agents (e.g., stabilized microbubbles) for temporarily modifying the permeability of cell plasma membranes, thus allowing uptake of large molecules, such as therapeutic agents. The membrane permeability caused by the sonoporation is transient, leaving the agents trapped inside the cell after the ultrasound exposure. Sonoporation employs acoustic cavitation of microbubbles to enhance delivery of large molecules.

Accordingly, in some embodiments of the methods, therapeutic anti-CEACAM1 agents, such as the anti-CEACAM1 antibodies and portions thereof described herein, mixed with ultrasound contrast agents, such as microbubbles, can be injected locally or systemically into a subject in need of treatment for cancer, and ultrasound can be coupled and even focused into the defined area, e.g., tumor site, to achieve targeted delivery of the anti-CEACAM1 recombinant antibodies and portions thereof described herein.

In some embodiments, the methods use focused ultrasound methods to achieve targeted delivery of the anti-CEACAM1 antibodies and antibody fragments thereof described herein. As used herein, HIFU or "High Intensity Focused Ultrasound" refers to a non-invasive therapeutic method using high-intensity ultrasound to heat and destroy malignant or pathogenic tissue without causing damage to overlying or surrounding health tissue. As described in Khaibullina et al., 49 J. Nucl. Med. 295 (2008), and WO 2010127369, HIFU can also be used as a means of delivery of therapeutic agents, such as antibodies or antibody fragments thereof.

Methods using contrast-enhanced ultrasound (CEUS) are also contemplated for use with anti-CEACAM1 inhibiting agents described herein. Contrast-enhanced ultrasound (CEUS) refers to the application of ultrasound contrast medium and ultrasound contrast agents to traditional medical sonography. Ultrasound contrast agents refer to agents that rely on the different ways in which sound waves are reflected from interfaces between substances.

A variety of microbubble contrast agents are available for use with the compositions and methods described herein. Microbubbles can differ in their shell makeup, gas core makeup, and whether or not they are targeted. Targeting ligands that bind to receptors characteristic of angiogenic disorders, such as CEACAM1, can be conjugated to microbubbles, enabling the microbubble complex to accumulate selectively in areas of interest, such as diseased or abnormal tissues. This form of molecular imaging, known as targeted contrast-enhanced ultrasound, will only generate a strong ultrasound signal if targeted microbubbles bind in the area of interest. Targeted contrast-enhanced ultrasound has many applications in both medical diagnostics and medical therapeutics.

Accordingly, in some embodiments of the methods described herein, a recombinant anti-CEACAM1 antibody or antibody fragment thereof, such as, for example, an anti-CEACAM1 recombinant antibody or portion thereof, comprising one or more heavy chain CDR regions comprising a sequence selected from the group consisting of SEQ ID NO:1, SEQ ID NO:2, SEQ ID NO:3, SEQ ID NO:7, SEQ ID NO:8, SEQ ID NO:9, SEQ ID NO:13, SEQ ID NO:14, or SEQ ID NO:15; an anti-CEACAM1 antibody or antibody-fragment thereof comprising one or more light chain CDR regions comprising a sequence selected from the group consisting of SEQ ID NO:4, SEQ ID NO:5, SEQ ID NO:6, SEQ ID NO:10, SEQ ID NO:11, SEQ ID NO:12, SEQ ID NO:16, SEQ ID NO:17, SEQ ID NO:18, SEQ ID NO:19, SEQ ID NO:20, or SEQ ID NO:21; an anti-CECAM1 antibody or antibody-fragment comprising a variable heavy ($V_H$) chain amino acid sequence selected from the group consisting of SEQ ID NO:26, SEQ ID NO:28, or SEQ ID NO:30; and/or an anti-CEACAM1 antibody or antibody-fragment thereof comprising a variable light ($V_L$) chain amino acid sequence selected from the group consisting of SEQ ID NO:27, SEQ ID NO:29, SEQ ID NO:31, or SEQ ID NO:32, is administered to a subject in need of treatment for a cancer or a tumor, such as pancreatic cancer, using a targeted ultrasound delivery. In some such embodiments, the targeted ultrasound delivery comprises using microbubbles as contrast agents to which an anti-CEACAM1 antibody or antibody fragment thereof. In some such embodiments, the targeted ultrasound is HIFU.

Pharmaceutical Formulations

For the clinical use of the methods described herein, administration of the CEACAM1 antagonists, such as the recombinant anti-CEACAM1 antibodies or portions thereof described herein, can include formulation into pharmaceutical compositions or pharmaceutical formulations for parenteral administration, e.g., intravenous; mucosal, e.g., intranasal; ocular, or other mode of administration. In some embodiments, the anti-CEACAM1 antibodies or antibody fragments thereof described herein can be administered along with any pharmaceutically acceptable carrier compound, material, or composition which results in an effective treatment in the subject. Thus, a pharmaceutical formulation for use in the methods described herein can contain an anti-CEACAM1 antibody or antibody fragment thereof as described herein in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, an anti-CEACAM1 antibody or portion thereof. Each carrier must be "acceptable" in the sense of being compatible with the other ingredients of the formulation and not injurious to the patient. The terms "excipient", "carrier", "pharmaceutically acceptable carrier", or the like are used interchangeably herein.

The recombinant anti-CEACAM1 antibodies or portions thereof described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally, a recombinant anti-CEACAM1 antibody or portion thereof can be implanted into a patient or injected using a drug delivery system. See, e.g., Urquhart et al., 24 Ann. Rev. Pharmacol. Toxicol. 199 (1984); CONTROLLED RELEASE OF PESTICIDES & PHARMACEUTICALS (Lewis, ed., Plenum Press, New York, 1981); U.S. Pat. No. 3,773,919, U.S. Pat. No. 3,270,960.

Therapeutic formulations of the CEACAM1-specific antagonist agents, such as recombinant anti-CEACAM1 antibodies or portions thereof, described herein can be prepared for storage by mixing a CEACAM1-specific antagonist having the desired degree of purity with optional pharmaceutically acceptable carriers, excipients or stabilizers (Remington's Pharmaceutical Sciences 16th edition, Osol, ed., 1980), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Optionally, the formulations comprising the compositions described herein contain a pharmaceutically acceptable salt, typically, e.g., sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. Optionally, the formulations of the invention can include a pharmaceutically acceptable surfactant at a concentration of 0.005 to 0.02%.

The therapeutic formulations of the compositions comprising CEACAM1-specific antagonists, such as recombinant anti-CEACAM1 antibodies and portions thereof, described herein, can also contain more than one active compound as necessary for the particular indication being treated, preferably those with complementary activities that do not adversely affect each other. Alternatively, or in addition, the composition can comprise a cytotoxic agent, cytokine, growth inhibitory agent and/or an angiogenesis inhibitor such as a VEGFR antagonist. Such molecules are suitably present in combination in amounts that are effective for the purpose intended.

The active ingredients of the therapeutic formulations of the compositions comprising CEACAM1-specific antagonists described herein can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (16th ed., Osol, ed., 1980).

In some embodiments, sustained-release preparations can be used. Suitable examples of sustained-release preparations include semipermeable matrices of solid hydrophobic polymers containing the CEACAM1-specific antagonist, such as a recombinant anti-CEACAM1 antibody, in which the matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

The therapeutic formulations to be used for in vivo administration, such as parenteral administration, in the methods described herein can be sterile, which is readily accomplished by filtration through sterile filtration membranes, or other methods known to those of skill in the art.

Dosages and Duration

The CEACAM1-specific antagonists described herein, such as recombinant anti-CEACAM1 antibodies and antibody fragments thereof, are formulated, dosed, and administered in a fashion consistent with good medical practice. Factors for consideration in this context include the particular disorder being treated, the particular subject being treated, the clinical condition of the individual subject, the cause of the disorder, the site of delivery of the agent, the method of administration, the scheduling of administration, and other factors known to medical practitioners. The "therapeutically effective amount" of the CEACAM1-specific antagonist to be administered will be governed by such considerations, and refers to the minimum amount necessary to ameliorate, treat, or stabilize, the cancer; to increase the time until progression (duration of progression free survival) or to treat or prevent the occurrence or recurrence of a tumor, a dormant tumor, or a micrometastases. The CEACAM1-specific antagonist is optionally formulated with one or more additional therapeutic agents currently used to prevent or treat cancer or a risk of developing a cancer. The effective amount of such other agents depends on the amount of CEACAM1-specific antagonist present in the formulation, the type of disorder or treatment, and other factors discussed above. These are generally used in the same dosages and with administration routes as used herein before or about from 1 to 99% of the heretofore employed dosages.

Depending on the type and severity of the disease, about 1 μg/kg to 100 mg/kg (e.g., 0.1-20 mg/kg) of a CECAM1-specific antagonist is an initial candidate dosage for administration to a subject, whether, for example, by one or more separate administrations, or by continuous infusion. A typical daily dosage might range from about 1 μg/kg to about 100 mg/kg or more, depending on the factors mentioned above. Typical dosages include, for example, 5 mg/kg, 7.5 mg/kg, 10 mg/kg, and 15 mg/kg. For repeated administrations over several days or longer, depending on the condition, the treatment is sustained until, for example, the cancer is treated, as measured by the methods described above or known in the art. However, other dosage regimens can be useful. In one non-limiting example, if the CEACAM1-specific antagonist is an anti-CEACAM1 antibody or antibody fragment thereof, the anti-CEACAM1 antibody or antibody fragment thereof is administered once every week, every two weeks, or every three weeks, at a dose range from about 5 mg/kg to about 15 mg/kg, including but not limited to 5 mg/kg, 7.5 mg/kg, 10 mg/kg or 15 mg/kg. The progress of using the methods described herein can be easily monitored by conventional techniques and assays.

The duration of a therapy using the methods described herein will continue for as long as medically indicated or until a desired therapeutic effect (e.g., those described herein) is achieved. In certain embodiments, the CEACAM1-specific antagonist therapy, such as a CEACAM1-specific recombinant antibody or portion thereof, described herein, is continued for 1 month, 2 months, 4 months, 6 months, 8 months, 10 months, 1 year, 2 years, 3 years, 4 years, 5 years, 10 years, 20 years, or for a period of years up to the lifetime of the subject.

Combination Therapies

The methods provided herein for inhibiting or treating cancer in subject having or at risk for cancer by administering to the subject a therapeutically effective amount of a composition comprising an angiogenesis-inhibiting amount of an anti-CEACAM1 inhibitor, such as a recombinant anti-CEACAM1 antibody or portion thereof, can, in some embodiments, further comprise administration one or more additional treatments such as angiogenic inhibitors, chemotherapy, radiation, surgery, or other treatments known to those of skill in the art to inhibit angiogenesis.

In some embodiments, the methods described herein further comprise administration of a combination of at least one CEACAM1-specific antagonist, such a recombinant anti-CEACAM1 antibody or portion thereof, with one or more additional anti-cancer therapies. Examples of additional anti-cancer therapies include, without limitation, surgery, radiation therapy (radiotherapy), biotherapy, immunotherapy, chemotherapy, or a combination of these therapies. In addition, cytotoxic agents, anti-angiogenic and anti-proliferative agents can be used in combination with the CEACAM1-specific antagonist.

In certain embodiments of any of the methods and uses, the invention provides treating cancer by administering effective amounts of a recombinant anti-CEACAM1 antibody and one or more chemotherapeutic agents to a subject susceptible to, or diagnosed with, locally recurrent or previously untreated cancer. A variety of chemotherapeutic agents can be used in the combined treatment methods and uses of the invention. An exemplary and non-limiting list of chemotherapeutic agents contemplated for use in the methods described herein is provided under "Definitions," or described herein.

In those embodiments related to pancreatic cancer, the methods can further comprise one or more additional therapeutic treatments used in pancreatic cancer treatment and therapies. In some such embodiments, the therapeutic treatment is surgery or pancreatic resection. In some embodiments, the pancreatic resection is performed before or prior to administration of the effective amounts of a recombinant anti-CEACAM1 antibody, as described herein. In some embodiments, the pancreatic resection is performed after administration of the effective amounts of a recombinant anti-CEACAM1 antibody has commenced. In some embodiments, the pancreatic resection is performed concurrently with administration of the effective amounts of a recombinant anti-CEACAM1 antibody. In some embodiments, the pancreatic resection involves portal or superior mesenteric vein resection and reconstruction. In some embodiments, laparoscopic resection is used. In some such embodiments, endoscopic tattooing can be used to localise small lesions before laparoscopic resection. Postoperative complications after resection can include pancreatic anastomotic leaks and delayed gastric emptying.

In those embodiments related to pancreatic cancer, the methods can further comprise pathological assessment of the pancreatic cancer prior to, during, and/or subsequent to the administration of the recombinant anti-CEACAM1 antibody. As known to one of ordinary skill in the art, pathological assessment of a pancreatic tumor, such as a resected pancreatic tumour, provides important prognostic information. Pathological assessment includes classification of histological variants of pancreatic ductal adenocarcinoma. Such variants include colloid carcinomas (associated with intestinal-type intraductal papillary mucinous neoplasms), medullary cancers (which can have microsatellite instability), and others including adenosquamous tumours, hepatoid carcinoma, signet-ring cell cancer, undifferentiated carcinoma, and undifferentiated carcinoma with osteoclast-like giant cells. In some such embodiments, molecular assessment of known pancreatic cancer markers can also be performed, such as by performing SMAD4 immunolabelling, which has been associated with increased risk of development of widespread metastasis and poor outcome after surgical resection; SPARC expression in fibroblasts, which has been associated with adverse outcomes.

In some embodiments related to methods for treating or inhibiting pancreatic cancer, the one or more additional therapeutic treatements can comprise adjuvant therapy. Such adjuvant therapies include, but are not limited to, gemcitabine; chemoradiation; fluorouracil-based chemoradiation; gemcitabine with fluorouracil before and after fluorouracil-based chemoradiation; compbination of interferon alfa-2b, cisplatin, and continuous-infusion fluorouracil concurrently with external-beam radiation; erlotinib; combination of gemcitabine, docetaxel, and capecitabine; combination of fluorouracil, folinic acid, irinotecan, and oxaliplatin; combination of gemcitabine and the epidermal growth factor receptor (EGFR) inhibitor, erlotinib; granulocyte-macrophage colony-stimulating factor-secreting vaccine for pancreatic cancer, with or without cyclophosphamide as a T regulatory-depleting agent; and/or any combination thereof.

In some embodiments related to methods for treating or inhibiting pancreatic cancer, the one or more additional therapeutic treatments involves radiation therapy. In the treatment of pancreatic cancer, fractionated radiation therapy is typically delivered as 45-60 Gy over about 6 weeks (1.8-2.0 Gy/day), with fluorouracil or capecitabine— an oral fluoropyrimidine—as a radiosensitiser. In the adjuvant setting, 45 Gy is delivered initially to the tumour bed, surgical anastomosis, and regional lymph nodes. Subsequently, additional radiation (about 5-15 Gy) can be directed at the tumour bed to target microscopic extension. Preoperative CT scans (with oral and intravenous contrast) and surgical clips can be used to calculate optimum volume and localisation of radiation.

In some embodiments of the methods for treating or inhibiting pancreatic cancer, the one or more additional therapeutic treatments comprises a PARP inhibitor, such as olaparib. Pancreatic cancer cells with defects in the BRCA2-PALB2-Fanconi DNA repair pathway have been shown to be sensitive to poly (ADP-ribose) polymerase (PARP) inhibitors.

In some embodiments of the methods for treating or inhibiting pancreatic cancer, the one or more additional therapeutic treatments comprises a hedgehog pathway inhibitor. For example, the hedgehog pathway inhibitor GDC-0449 (Genentech, San Francisco, Calif., USA), which is under investigation in a phase 2 clinical trial, in combination with gemcitabine and the nanoparticle formulation of paclitaxel, in patients with metastatic pancreatic adenocarcinoma. Other therapeutic agents that can be used in the methods for treating or inhibiting pancreatic cancer described herein include the multikinase inhibitor, sorafenib, and agents targeting SRC (dasatinib), y secretase, MTOR, TNFSF10 (also known as TRAIL), and IGF1.

In some embodiments of these methods, endoscopic treatments can be used to deliver or adminster the CEACAM1-specific antagonist and/or one or more additional therapeutic agents, including, but not limited to, endoscopic delivery of chemotherapy, cryotherapy, photodynamic therapy, and/or radiofrequency ablation.

In some embodiments, the methods described herein comprise administration of a CEACAM1-specific antagonist with one or more chemotherapeutic agents (e.g., a cocktail) or any combination thereof. In certain embodiments, the chemotherapeutic agent is for example, capecitabine, taxane, anthracycline, paclitaxel, docetaxel, paclitaxel protein-bound particles (e.g., Abraxane™) doxorubicin, epirubicin, 5-fluorouracil, cyclophosphamide or combinations thereof therapy. As used herein, combined administration includes simultaneous administration, using separate formulations or a single pharmaceutical formulation, and consecutive administration in either order, wherein preferably there is a time period while both (or all) active agents simultaneously exert their biological activities. Preparation and dosing schedules for such chemotherapeutic agents can be used according to manufacturers' instructions or as determined empirically by the skilled practitioner. Preparation and dosing schedules for chemotherapy are also described in Perry, CHEMOTHERAPY SERVICE ED. (Williams & Wilkins, Baltimore, Md., 1992). Accordingly, in some embodiments, the chemotherapeutic agent can precede, or follow administration of the CECAM1-specific antagonist or can be given simultaneously therewith.

In some other embodiments of the methods described herein, other therapeutic agents useful for combination tumor therapy with the CEACAM1 antagonists, such as recombinant antibodies, of the invention include antagonists of other factors that are involved in tumor growth, such as EGFR, ErbB2 (also known as Her2), ErbB3, ErbB4, or TNF. In some embodiments, it can be beneficial to also administer one or more cytokines to the subject. In some embodiments, the CEACAM1 antagonist is co-administered with a growth inhibitory agent. For example, the growth inhibitory agent can be administered first, followed by the CEACAM1 antagonist. Simultaneous administration or administration of the CEACAM1 antagonist first is also contemplated. Suitable dosages for the growth inhibitory agent are those presently used and can be lowered due to the combined action (synergy) of the growth inhibitory agent and CEACAM1 antagonist.

Examples of angiogenic inhibitors that can be used in combination with the CEACAM1 inhibitors, such as recombinant anti-CEACAM1 antibodies and portions thereof, described herein include, but are not limited to: direct angiogenesis inhibitors, Angiostatin, Bevacizumab (AVASTIN®), Arresten, Canstatin, Combretastatin, Endostatin, NM-3, Thrombospondin, Tumstatin, 2-methoxyestradiol, cetuximab (ERBITUX®), panitumumab (VECTIBIX™), trastuzumab (HERCEPTIN®) and Vitaxin; and indirect angiogenesis inhibitors: ZD1839 (Iressa), ZD6474, OS1774 (TARCEVA), CI1033, PKI1666, IMC225 (Erbitux), PTK787, SU6668, SU11248, Herceptin, and IFN-α, CELEBREX® (Celecoxib), THALOMID® (Thalidomide), and IFN-α. In some embodiments, the angiogenesis inhibitors for use in the methods described herein include but are not limited to small molecule tyrosine kinase inhibitors (TKIs) of multiple pro-angiogenic growth factor receptors. The three TKIs that are currently approved as anti-cancer therapies are erlotinib (TARCEVA®), sorafenib (NEXAVAR®), and sunitinib (SUTENT®).

In some embodiments, the angiogenesis inhibitors for use in the methods described herein include but are not limited to inhibitors of mTOR (mammalian target of rapamycin) such as temsirolimus (TORICEL™), bortezomib (VELCADE®), thalidomide (THALOMID®), and Doxycyclin.

In other embodiments, the angiogenesis inhibitors for use in the methods described herein include anti-angiogenic factors such as alpha-2 antiplasmin (fragment), angiostatin (plasminogen fragment), antiangiogenic antithrombin III, cartilage-derived inhibitor (CDI), CD59 complement fragment, endostatin (collagen XVIII fragment), fibronectin fragment, gro-beta (a C—X—C chemokine), heparinases heparin hexasaccharide fragment, human chorionic gonadotropin (hCG), interferon alpha/beta/gamma, interferon inducible protein (IP-10), interleukin-12, kringle 5 (plasminogen fragment), beta-thromboglobulin, EGF (fragment), VEGF inhibitor, endostatin, fibronection (45 kD fragment), high molecular weight kininogen (domain 5), NK1, NK2, NK3 fragments of HGF, PF-4, serpin proteinase inhibitor 8, TGF-beta-1, thrombospondin-1, prosaposin, p53, angioarrestin, metalloproteinase inhibitors (TIMPs), 2-Methoxyestradiol, placental ribonuclease inhibitor, plasminogen activator inhibitor, prolactin 16 kD fragment, proliferin-related protein (PRP), retinoids, tetrahydrocortisol-S transforming growth factor-beta (TGF-beta), vasculostatin, and vasostatin (calreticulin fragment), pamidronate thalidomide, TNP470, the bisphosphonate family such as aminobisphosphonate zoledronic acid. bombesin/gastrin-releasing peptide (GRP) antagonists such as RC-3095 and RC-3940-II (Bajol et. al., 90 British J. Cancer 245 (2004), anti-VEGF peptide RRKRRR (dRK6) (SEQ ID NO: 40) (Yoo, 174 J. Immunol. 5846 (2005).

Thus, in connection with the administration of a CEACAM1 inhibitor, such as recombinant anti-CEACAM1 antibodies and portions thereof, a compound which inhibits angiogenesis indicates that administration in a clinically appropriate manner results in a beneficial effect for at least a statistically significant fraction of patients, such as improvement of symptoms, a cure, a reduction in disease load, reduction in tumor mass or cell numbers, extension of life, improvement in quality of life, or other effect generally recognized as positive by medical doctors familiar with treating the particular type of disease or condition, e.g., pancreatic cancer.

The CEACAM1-specific antagonist and the one or more other therapeutic agents can be administered simultaneously or sequentially in an amount and for a time sufficient to reduce or eliminate the occurrence or recurrence of a tumor, a dormant tumor, or a micrometastases. The CEACAM1-specific antagonist and the one or more other therapeutic agents can be administered as maintenance therapy to prevent or reduce the likelihood of recurrence of the tumor.

As will be understood by those of ordinary skill in the art, the appropriate doses of chemotherapeutic agents or other anti-cancer agents will be generally around those already employed in clinical therapies, e.g., where the chemotherapeutics are administered alone or in combination with other chemotherapeutics. Variation in dosage will likely occur depending on the condition being treated. The physician administering treatment will be able to determine the appropriate dose for the individual subject.

In addition to the above therapeutic regimes, the subject can be subjected to radiation therapy.

In certain embodiments of any of the methods, uses and compositions described herein, the administered recombinant CEACAM1 antibody is an intact, naked antibody. In some embodiments, the recombinant CEACAM1 antibody can be conjugated with a cytotoxic agent. In certain embodiments of any of the methods and uses, the conjugated CEACAM1 antibody and/or CEACAM1 antibody portion thereof is/are internalized by the cell, resulting in increased therapeutic efficacy of the conjugate in killing the cancer cell to which it binds. In some embodiments, the cytotoxic agent conjugated to the CEACAM1 recombinant antibody and/or CEACAM1 antibody portion thereof targets or interferes with nucleic acid in the cancer cell. Examples of such cytotoxic agents include maytansinoids, calicheamicins, ribonucleases and DNA endonucleases, and are further described elsewhere herein.

Embodiments of the various aspects described herein can be illustrated by the following numbered paragraphs:

1. An isolated CEACAM1-specific recombinant monoclonal antibody or an antigen-binding portion thereof, comprising: at least one light chain component and at least one heavy chain component, wherein said heavy chain component comprises the amino acids of SEQ ID NO:26, SEQ ID NO:28, or SEQ ID NO:30; and said light chain component comprises the amino acids of SEQ ID NO:27, SEQ ID NO:29, SEQ ID NO:31 or SEQ ID NO:32, and wherein said antibody or an antigen-binding portion thereof binds the antigen recognized by the monoclonclal antibody 5F4, 34B1, or 26H7.
2. The isolated CEACAM1-specific recombinant monoclonal antibody or an antigen-binding portion thereof of paragraph 1, wherein the anti-CEACAM1-specific recombinant monoclonal antibody is a humanized antibody or portion thereof.
3. A chimeric antibody comprising the variable regions of the heavy and light chains of the recombinant antibody as described in paragraph 1 linked to the human immunoglobulin gamma-1 and kappa constant regions, respectively.
4. An isolated recombinant antibody or antigen-binding portion thereof comprising: a heavy chain complementarity determining region (CDR) 1 consisting of the amino acid residues of SEQ ID NO: 1, a heavy chain CDR2 consisting of the amino acid residues of SEQ ID NO: 2, a heavy chain CDR3 consisting of the amino acid residues of SEQ ID NO: 3, a light chain CDR1 consisting of the amino acid residues of SEQ ID NO: 4, a light chain CDR2 consisting of the amino acid residues of SEQ ID NO: 5, and a light chain CDR3 consisting of the amino acid residues of SEQ ID NO: 6, such that said isolated recombinant antibody or antigen-binding portion thereof binds the antigen recognized by 5F4.
5. An isolated recombinant antibody or antigen-binding portion thereof comprising: a heavy chain complementarity determining region (CDR) 1 consisting of the amino acid residues of SEQ ID NO: 1, SEQ ID NO: 7, or SEQ ID NO: 13; a heavy chain CDR2 consisting of the amino acid residues of SEQ ID NO:2, SEQ ID NO: 8, or SEQ ID NO: 14; a heavy chain CDR3 consisting of the amino acid residues of SEQ ID NO: 3, or SEQ ID NO: 9, or SEQ ID NO: 15; a light chain CDR1 consisting of the amino acid residues of SEQ ID NO: 4, SEQ ID NO:10, SEQ ID NO:16, or SEQ ID NO:19; a light chain CDR2 consisting of the amino acid residues of SEQ ID NO:5, SEQ ID NO:10, SEQ ID NO:17, or SEQ ID NO:20; and a light chain CDR3 consisting of the amino acid residues SEQ ID NO: 6, SEQ ID NO: 12, SEQ ID NO: 18, or SEQ ID NO: 21; such that said isolated recombinant antibody or antigen-binding portion thereof binds the antigen recognized by 5F4, 34B1, or 26H7.
6. The isolated CEACAM1-specific recombinant monoclonal antibody or an antigen-binding portion thereof of any one of paragraphs 4 or 5, wherein the antibody portion is a Fab fragment, a Fab' fragment, a Fd fragment, a Fd' fragment, a Fv fragment, a dAb fragment, a F(ab')$_2$ fragment, a single chain fragment, a diabody, or a linear antibody.
7. A diagnostic kit comprising the antibody of any one of the preceding paragraphs.
8. A composition comprising the antibody of any one of the preceding paragraphs and a carrier.
9. The antibody of any one of the preceding paragraphs, wherein said antibody is linked to a label.
10. The isolated CEACAM1-specific recombinant monoclonal antibody or an antigen-binding portion thereof of any one of the preceding paragraphs, further comprising an agent conjugated to the anti-CEACAM1 recombinant antibody or portion thereof to form an immunoconjugate specific for CEACAM1.
11. The isolated CEACAM1-specific recombinant monoclonal antibody or an antigen-binding portion thereof of paragraph 10, wherein the agent conjugated to the antibody or antibody fragment thereof is a chemotherapeutic agent, a toxin, a radioactive isotope, a small molecule, an siRNA, a nanoparticle, or a microbubble.
12. A pharmaceutical composition comprising the recombinant anti-CEACAM1 antibody or portion thereof that specifically binds to CEACAM1 of any one of the preceding paragraphs, and a pharmaceutically acceptable carrier.
13. A method of treating pancreatic cancer, the method comprising administering to a subject in need thereof a therapeutically effective amount of a pharmaceutical composition of paragraph 12.
14. A method of inhibiting tumor cell invasiveness in a subject having a cancer or a tumor, the method comprising administering to a subject in need thereof a therapeutically effective amount of a pharmaceutical composition of paragraph 12.
15. The method of any one of paragraphs 13 or 14, wherein the method further comprises the administration of one or more chemotherapeutic agents, angiogenesis inhibitors, cytotoxic agents, or anti-proliferative agents.
16. A method of inhibiting tumor growth and reducing tumor size or tumor metastasis in a subject in need thereof by inhibiting CEACAM1 expression and/or function in a cell, the method comprising administering to a subject in need thereof a therapeutically effective amount of a pharmaceutical composition of paragraph 12.
17. A method of inhibiting cancer progression by inhibiting CEACAM1 expression and/or function in a tumor cell, the method comprising administering to a subject in need thereof a therapeutically effective amount of the pharmaceutical composition of paragraph 12.
18. A method for combining CEACAM1-targeted molecular imaging and CEACAM1-targeted delivery of a therapeutic agent, the method comprising administering to a subject an effective amount of a therapeutic agent and the pharmaceutical composition of paragraph 12 conjugated to a targeting moiety, and determining the presence or absence of the pharmaceutical composition of paragraph 12 conjugated to the targeting moiety using molecular imaging.
19. The method of paragraph 18, wherein the therapeutic agent is a chemotherapeutic agent, a small molecule, a peptide, or an aptamer.
20. A pharmaceutical composition of paragraph 12 for use in inhibiting tumor cell invasiveness in a subject having pancreatic cancer or a pancreatic tumor.

21. The pharmaceutical composition of paragraph 20, further comprising one or more chemotherapeutic agents, angiogenesis inhibitors, cytotoxic agents, or anti-proliferative agents.
22. The pharmaceutical composition of paragraph 21, wherein the therapeutic agent is a chemotherapeutic agent, a small molecule, a peptide, or an aptamer.
23. A pharmaceutical composition of paragraph 12 for use in inhibiting tumor growth and reducing tumor size or tumor metastasis by inhibiting CEACAM1 expression and/or function in a cell in a subject in need thereof.
24. A pharmaceutical composition of paragraph 12 for use in inhibiting cancer progression by inhibiting CEACAM1 expression and/or function in a tumor cell in a subject in need thereof.
25. An isolated oligonucleotide comprising nucleotides of the sequence of SEQ ID NO: 33, wherein said oligonucleotide encodes the variable regions of the heavy chain of the 5F4 antibody.
26. An isolated oligonucleotide comprising nucleotides of the sequence of SEQ ID NO: 34, wherein said oligonucleotide encodes the variable regions of the light chain of the 5F4 antibody.
27. An isolated expression vector comprising an oligonucleotide of any one of paragraphs 25 or paragraph 26.
28. An isolated host cell or isolated host cell population comprising the expression vector of paragraph 27.

This invention is further illustrated by the following examples which should not be construed as limiting.

EXAMPLES

Example 1

Treatment and Prevention of Pancreatic Cancer by 5F4 Antibody

FIG. 1 demonstrates that 5F4 mouse anti-human CEACAM1 monoclonal antibody protects Rag2-deficient mice from human pancreatic cell line (AsPc-1) micrometastasis. Early detection of AsPc1 tumor cells with a non-invasive photosensitizaion method after intravenous injection is shown. The human pancreatic cancer cell line, AsPc-1 ($0.5 \times 10^6$ cells), was administered by tail-vein injection. After 14 days, animals received an oral dose of delta-aminolevulinic acid (ALA; 100 mg/kg) 4-6 hours prior to sacrifice by euthanasia and analysis of tissue fluorescence. Animals were then maintained under subdued light conditions to avoid photobleaching and phototoxic reactions. The abdominal and thoracic cavities of the animals were examined immediately under white light and then illuminated by UV light (405 nm) to evaluate the presence of tumors in the parenchyma of the lungs and the lymph nodes as evidence of metastasis. Note the hemorrhagic lung in the MOPC treated control (top) but normal, nonhemorrhagic appearing lung in the 5F4 treated animal (bottom), indicative of parenchymal injury due to the presence of tumor cells. Schematic diagram of ALA metabolism is shown on the right.

Figure 2A:
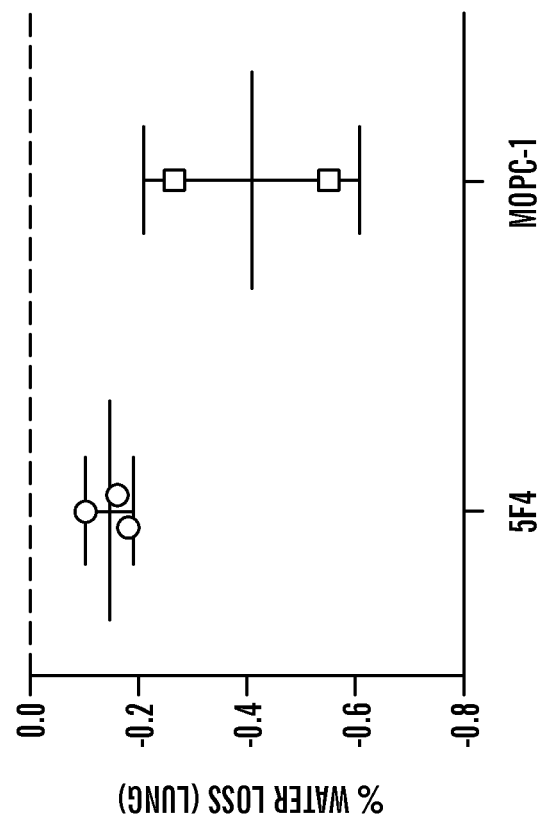
FIGS. 2A-2B demonstrate that 5F4 mouse anti-human CEACAM1 monoclonal antibody protects Rag2-deficient mice from human pancreatic cell line (AsPc-1) micrometastasis. Examination of lungs 14 days after intravenous inoculation of AsPc1 cell line as in FIG. 1.
Figure 2B:
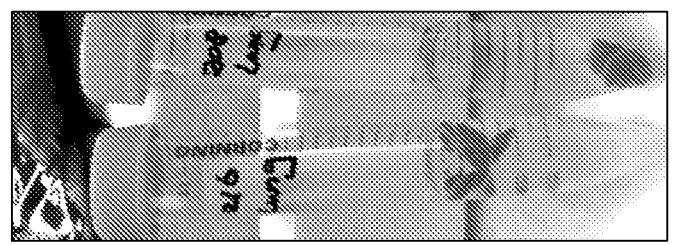

FIGS. 2A-2B demonstrate that 5F4 mouse anti-human CEACAM1 monoclonal antibody protects Rag2-deficient mice from human pancreatic cell line (AsPc-1) micrometastasis. Examination of lungs 14 days after intravenous inoculation of AsPc1 cell line as in FIG. 1. FIG. 2A demonstrates water retention capability. Lungs are spongy lobes inside the chest. Water retention is one of the routine methods for demonstrating lung damage (e.g., inflammation, edema, congestion). To measure water retention, one of the five lobes from MOPC- and 5F4-treated animals were excised, weighed and maintained in a glass desiccation cabinet for 14-18 days. After desiccation the lungs were weighed again and the difference is shown as percent water loss. There is barely any water loss of the lungs in the 5F4 treated mice but considerable water loss in the MOPC-1 treated mice. FIG. 2B shows collapsed lung in MOPC treated animals (15 ml conical, right). Lungs possess air pockets. Damaged lungs often have loss of air and elasticity. Air within a normal lung results in increased buoyancy. To measure lung damage by buoyancy, four of the five lobes from the mouse anti-human CEACAM1 monoclonal antibody 5F4-(in this case, Nr. 216, left), and MOPC treated animals (in this case, Nr. 208, right) treated animals were excised, rinsed with distilled water and floated in PBS buffer for no less than 2 hours. Healthy lungs float (5F4 mouse anti-human CEACAM1 monoclonal treated) and the collapsed lungs (MOPC antibody treatment) sink.

Figure 3:
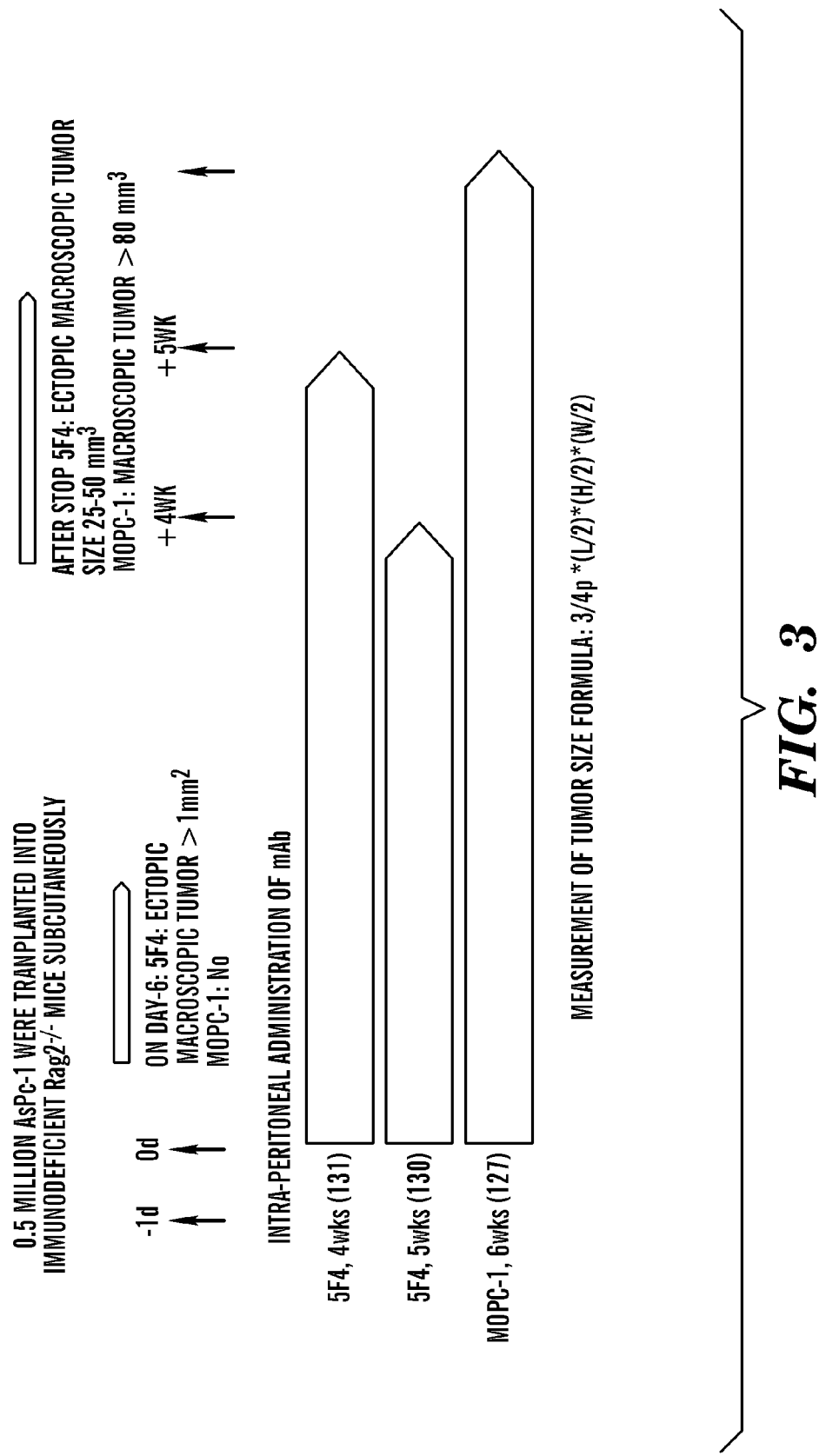
FIG. 3 depicts an in vivo metastasis model used in experiments described herein. The human pancreatic cancer cell line, AsPc-1, was established as xenografts by injection subcutaneously into the flanks of Rag2$^{-/-}$ mice. Anti-human CEACAM1 monoclonal antibody, 5F4 (200 μg/mouse), or mouse IgG1 (MOPC, 200 μg) was administered intraperitoneally 1-day before, 2-days and 4-days and thereafter every 3 days after inoculation of tumor cells for the indicated times. Mice were sacrificed at 6 weeks after subcutaneous inoculation for evaluation of tumor metastasis and volumes at the inoculation site. Tumor volumes were calculated as $\frac{3}{4}\pi*(L/2)*(H/2)*(W/2)$ where W represents width, H represents height and L represents length.

FIG. 3 depicts an in vivo metastasis model used in experiments described herein. The human pancreatic cancer cell line, AsPc-1, was established as xenografts by injection subcutaneously into the flanks of Rag2$^{-/-}$ mice. Anti-human CEACAM1 monoclonal antibody, 5F4 (200 µg/mouse), or mouse IgG1 (MOPC, 200 µg) was administered intraperitoneally 1-day before, 2-days and 4-days and thereafter every 3 days after inoculation of tumor cells for the indicated times. Mice were sacrificed at 6 weeks after subcutaneous inoculation for evaluation of tumor metastasis and volumes at the inoculation site. Tumor volumes were calculated as $\frac{3}{4}\pi*(L/2)*(H/2)*(W/2)$ where W represents width, H represents height and L represents length.

Figure 4A:
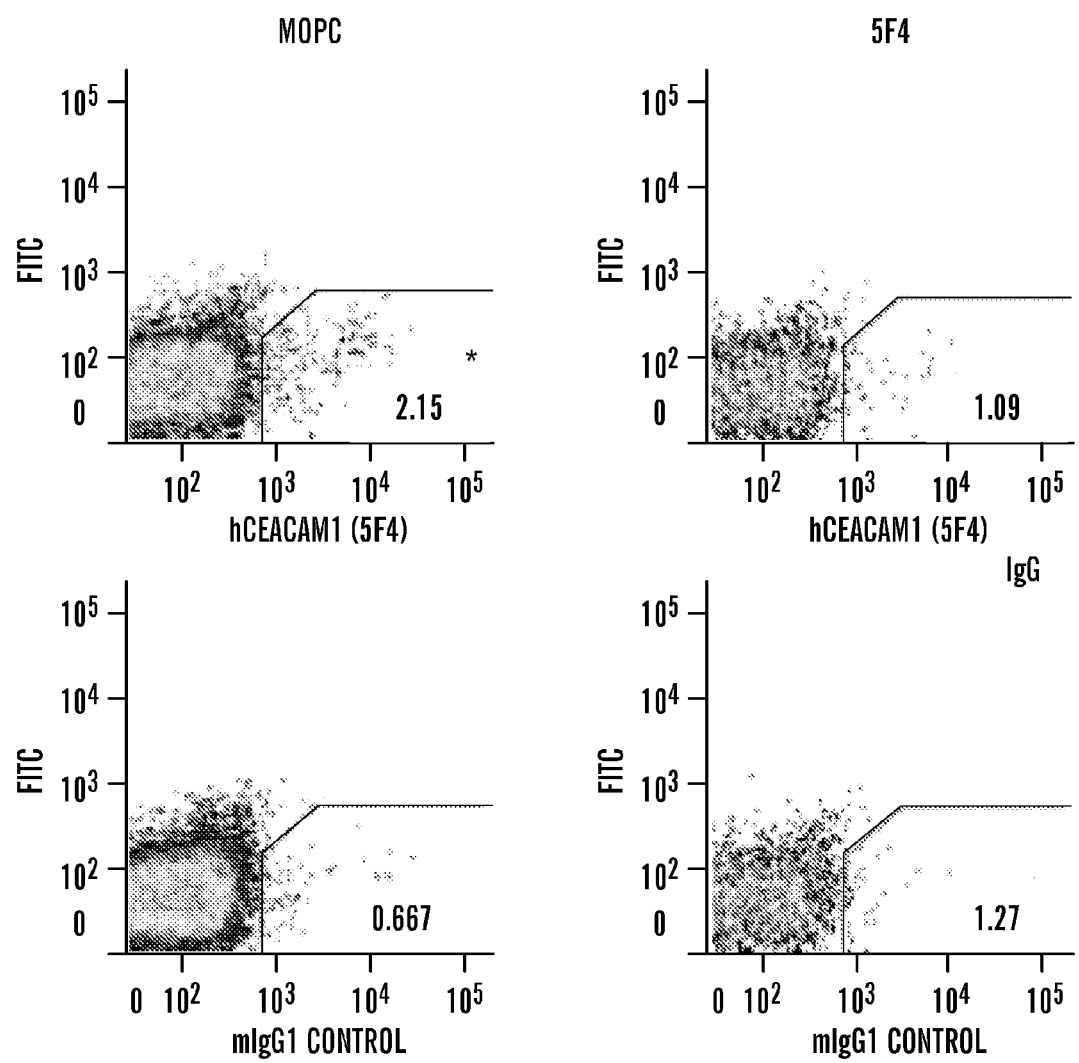

FIGS. 4A-4D demonstrate that the 5F4 antibody described herein prevents AsPc-1 metastasis to the axillary lymph nodes after subcutaneous inoculation as described in FIG. 3. The data here show an analysis two weeks after subcutaneous inoculation. FACS analysis revealed the presence of human CEACAM1$^+$ cells in the axillary LNs of MOPC-treated mice but not in 5F4-treated mice as the 5F4 monoclonal antibody is specific for human CEACAM1 but does not recognize mouse CEACAM1 (n=3 per group) (FIGS. 4A and 4C). PCR analysis revealed detectable levels of human CEACAM1-L in the axillary LNs of MOPC-treated mice but not in 5F4-treated mice (n=2 per group) (FIGS. 4B and 4D). Sp, spleen. LN, axillary lymph node. MLN, mesenteric lymph nodes.

Figure 5A:
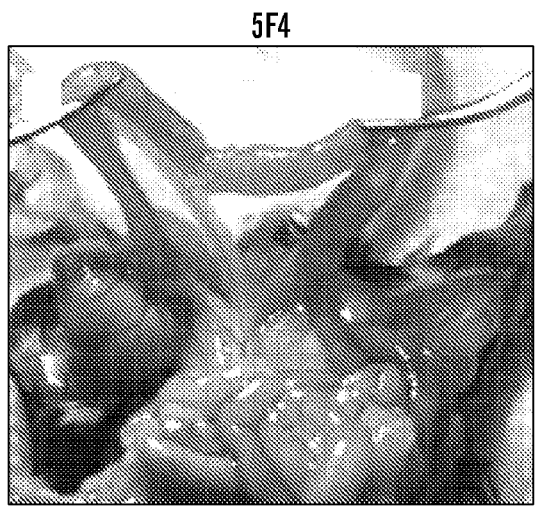
FIGS. 5A-5E show that the 5F4 antibody described herein prevents AsPc-1 metastasis to the abdominal cavity 14 days after subcutaneous inoculation. AsPc-1 derived tumor nodules cells were observed to stud the peritoneum in Rag2$^{-/-}$ mice treated with MOPC (4/7 mice.
Figure 5B:
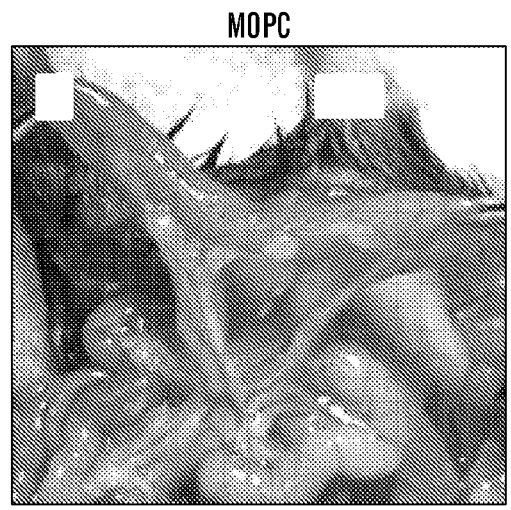
Figure 5C:
Figure 5D:
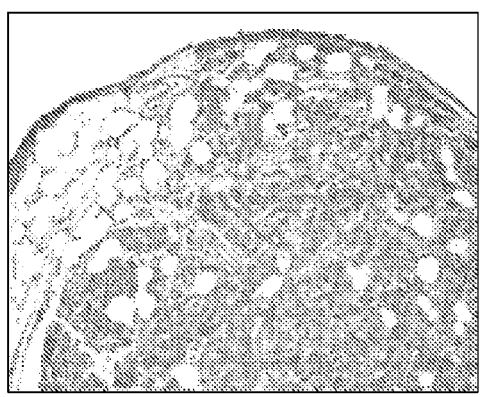
Figure 5E:
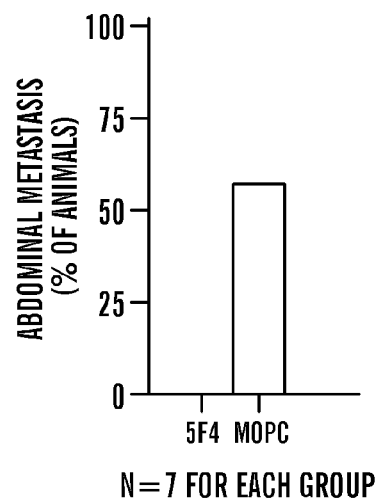

FIGS. 5A-5E show that the 5F4 antibody described herein prevents AsPc-1 metastasis to the abdominal cavity 14 days after subcutaneous inoculation. AsPc-1 derived tumor nodules cells were observed to stud the peritoneum in Rag2$^{-/-}$ mice treated with MOPC (4/7 mice; FIG. 5B) but not in those treated with 5F4 (0/7 mice; FIG. 5A). Hematoxylin and eosin staining of the nodules revealed the presence of AsPc-1 cells in mice treated with MOPC (25×, FIG. 5C and 100×, FIG. 5D). The quantification of these results is shown in FIG. 5E.

Figure 6A:
FIGS. 6A-6O demonstrates that the 5F4 antibody described herein prevents AsPc-1 metastasis in Rag2$^{-/-}$ mice. Rag2$^{-/-}$ mice were administered AsPc-1 cells subcutaneously, as in FIG. 3. Either MOPC (mouse IgG1) or 5F4 were administered intraperitoneally in the schedule described in FIG. 3 and mice assessed at 6 weeks after inoculation. Visible AsPc-1 tumors were localized to the site of injection. The localized tumor at the site of injection was seen after day 9 of tumor inoculation in 5F4-treated mice (FIGS. 6A, 6C, and 6E; arrow). The tumor at the inoculation of the MOPC treated animals was observed later at 28 days post-inoculation and was larger (FIGS. 6B, 6D, and 6F; arrows indicate tumor at inoculation site and peritoneal metastases). Intraperitoneal spread was only seen in mice that received MOPC (FIGS. 6D, 6F, 6L and 6O; arrows indicate metastases associated with organs such as pancreas (FIGS. 6L and 6O) and stomach (FIG. 6O); arrows indicate metastases to peritoneum in FIGS. 6D, 6L and 6O). Blood vessels within the tumor at the inoculation site were observed in MOPC-treated mice (FIG. 6H) but not in 5F4-treated mice (FIG. 6G). Tumor was seen in the prostate (FIG. 6J) and pancreas (FIGS. 6L and 6O) of MOPC-treated mice but not in the prostate (FIG. 6I) or pancreas (FIG. 6K) of 5F4-treated mice. Tumors were observed at the stomach wall (FIG. 6O, upper arrow) adjacent to the pancreatic tumor (FIG. 6O, lower arrow). Tumors cells were detected in the mediastinal LNs (FIG. 6M, arrow) and lungs (FIG. 6M, arrow) of MOPC-treated mice.
Figure 6B:
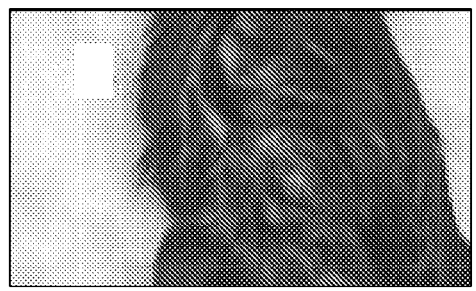
FIG. 6N shows a view of the abdominal cavity 6 weeks after subcutaneous inoculation of AsPc1 cells treated 5 weeks with the 5F4 monoclonal antibody. There are no metastases observed.
Figure 6C:
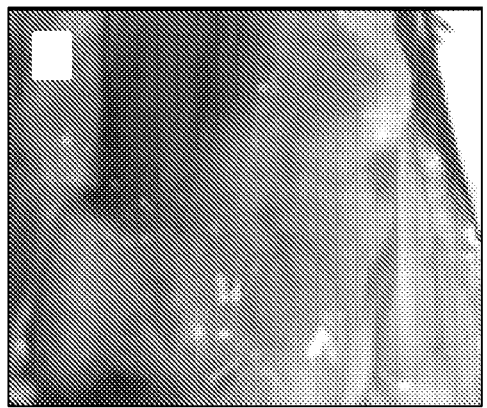
Figure 6D:
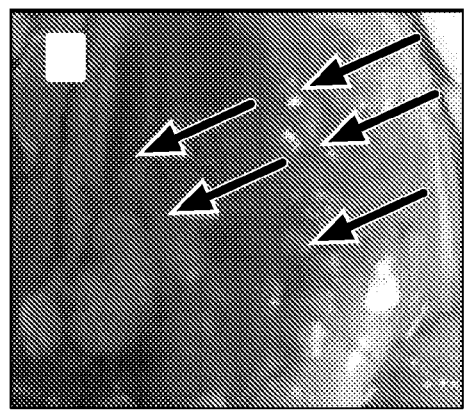
Figure 6E:
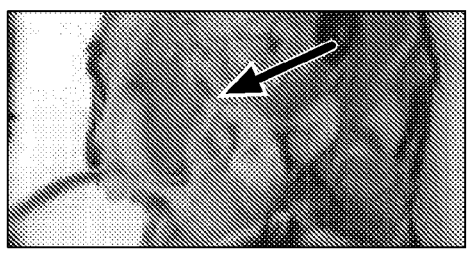
Figure 6F:
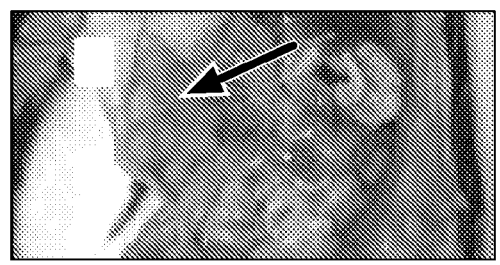
Figure 6G:
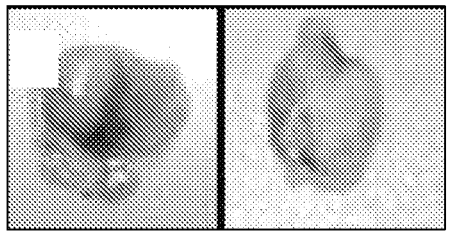
Figure 6H:
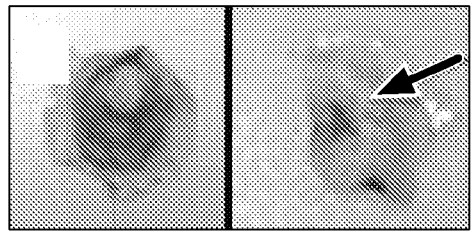
Figure 6I:
Figure 6J:
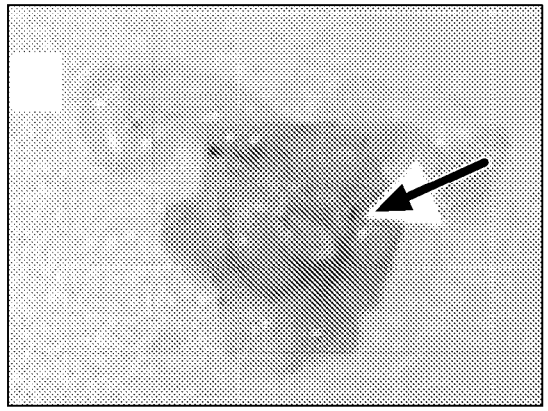
Figure 6K:
Figure 6L:
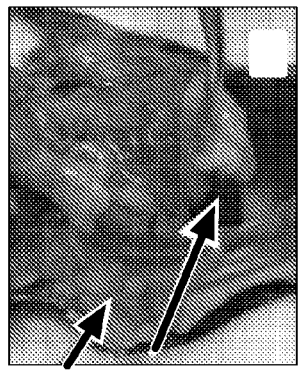
Figure 6M:
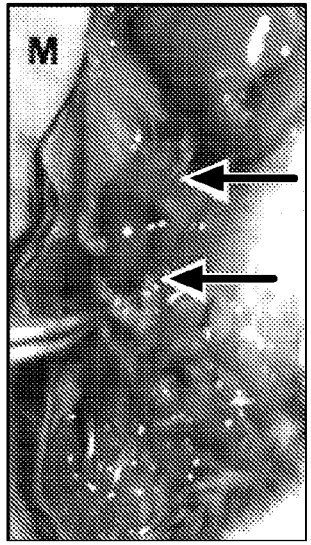
Figure 6N:
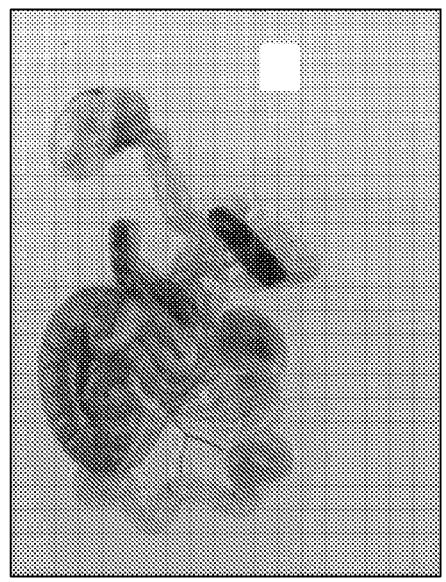
Figure 6O:
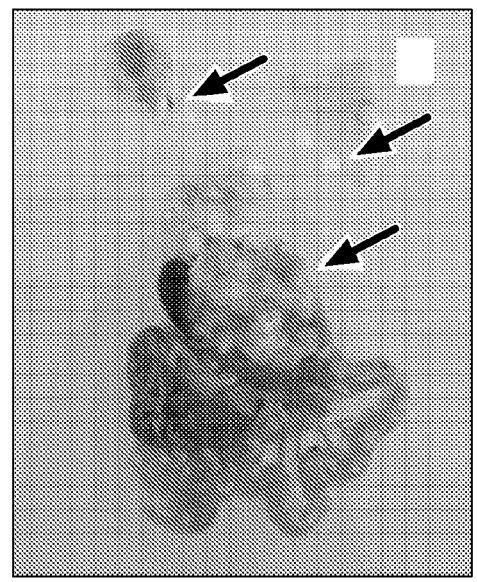

FIGS. 6A-6O demonstrates that the 5F4 antibody described herein prevents AsPc-1 metastasis in Rag2$^{-/-}$ mice. Rag2$^{-/-}$ mice were administered AsPc-1 cells subcutaneously, as in FIG. 3. Either MOPC (mouse IgG1) or 5F4 were administered intraperitoneally in the schedule described in FIG. 3 and mice assessed at 6 weeks after inoculation. Visible AsPc-1 tumors were localized to the site of injection. The localized tumor at the site of injection was seen after day 9 of tumor inoculation in 5F4-treated mice (FIGS. 6A, 6C, and 6E; arrow). The tumor at the inoculation of the MOPC treated animals was observed later at 28 days post-inoculation and was larger (FIGS. 6B, 6D, and 6F; arrows indicate tumor at inoculation site and peritoneal metastases). Intraperitoneal spread was only seen in mice that received MOPC (FIGS. 6D, 6F, 6L and 6O; arrows indicate metastases associated with organs such as pancreas (FIGS. 6L and 6O) and stomach (FIG. 6O); arrows indicate metastases to peritoneum in FIGS. 6D, 6L and 6O). Blood vessels within the tumor at the inoculation site were observed in MOPC-treated mice (FIG. 6H) but not in 5F4-treated mice (FIG. 6G). Tumor was seen in the prostate (FIG. 6J) and pancreas (FIGS. 6L and 6O) of MOPC-treated mice but not in the prostate (FIG. 6I) or pancreas (FIG. 6K) of 5F4-treated mice. Tumors were observed at the stomach wall (FIG. 6O, upper arrow) adjacent to the pancreatic tumor (FIG. 6O, lower arrow). Tumors cells were detected in the mediastinal LNs (FIG. 6M, arrow) and lungs (FIG. 6M, arrow) of MOPC-treated mice. FIG. 6N shows a view of the abdominal cavity 6 weeks after subcutaneous inoculation of AsPc1 cells treated 5 weeks with the 5F4 monoclonal antibody. There are no metastases observed.

Figure 7:
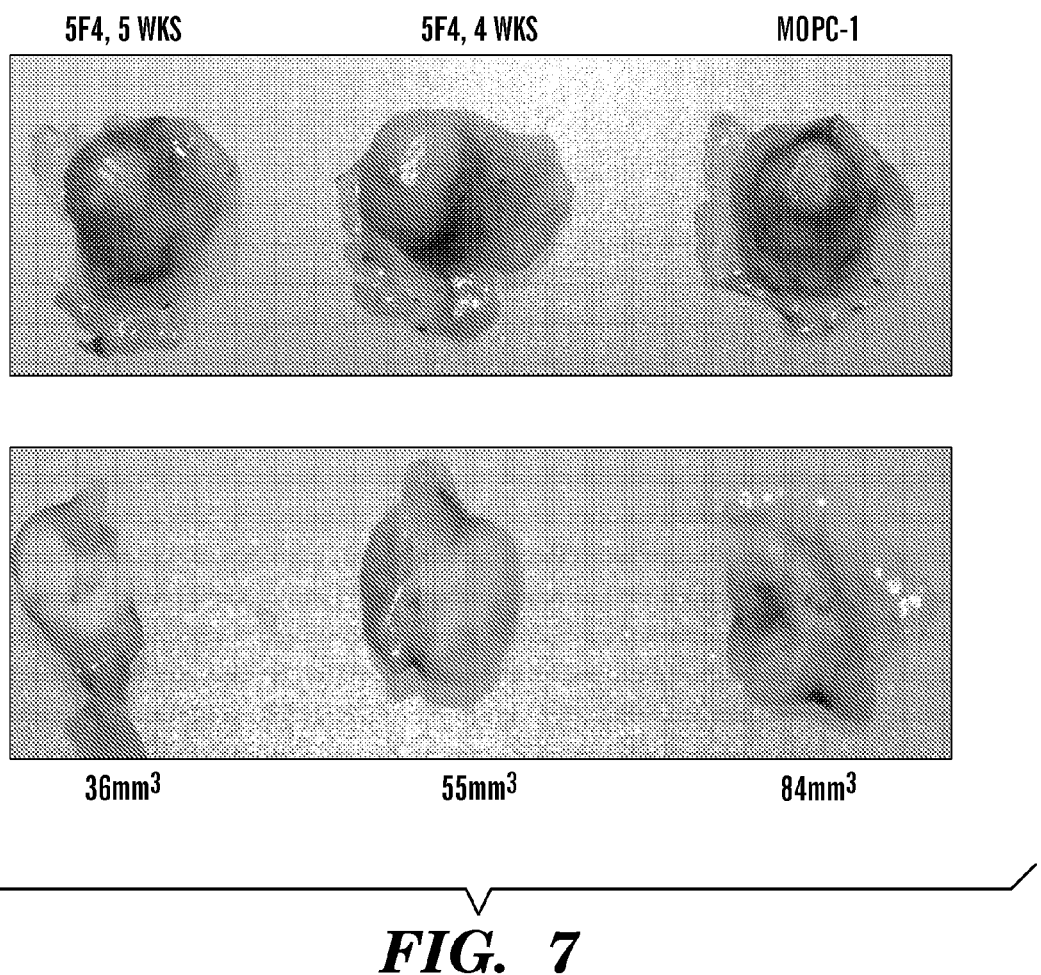
FIG. 7 depicts representative macroscopic subcutaneous tumors after subcutaneous inoculation at 6 weeks after inoculation. Upper panels show subcutaneous tumors excised from the flanks of 5F4 and MOPC-1 treated animals at the indicated treatment schedules. Lower panels show horizontal cross-sections of the same tumors from the indicated experimental animals. The lower panels show increased necrosis of tumors in the 5F4 treated mice. Tumor volumes are shown and were calculated as $\frac{3}{4}\pi*(L/2)*(H/2)*(W/2)$ where W represents width, H represents height and L represents length and shown below the tumors in mm$^3$.

FIG. 7 depicts representative macroscopic subcutaneous tumors after subcutaneous inoculation at 6 weeks after inoculation. Upper panels show subcutaneous tumors excised from the flanks of 5F4 and MOPC-1 treated animals at the indicated treatment schedules. Lower panels show horizontal cross-sections of the same tumors from the indicated experimental animals. The lower panels show increased necrosis of tumors in the 5F4 treated mice. Tumor volumes are shown and were calculated as $\frac{3}{4}\pi*(L/2)*(H/2)*(W/2)$ where W represents width, H represents height and L represents length and shown below the tumors in mm$^3$.

Figure 8:
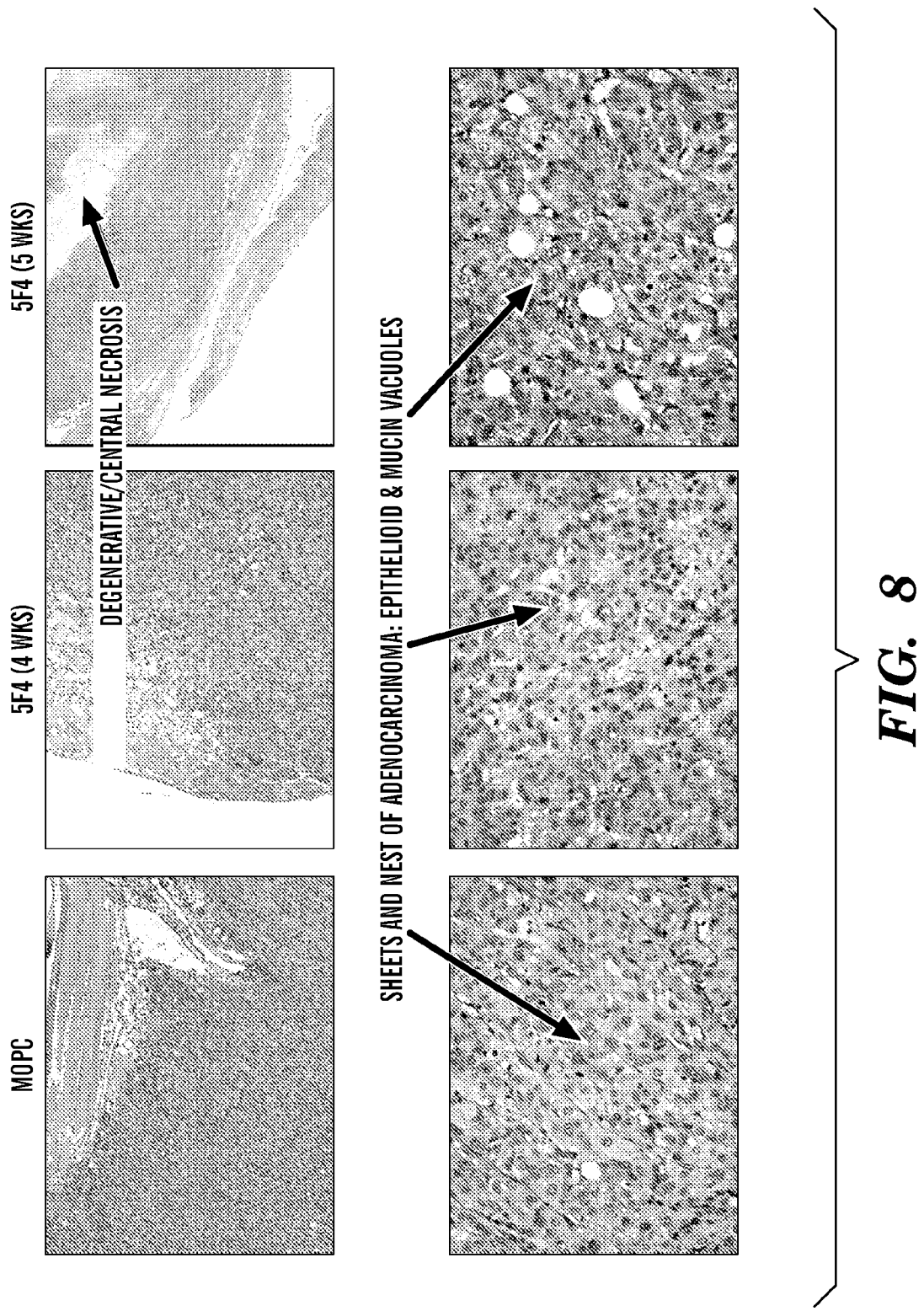
FIG. 8 shows pathology of subcutaneous tumors in animals inoculated subcutaneously with AsPc-1 after 6 weeks. Subcutaneous tumors are composed of sheets and nests of poorly differentiated carcinoma with epithelioid features and some intracellular mucin vacuoles consistent with adenocarcinoma. They show some degenerative changes and central necrosis which is increased after prolonged treatment with 5F4, human CEACAM1 specific monoclonal antibody.

FIG. 8 shows pathology of subcutaneous tumors in animals inoculated subcutaneously with AsPc-1 after 6 weeks. Subcutaneous tumors are composed of sheets and nests of poorly differentiated carcinoma with epithelioid features and some intracellular mucin vacuoles consistent with adenocarcinoma. They show some degenerative changes and central necrosis which is increased after prolonged treatment with 5F4, human CEACAM1 specific monoclonal antibody.

Figure 9:
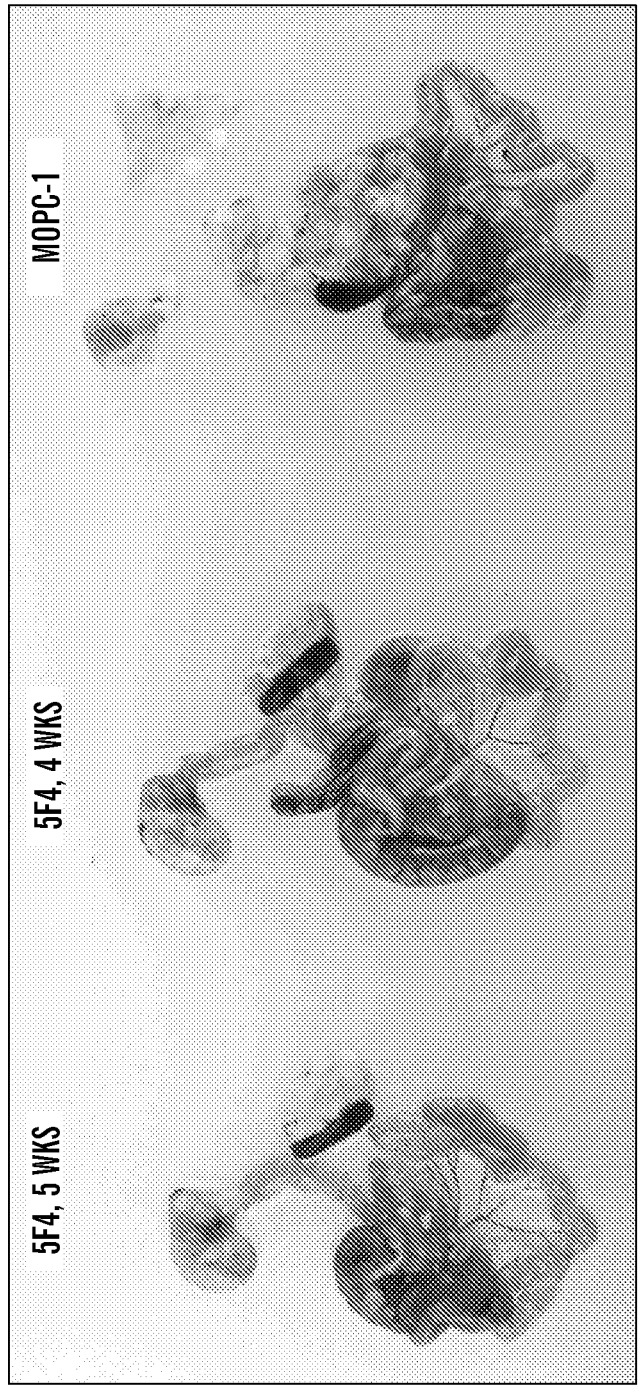
FIG. 9 demonstrates that anti-human CEACAM1 monoclonal antibody 5F4 protects Rag2-deficient mice from human pancreatic cell line (AsPc-1) macrometastasis 6 weeks after subcutaneous AsPc-1 cell inoculation into Rag2$^{-/-}$ mice. Representative macroscopic metastatic tumors after subcutaneous inoculation are only observed in MOPC-treated animals. Four and five weeks of 5F4 monoclonal antibody treatment were able to prevent metastasis as shown. Tumors were seen in the stomach wall adjacent to metastatic pancreatic tumor and the peritoneal cavity with invasion into the mucosal tissues in the MOPC treated animals (as also described in FIG. 6).

FIG. 9 demonstrates that anti-human CEACAM1 monoclonal antibody 5F4 protects Rag2-deficient mice from human pancreatic cell line (AsPc-1) macrometastasis 6 weeks after subcutaneous AsPc-1 cell inoculation into Rag2$^{-/-}$ mice. Representative macroscopic metastatic tumors after subcutaneous inoculation are only observed in MOPC-treated animals. Four and five weeks of 5F4 monoclonal antibody treatment were able to prevent metastasis as shown. Tumors were seen in the stomach wall adjacent to metastatic pancreatic tumor and the peritoneal cavity with invasion into the mucosal tissues in the MOPC treated animals (as also described in FIG. 6).

Figure 10:
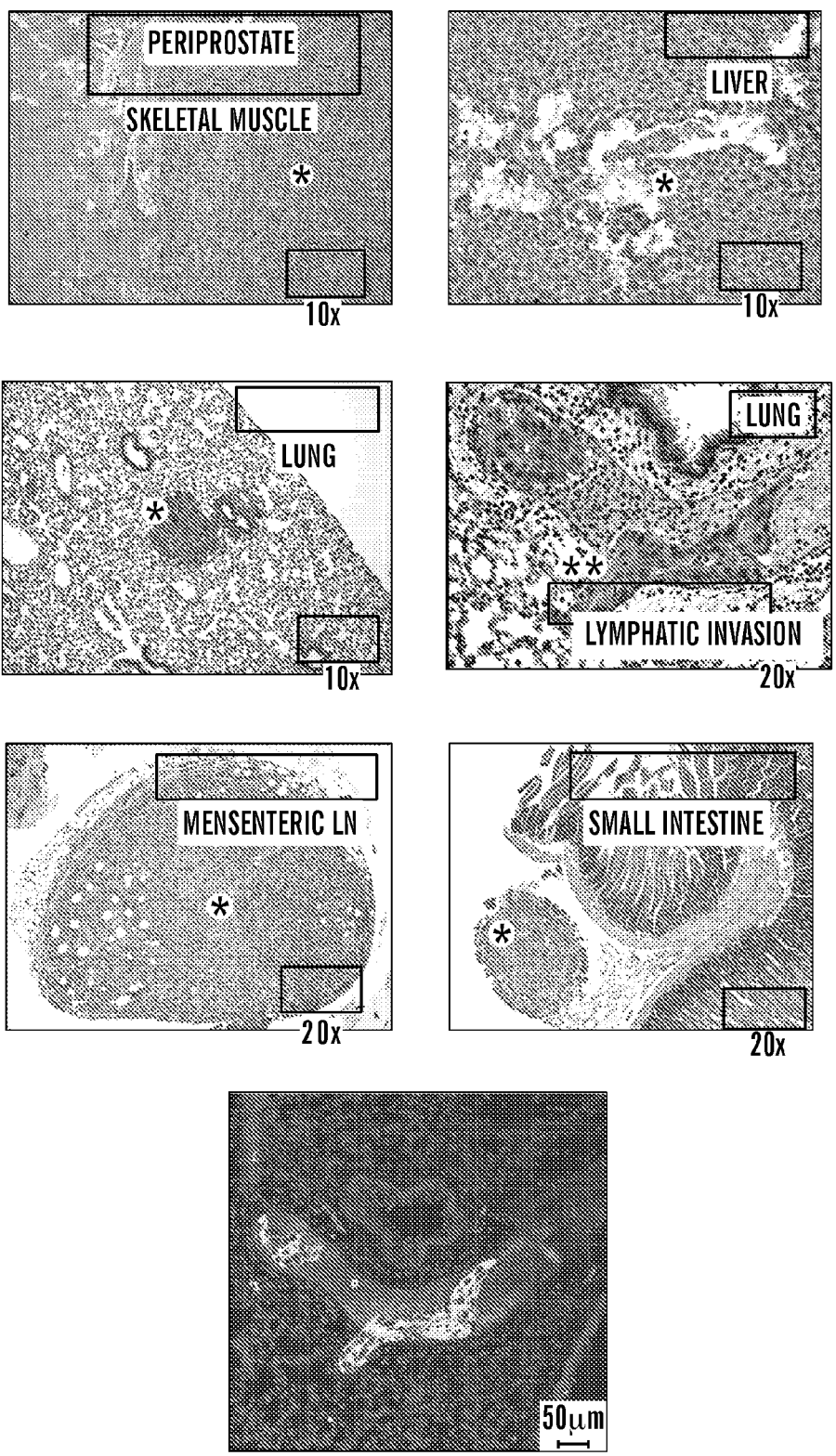
FIG. 10 shows pathology of long-distance spreading pancreatic tumor cell metastasis after subcutaneous inoculation in mice treated with MOPC antibody at 6 weeks after inoculation. Pathology of individual tissues is shown after Hematoxylin and Eosin staining. Stars (*) indicate the extensive tumor growth observed in immune-deficient Rag2$^{-/-}$ mice only in the MOPC control, but not 5F4 treated mice. Human pancreatic cancer cells were observed to grow in Rag2$^{-/-}$ mice and metastasize to the prostate, liver, lung (10× magnifications), mesenteric lymph node and small intestine (20× magnifications). In addition, lymphatic invasion of pancreatic tumor cells in the lung was seen in this model as shown by the double asterices (20× magnifications). The latter is shown by immunofluorescence staining (cytokeratin, indicative of the tumor; LYVE-1, indicative of lymph vessels.

FIG. 10 shows pathology of long-distance spreading pancreatic tumor cell metastasis after subcutaneous inoculation in mice treated with MOPC antibody at 6 weeks after inoculation. Pathology of individual tissues is shown after Hematoxylin and Eosin staining. Stars (*) indicate the extensive tumor growth observed in immune-deficient Rag2$^{-/-}$ mice only in the MOPC control, but not 5F4 treated mice. Human pancreatic cancer cells were observed to grow in Rag2$^{-/-}$ mice and metastasize to the prostate, liver, lung (10× magnifications), mesenteric lymph node and small intestine (20× magnifications). In addition, lymphatic invasion of pancreatic tumor cells in the lung was seen in this model as shown by the double asterisks (20× magnifications). The latter is shown by immunofluorescence staining (cytokeratin, indicative of the tumor; LYVE-1, indicative of lymph vessels.

Figure 11:
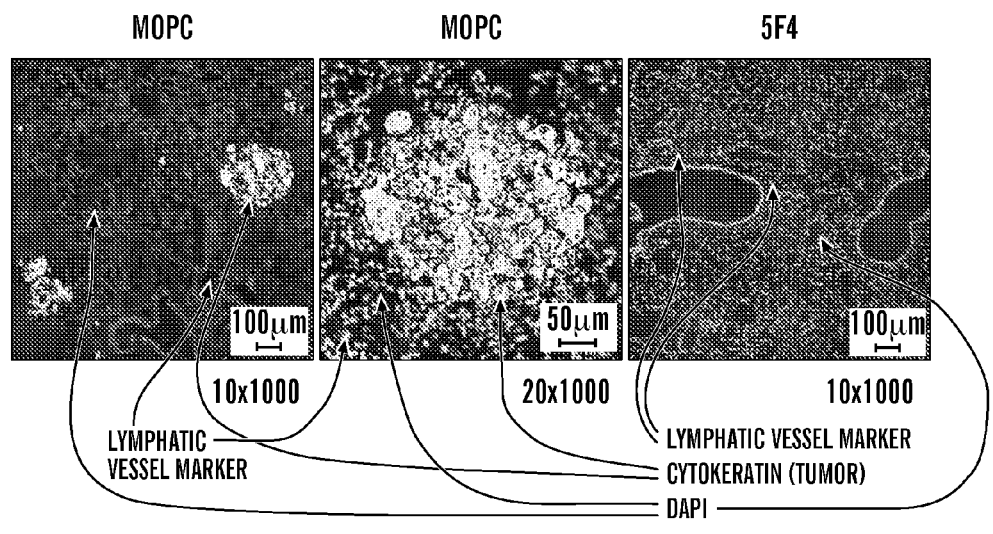
FIG. 11 shows identification of metastastatic tumors after subcutaneous inoculation at 6 weeks. Lungs of MOPC- and 5F4-treated animals are shown. Tumor was only identified in the animals treated with MOPC, but not 5F4, administration as revealed by staining with a tumor marker (cytokeratin). DAPI stains nuclei.

FIG. 11 shows identification of metastastatic tumors after subcutaneous inoculation at 6 weeks. Lungs of MOPC- and 5F4-treated animals are shown. Tumor was only identified in the animals treated with MOPC, but not 5F4, administration as revealed by staining with a tumor marker (cytokeratin). DAPI stains nuclei.

Figure 12A:
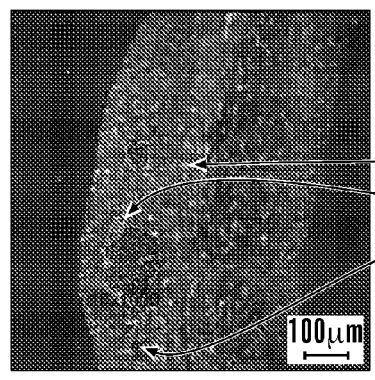
FIGS. 12A-12B show immunoflourescence identification of lymphatic metastasis after subcutaneous inoculation.
Figure 12B:
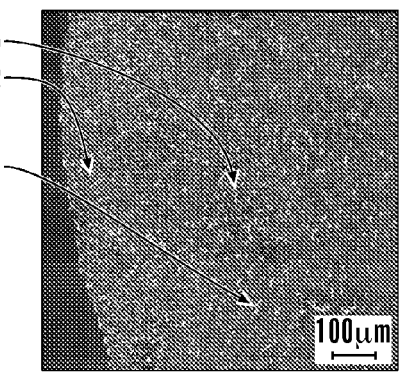

FIGS. 12A-12B show immunofluorescence identification of lymphatic metastasis after subcutaneous inoculation. FIG. 12A shows specific staining for lymphatic vessels (Lymphatic vessel endothelial maker, Lyve-1) and invasive tumor cells (cytokeratin) identified after MOPC but not 5F4 treatment. Tumor cells were surrounded by newly generated lymphatic vessels (staining consistent with overlap between these two markers). FIG. 12B demonstrates that no specific staining for lymphatic vessels (Lymphatic vessel endothelial maker, Lyve-1) nor tumor cells (cytokeratin) was identified after 5F4 treatment.

Figure 13A:
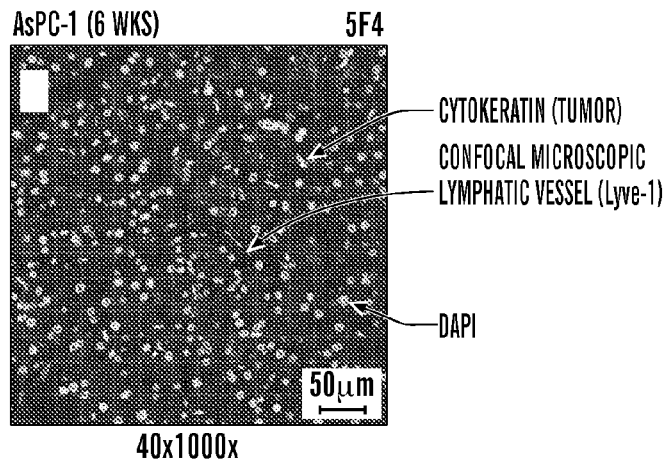
FIGS. 13A-13E show immunoflourscence identification of lymphatic metastasis after subcutaneous inoculation.
Figure 13B:
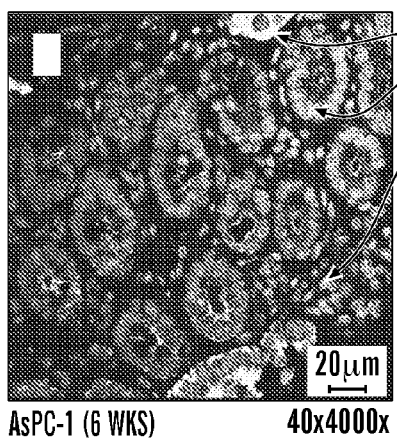
Figure 13C:
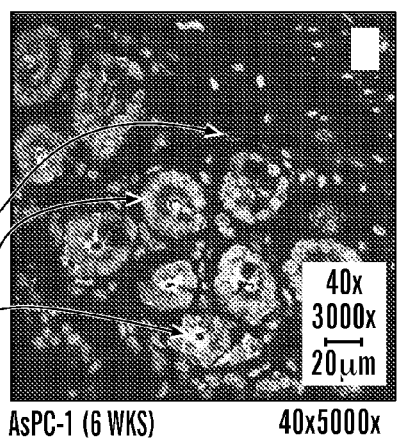
Figure 13D:
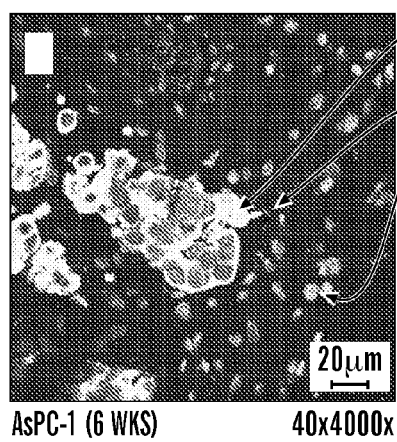
Figure 13E:
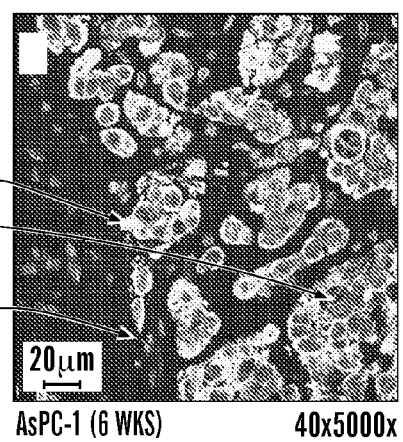

FIGS. 13A-13E show immunofluorescence identification of lymphatic metastasis after subcutaneous inoculation. FIG. 13A shows the pancreas of 5F4-treated animals. No specific staining for lymphatic vessels (Lymphatic vessel endothelial maker, Lyve-1) nor tumor cells (cytokeratin) was identifiable. FIG. 13B-13E show pancreas of MOPC-treated animals. Specific staining for lymphatic vessels (Lymphatic vessel endothelial maker, Lyve-1) and invasive tumor cells (cytokeratin) was identified. In FIGS. 13D and 13E, tumor cells were surrounded by newly generated lymphatic vessels.

Figure 20:
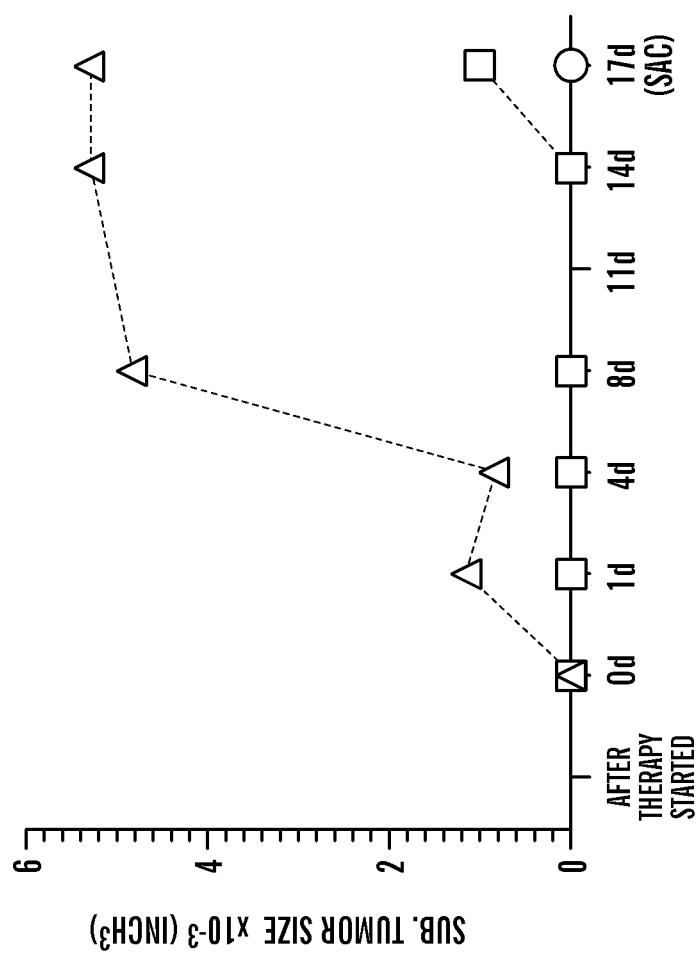
FIG. 20 depicts a therapeutic model for pancreatic cancer treatment with 5F4 monoclonal antibody. $2 \times 10^6$ AsPc1 cells were inoculated subcutaneously into Ceacam1$^{-/-}$Rag2$^{-/-}$ mice. At 12 days after tumor inoculation and evidence of a palpable tumor, therapy with 5F4 monoclonal antibody was initiated at 200 micrograms per injection every 2-3 days for a total of 6 injections over a 2 week time period. During this time, the size of the local subcutaneous tumor nodule was measured as shown. MOPC (mouse IgG1) served as a control. MOPC treated animals, as shown by mouse number 73 (triangles), exhibited increased tumor growth relative to 5F4 monoclonal antibody treated mice as shown by mouse numbers 71 and 72 (square and circle). These studies demonstrate 5F4-mediated inhibition of primary tumor growth.

FIG. 20 depicts a therapeutic model for pancreatic cancer treatment with 5F4 monoclonal antibody. 2×10$^6$ AsPc1 cells were inoculated subcutaneously into Ceacam1$^{-/-}$Rag2$^{-/-}$ mice. At 12 days after tumor inoculation and evidence of a palpable tumor, therapy with 5F4 monoclonal antibody was initiated at 200 micrograms per injection every 2-3 days for a total of 6 injections over a 2 week time period. During this time, the size of the local subcutaneous tumor nodule was measured as shown. MOPC (mouse IgG1) served as a control. MOPC treated animals, as shown by mouse number 73 (triangles), exhibited increased tumor growth relative to 5F4 monoclonal antibody treated mice as shown by mouse numbers 71 and 72 (square and circle). These studies demonstrate 5F4-mediated inhibition of primary tumor growth.

Figure 21:
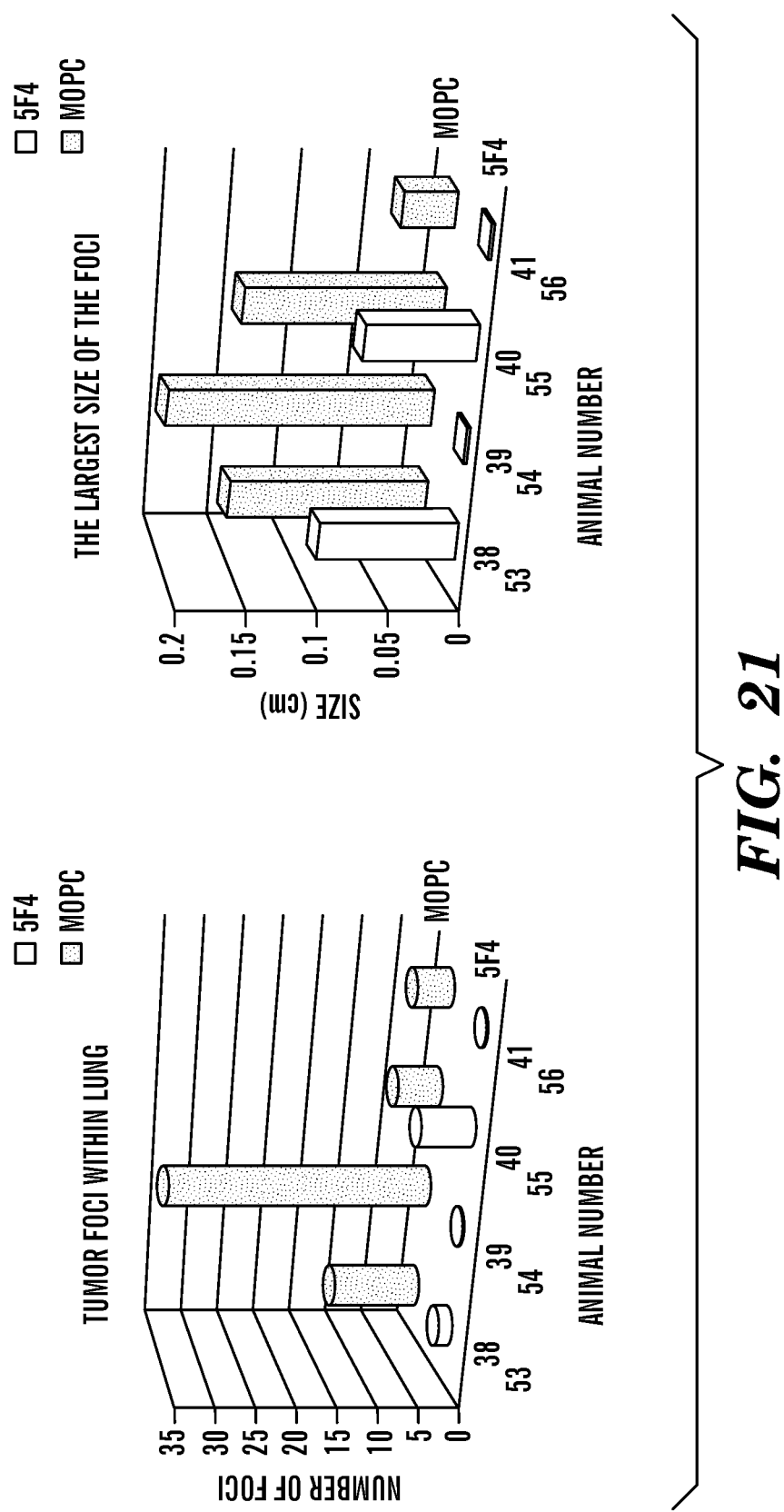
FIG. 21 demonstrates that therapeutic treatment with 5F4 monoclonal antibody blocks metastatic disease to the lungs. Using the protocol described in FIG. 20, 5F4 and MOPC treated mice were sacrificed at day 26. Lung tissues were harvested and tissues stained with haematoxylin and eosin after paraffin fixation. Microscopic examination of histologic sections were examined for the number of tumor foci demonstrable in the lungs as well as the size of the largest nodule identified in the 5F4 treated group (n=4) and MOPC treated group (n=4). As can be observed, 5F4 treatment resulted in decreased numbers and size of metastatic nodules to the lungs in Ceacam1$^{-/-}$ X Rag2$^{-/-}$ mice.

FIG. 21 demonstrates that therapeutic treatment with 5F4 monoclonal antibody blocks metastatic disease to the lungs. Using the protocol described in FIG. 20, 5F4 and MOPC treated mice were sacrificed at day 26. Lung tissues were harvested and tissues stained with haematoxylin and eosin after paraffin fixation. Microscopic examination of histologic sections were examined for the number of tumor foci demonstrable in the lungs as well as the size of the largest nodule identified in the 5F4 treated group (n=4) and MOPC treated group (n=4). As can be observed, 5F4 treatment resulted in decreased numbers and size of metastatic nodules to the lungs in Ceacam1$^{-/-}$ X Rag2$^{-/-}$ mice.

Example 2

Cloning and Sequencing of Monoclonal Anti-CEACAM1 Antibodies

The objective of this example was to obtain V-region (V$_H$ and V$_L$) sequences encoding the monoclonal antibodies expressed by each of three hybridomas (5F4/2C6/2H3, 34B1/2E8/2E6 and 26H7/2H9/2E10). Viable frozen hybridoma cells were revived and RNA was extracted. The mRNA was reverse transcribed and antibody-specific transcripts were PCR amplified. The PCR products were cloned, nucleotide and amino acid sequences of the antibody $V_H$ and $V_L$ regions were determined, and the sequence data were analyzed.

The isotypes of each antibody were determined from cell culture supernatants using a Pierce Rapid ELISA Mouse mAb Isotyping Kit (Thermo Scientific cat. no. 37503). All three antibodies were found to be mouse IgG1/κ RNA was extracted from cell pellets using an RNAQUEOUS®-4PCR kit (Ambion cat. no. AM1914). V-regions were amplified by RT-PCR using degenerate primer pools for murine antibody signal sequences together with constant region primers for $IgGV_H$ and $IgKV_L$. Heavy chain V-region mRNA was amplified using a set of six degenerate primer pools (HA to HF) and light chain V-region mRNA was amplified using a set of seven degenerate primer pools (KA to KG). The PCR products obtained from each of the successful amplifications were purified and cloned into a 'TA' cloning vector (pGEM-T® Easy, Promega, cat. #A1360), from which sequences were obtained.

For hybridoma 5F4/2C6/2H3, the heavy chain V-region, amplification products of the expected size were observed with primer pools HA, HC and HF. For the light chain V-region, RT-PCR amplification products were obtained from primer pools KB, KC, and KG. Eighteen $V_H$ and fourteen Vκ clones were sequenced. A single functional $V_H$ gene was identified in ten clones from primer pools HA and HF. Clones sequenced from primer pool HC were found to contain a non-functional transcript. A single functional Vκ gene sequence was identified in all six clones from primer pool KG. The remaining eight Vκ clones sequenced from primer pools KB and KC contained an aberrant transcript (GenBank accession number M35669) normally associated with the hybridoma fusion partner SP2/0.

For hybridoma 34B1/2E8/2E6, the heavy chain V-region, amplification products of the expected size were observed with primer pools HA, HC and HF. For the light chain V-region, RT-PCR amplification products were obtained from primer pools KB, KC, and KG. Eighteen $V_H$ and fourteen Vκ clones were sequenced. A single functional VH gene was identified in eleven clones sequenced from primer pools HA and HF. Clones sequenced from primer pool HC were found to contain a nonfunctional transcript. A single functional Vκ gene sequence was identified in all six clones from primer pool KG. The remaining 8 Vκ clones sequenced from primer pools KB and KC contained an aberrant transcript (GenBank accession number M35669) normally associated with the hybridoma fusion partner SP2/0.

For hybridoma 26H7/2H9/2E10, the heavy chain V-region, amplification products of the expected size were observed with primer pools HA, HB, HC and HF. For the light chain V region, RT-PCR amplification products were obtained from primer pools KB, KC, KD, KF and KG. Twenty-eight VH and twenty-nine Vκ clones were sequenced. A single functional VH gene was identified in ten clones sequenced from primer pools HA and HF. Clones sequenced from primer pools HB and HC were found to contain a non-functional transcript. Two functional Vκ gene sequences were identified, one which was identified in eight clones from primer pools KD and KG (referred to as 'seq1') and a second which was identified in two clones from primer pools KD and KF (referred to as 'seq2'). The eight Vκ clones sequenced from primer pools KB and KC contained an aberrant transcript (GenBank accession number M35669) normally associated with the hybridoma fusion partner SP2/0.

An analysis of the sequences obtained from hybridomas 5F4/2C6/2H3, 34B1/2E8/2E6 and 26H7/2H9/2E10 showed that the V-region sequences had high homologies to mouse V-region subgroups. Furthermore, CDR lengths were in the normal range for mouse V-regions. Therefore, 5F4/2C6/2H3, 34B1/2E8/2E6 and 26H7/2H9/2E10 monoclonal antibodies are not considered to have any unusual features requiring any unusual measures for humanisation. In addition, it was noted that the mouse $V_H$ chains showed good homology with the closest human germline V-region sequences (78%, 79%, 75% identity for 5F4/2C6/2H3, 34B1/2E8/2E6 and 26H7/2H9/2E10 respectively) as well as the Vκ chains for 26H7/2H9/2E10 antibody (77% and 73% for seq1 and seq2, respectively) while the remaining two Vκ chains showed lower overall homology to human germline V-regions (62% and 60% identity for 5F4/2C6/2H3 and 34B1/2E8/2E6, respectively). This indicates that, particularly for the Vκ chains with low human germline homology, standard germline humanisation requires input of mutations in the germline frameworks with the likelihood of creating CD4+ T cell epitopes. These considerations further support the application of COMPOSITE HUMAN ANTIBODY™ technology (using segments of human V-regions), as described herein, which is not influenced by V-region homologies between mouse and human germline V-regions and creates fully humanized sequences devoid of T cell epitopes.

V-regions from hybridomas 5F4/2C6/2H3, 34B1/2E8/2E6 and 26H7/2H9/2E10 were cloned and sequenced resulting in the identification of unique sequences for VH and Vk in 5F4/2C6/2H3 and 34B1/2E8/2E6 antibodies. One single VH and 2 Vk sequences were found in the 26H7/2H9/2E10 antibody; however the frequency of the transcripts suggests that seq1 is likely to be antigen-specific although two alternative antibodies comprising each Vk sequence can be made (typically as chimeric antibodies) for binding analysis to confirm that seq1 is the authentic Vk sequence for the 26H7/2H9/2E10 antibody. Analysis of the sequences indicated no unusual features requiring any unusual measures for humanization.

The amino acid sequence of the hybridoma 5F4/2C6/2H3 VH is:

```
                                        (SEQ ID NO: 26)
EVQLVESGGDLVKPGGSLKLACA

ASGFIFSSHGMSWVRQTPDKRLE

WVATISSGGTYTYYPDSVKGRFT

ISRDNDKNTLYLQMNSLKSEDTA

MYYCARHDFDYDAAWFAYWGQGT

LVTVSA
```

The amino acid sequence of the hybridoma 5F4/2C6/2H3 VL is:

```
                                        (SEQ ID NO: 27)
QIVLTQSPALMSASPGVKVTMTC

SANSSVSYMYWYRQKPRSSPKPW
```

-continued
IYLTSNLASGVPARFSGSGSGTS
YSLTISSMEAEDAATYYCQQWSS
NPPTFGSGTKLEIK

The amino acid sequence of the hybridoma 34B1/2E8/2E6 HV is:

(SEQ ID NO: 28)
EVQLVESGGDLVKPGGSLKLSCAA
SGFTFSFYGMSWVRQTPDKRLEWV
ATFSGGGNYTYYPDSVKGRFTISR
DNAKNTLYLQMSSLKSEDTARYYC
ARHGGLPFYAMDYWGQGTSVTVSS

The amino acid sequence of the hybridoma 34B1/2E8/2E6 VL is:

(SEQ ID NO: 29)
EIVITQSPALMAASPGEKVTITCS
VSSSISSSNLHWYQQKSETSPKPW
IYGTFNLASGVPVRFSGSGSTSY
SLTISSMEAEDAATYYCQQWSSHP
FTFGSGTKLEIK

The amino acid sequence of the hybridoma 26H7/2H9/2E10 VH is:

(SEQ ID NO: 30)
EVQLVESGGGFVKPGGSLKLSCAA
SGFSFSDYYLYWVRQTPEKRLEWV
ATISVGGGNTSYPDSVKGRFTISR
DNAKNNLYLQMSSLKSEDTAMYYC
TRGLYYGPAWFAYWGQGTLVTVSA

The amino acid sequence of the hybridoma 26H7/2H9/2E10 VL(seq1) is:

(SEQ ID NO: 31)
DIVMTQSPSSLAMSVGQKVTMSCK
SSQSLLNSSNQKNYLAWFQQTPGQ
SPKLLVYFASTRESGVPDRFIGSG
SGTDFTLTISSVKAEDLADYFCQQ
HYSTPWTFGGGTKLEIR

The amino acid sequence of the hybridoma 26H7/2H9/2E10 VL(seq2) is:

(SEQ ID NO: 32)
DIQMTQSPSSLSASLGERVSLTCR
ASQKISGYLSWLQQKPDGTIKRLI
YAASTLDSGVPKRFSGSRSGSDYS

-continued
LTISSLESEDFADYYCLQYASSLM
YTFGGGTKLEIK

The oligonucleotide sequence encoding the hybridoma 5F4/2C6/2H3 VH is:

(SEQ ID NO: 33)
GAGGTGCAGTTGGTGGAGTCTGG
GGGAGACTTGGTGAAGCCTGGAG
GGTCCCTGAAACTCGCCTGTGCA
GCCTCTGGATTCATTTTCAGTAG
CCATGGCATGTCTTGGGTTCGCC
AGACTCCAGACAAGAGGCTGGAG
TGGGTCGCAACCATTAGCAGTGG
TGGTACTTACACCTACTATCCAG
ACAGTGTGAAGGGGCGATTCACC
ATATCCAGAGACAATGACAAAAA
CACCCTGTACCTGCAAATGAACA
GTCTGAAGTCTGAGGACACAGCC
ATGTATTACTGTGCAAGACACGA
CTTTGATTACGACGCGGCCTGGT
TTGCTTACTGGGGCCAAGGGACT
CTGGTCACTGTCTCTGCA

The oligonucleotide sequence encoding the hybridoma 5F4/2C6/2H3 VL is:

(SEQ ID NO: 34)
CAAATTGTTCTCACCCAGTCTCC
AGCACTCATGTCTGCATCTCCAG
GGGTGAAAGTCACCATGACCTGC
AGTGCCAACTCAAGTGTAAGTTA
CATGTATTGGTATCGGCAGAAGC
CAAGATCCTCCCCCAAACCCTGG
ATTTATCTCACATCCAACCTGGC
TTCTGGAGTCCCTGCTCGCTTCA
GTGGCAGTGGGTCTGGGACCTCT
TATTCTCTCACAATCAGCAGCAT
GGAGGCTGAAGATGCTGCCACTT
ATTACTGCCAGCAGTGGAGTAGT
AACCCACCCACGTTCGGCTCGGG
GACAAAGTTGGAAATAAAA

The oligonucleotide sequence encoding the hybridoma 34B1/2E8/2E6 HV is:

(SEQ ID NO: 35)
GAGGTGCAGCTGGTGGAGTCTGG
GGGAGACTTAGTGAAGCCTGGAG
GGTCCCTGAAACTCTCCTGTGCA
GCCTCTGGATTCACTTTCAGTTT
CTATGGCATGTCTTGGGTTCGCC
AGACTCCAGACAAGAGGCTGGAG
TGGGTCGCAACCTTTAGTGGTGG
TGGTAATTACACCTACTATCCAG
ACAGTGTGAAGGGGCGATTCACC
ATCTCCAGAGACAATGCCAAGAA
CACCCTTTACCTCCAAATGAGCA
GTCTGAAGTCTGAGGACACAGCC
AGGTATTACTGTGCAAGACATGG
GGGGTTACCATTTTATGCTATGG
ACTACTGGGGTCAAGGAACCTCA
GTCACCGTCTCCTCA

The oligonucleotide sequence encoding the hybridoma 34B1/2E8/2E6 LV is:

(SEQ ID NO: 36)
GAAATTGTGATCACCCAGTCTCCA
GCACTCATGGCTGCATCTCCAGGG
GAGAAGGTCACCATCACCTGCAGT
GTCTCCTCAAGTATAAGTTCCAGC
AACTTGCACTGGTACCAGCAGAAG
TCAGAAACCTCCCCCAAACCCTGG
ATTTATGGCACATTTAACCTGGCT
TCTGGAGTCCCTGTTCGCTTCAGT
GGCAGTGGATCTGGGACCTCTTAT
TCTCTCACAATCAGCAGCATGGAG
GCTGAAGATGCTGCCACTTATTAC
TGTCAACAGTGGAGTAGTCACCCA
TTCACGTTCGGCTCGGGGACAAAG
TTGGAAATAAAA

The oligonucleotide sequence encoding the hybridoma 26H7/2H9/2E10 VH is:

(SEQ ID NO: 37)
GAAGTGCAGCTGGTGGAGTCTGG
GGGGGCTTTGTGAAGCCTGGAG
GGTCCCTGAAACTCTCCTGTGCA

-continued
GCCTCTGGATTCTCTTTCAGTGA
CTATTACTTGTATTGGGTTCGCC
AGACTCCGGAAAAAGGCTGGAG
TGGGTCGCAACCATTAGTGTTGG
TGGTGGTAACACCTCCTATCCGG
ACAGTGTGAAGGGGCGATTCACC
ATCTCCAGAGACAATGCCAAGAA
CAACCTGTACCTGCAAATGAGCA
GTCTGAAGTCTGAGGACACAGCC
ATGTATTACTGTACAAGGGGCCT
TTACTACGGCCCGGCCTGGTTTG
CTTACTGGGGCCAAGGGACTCTG
GTCACTGTCTCTGCA The oligonucleotide sequence encoding the hybridoma 26H7/2H9/2E10(seq1) VL is:

(SEQ ID NO: 38)
GACATTGTGATGACACAGTCTCC
ATCCTCCCTGGCTATGTCAGTAG
GACAGAAGGTCACTATGAGCTGC
AAGTCCAGTCAGAGCCTTTTAAA
TAGTAGCAATCAAAAGAACTATT
TGGCCTGGTTCCAGCAGACACCA
GGACAGTCTCCTAAACTTCTGGT
ATACTTTGCATCCACTAGGGAAT
CTGGGGTCCCTGATCGCTTCATA
GGCAGTGGTTCTGGGACAGATTT
CACTCTTACCATCAGCAGTGTGA
AGGCTGAGGACCTGGCAGATTAC
TTCTGTCAGCAACATTATAGCAC
TCCGTGGACGTTCGGTGGAGGCA
CCAAGCTGGAAATCAGA

The oligonucleotide sequence encoding the hybridoma 26H7/2H9/2E10(seq2) VL is:

(SEQ ID NO: 39)
GACATCCAGATGACCCAGTCTC
CATCCTCCTTATCTGCCTCTCT
GGGAGAAAGAGTCAGTCTCACT
TGTCGGGCAAGTCAGAAAATTA
GTGGTTACTTAAGCTGGCTTCA
GCAGAAACCTGATGGAACTATT

```
AAGCGCCTCATCTACGCCGCAT

CCACTTTAGATTCTGGTGTCCC

AAAAAGGTTCAGTGGCAGTAGG

TCTGGGTCAGATTATTCTCTCA

CCATCAGCAGCCTTGAGTCTGA

AGATTTTGCAGACTATTACTGT

CTACAATATGCTAGTTCTCTCA

TGTACACGTTCGGAGGGGGAC

CAAACTGGAAATAAAG
```

We claim:

1. An isolated CEACAM1-specific recombinant monoclonal antibody or an antigen-binding portion thereof, comprising: at least one light chain component and at least one heavy chain component, wherein said heavy chain component comprises the amino acids of SEQ ID NO:26, SEQ ID NO:28, or SEQ ID NO:30; and said light chain component comprises the amino acids of SEQ ID NO:27, SEQ ID NO:29, SEQ ID NO:31 or SEQ ID NO:32, and wherein said antibody or an antigen-binding portion thereof binds the antigen recognized by the monocloncal antibody 5F4, 34B1, or 26H7.

2. The isolated CEACAM1-specific recombinant monoclonal antibody or an antigen binding portion thereof of claim 1, wherein the anti-CEACAM1-specific recombinant monoclonal antibody is a humanized antibody or portion thereof.

3. An isolated recombinant antibody or antigen-binding portion thereof comprising: a heavy chain complementarity determining region (CDR) 1 consisting of the amino acid residues of SEQ ID NO: 1, SEQ ID NO: 7, or SEQ ID NO: 13; a heavy chain CDR2 consisting of the amino acid residues of SEQ ID NO:2, SEQ ID NO: 8, or SEQ ID NO: 14; a heavy chain CDR3 consisting of the amino acid residues of SEQ ID NO: 3, or SEQ ID NO: 9, or SEQ ID NO: 15; a light chain CDR1 consisting of the amino acid residues of SEQ ID NO: 4, SEQ ID NO:10, SEQ ID NO:16, or SEQ ID NO:19;
a light chain CDR2 consisting of the amino acid residues of SEQ ID NO:5, SEQ ID NO:10, SEQ ID NO:17, or SEQ ID NO:20; and a light chain CDR3 consisting of the amino acid residues SEQ ID NO: 6, SEQ ID NO: 12, SEQ ID NO: 18, or SEQ ID NO: 21; such that said isolated recombinant antibody or antigen-binding portion thereof binds the antigen recognized by 5F4, 34B1, or 26H7.

4. The isolated CEACAM1-specific recombinant monoclonal antibody or an antigen-binding portion thereof of claim 3, wherein the antibody portion is a Fab fragment, a Fab' fragment, a Fd fragment, a Fd' fragment, a Fv fragment, a dAb fragment, a F(ab')$_2$ fragment, a single chain fragment, a diabody, or a linear antibody.

5. The antibody or antigen-binding portion thereof of claim 3, wherein said antibody is linked to a label.

6. The isolated CEACAM1-specific recombinant monoclonal antibody or an antigen-binding portion thereof of claim 3, further comprising an agent conjugated to the anti-CEACAM1 recombinant antibody or portion thereof to form an immunoconjugate specific for CEACAM1.

7. The isolated CEACAM1-specific recombinant monoclonal antibody or an antigen-binding portion thereof of claim 6, wherein the agent conjugated to the antibody or antibody fragment thereof is a chemotherapeutic agent, a toxin, a radioactive isotope, a small molecule, an siRNA, a nanoparticle, or a microbubble.

8. A method of treating pancreatic cancer, the method comprising administering to a subject in need thereof a therapeutically effective amount of a pharmaceutical composition comprising an isolated recombinant antibody or antigen-binding portion thereof comprising: a heavy chain complementarity determining region (CDR) 1 consisting of the amino acid residues of SEQ ID NO: 1, SEQ ID NO: 7, or SEQ ID NO: 13; a heavy chain CDR2 consisting of the amino acid residues of SEQ ID NO:2, SEQ ID NO: 8, or SEQ ID NO: 14; a heavy chain CDR3 consisting of the amino acid residues of SEQ ID NO: 3, or SEQ ID NO: 9, or SEQ ID NO: 15; a light chain CDR1 consisting of the amino acid residues of SEQ ID NO: 4, SEQ ID NO:10, SEQ ID NO:16, or SEQ ID NO:19;
a light chain CDR2 consisting of the amino acid residues of SEQ ID NO:5, SEQ ID NO:10, SEQ ID NO:17, or SEQ ID NO:20; and a light chain CDR3 consisting of the amino acid residues SEQ ID NO: 6, SEQ ID NO: 12, SEQ ID NO: 18, or SEQ ID NO: 21; such that said isolated recombinant antibody or antigen-binding portion thereof binds the antigen recognized by 5F4, 34B1, or 26H7.

9. The method of claim 8, wherein the method further comprises the administration of one or more chemotherapeutic agents, angiogenesis inhibitors, cytotoxic agents, or anti-proliferative agents.

* * * * *